US012174201B2

(12) United States Patent
Van Eyk et al.

(10) Patent No.: US 12,174,201 B2
(45) Date of Patent: Dec. 24, 2024

(54) PROGNOSIS AND PROGRESSION BIOMARKERS FOR CHRONIC KIDNEY DISEASE

(71) Applicants: Cedars-Sinai Medical Center, Los Angeles, CA (US); THE JOHNS HOPKINS UNIVERSITY, Baltimore, MD (US)

(72) Inventors: Jennifer Van Eyk, Los Angeles, CA (US); Qin Fu, Beverly Hills, CA (US); Vidya Venkatraman, Los Angeles, CA (US); Zongming Fu, Laurel, MD (US); Josef Coresh, Chevy Chase, MD (US)

(73) Assignees: Cedars-Sinai Medical Center, Los Angeles, CA (US); The Johns Hopkins University, Baltimore, MD (US)

( * ) Notice: Subject to any disclaimer, the term of this patent is extended or adjusted under 35 U.S.C. 154(b) by 454 days.

(21) Appl. No.: 16/754,717

(22) PCT Filed: Oct. 12, 2018

(86) PCT No.: PCT/US2018/055726
§ 371 (c)(1),
(2) Date: Apr. 8, 2020

(87) PCT Pub. No.: WO2019/075411
PCT Pub. Date: Apr. 18, 2019

(65) Prior Publication Data
US 2020/0292558 A1    Sep. 17, 2020

Related U.S. Application Data

(60) Provisional application No. 62/571,688, filed on Oct. 12, 2017.

(51) Int. Cl.
*G01N 33/53* (2006.01)
*G01N 33/543* (2006.01)
*G01N 33/68* (2006.01)

(52) U.S. Cl.
CPC ....... *G01N 33/6893* (2013.01); *G01N 33/543* (2013.01); *G01N 33/6848* (2013.01); *G01N 2800/347* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 2006/0008804 A1 | 1/2006 | Chibout et al. | |
| 2011/0195429 A1* | 8/2011 | Anderberg | G01N 33/6893 435/7.1 |
| 2011/0237513 A1 | 9/2011 | Kas | |
| 2012/0135427 A1* | 5/2012 | Kypros | G01N 33/74 435/7.92 |
| 2012/0178642 A1 | 7/2012 | Salomon et al. | |
| 2013/0344196 A1 | 12/2013 | Al-Murrani et al. | |
| 2014/0038203 A1 | 2/2014 | Arthur et al. | |
| 2015/0104881 A1* | 4/2015 | Chen | G01N 33/6893 436/501 |
| 2015/0204874 A1 | 7/2015 | King et al. | |
| 2017/0052200 A1* | 2/2017 | Bulik | G01N 33/6893 |
| 2018/0024152 A1* | 1/2018 | Bystrom | G01N 33/92 506/9 |

FOREIGN PATENT DOCUMENTS

| | | |
|---|---|---|
| EP | 3695224 A1 | 8/2020 |
| KR | 1020110033484 A | 3/2011 |
| WO | 2018/136825 A1 | 7/2018 |
| WO | 2019/075411 A1 | 4/2019 |

OTHER PUBLICATIONS

Merchant, Michael, Mass spectrometry in Chronic Kidney Disease research, Adv. Chronic Kidney Dis. Nov. 2010;17(6): 455-468. (Year: 2010).*
Luczak et al., Deeper insight into chronic kidney disease-related atherosclerosis: comparative proteomic studies of blood plasma using 2DE and mass spectrometry, Journal of Translational Medicine, 2015, pp. 1-18. (Year: 2015).*
Torzewski et al., Animal Models of C-Reactive Protein, Hindawl Publishing Corporation, Mediators of Inflammation, vol. 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Vaziri, HDL abnormalities in nephrotic syndrome and chronic kidney disease, Nature Reviews, Nephrology, vol. 12, Jan. 2016, pp. 37-47. (Year: 2016).*
Levitsky et al., (Clinical and plasma proteomic markers correlating with chronic kidney disease after liver transplantation, American Journal of Transplantation , 2011; 11, pp. 1972-1978. (Year: 2011).*
Glorieux et al., New insights in molecular mechanisms involved in chronic kidney disease using high-resolution plasma protein analysis, Nephrol Dial Transplant, 2015, 30, pp. 1842-1852. (Year: 2015).*
Uchikawa et al., Serum Albumin Levels Predict Clinical Outcomes in crhonic kidney disease (CKD) Patients Undergoing Cardiac Resynchronization Therapy, Internal Medicine 53, 2014, pp. 555-561. (Year: 2014).*
Ozkok et al., Low serum pancreatic enzyme levels predict mortality and are associated with malnutition-inflammation-atherosclerosis syndrome in patients with chronic kidney disease, Int Urol Nephrol, Aug. 2012, pp. 1-8. (Year: 2012).*
EP 18867154.9 Partial Supplementary Search Report dated Jun. 25, 2021, 24 pages.
Good et al., Naturally Occurring Human Urinary Peptides for Use in Diagnosis of Chronic Kidney Disease, Molecular and Cellular Proteomics, 2010, vol. 9(11), pp. 2424-2437.

(Continued)

*Primary Examiner* — Gary Counts
(74) *Attorney, Agent, or Firm* — Nixon Peabody LLP; Linda B. Huber

(57) ABSTRACT

Described herein are methods for identification/discovery of protein biomarkers for chronic kidney disease (CKD) and diagnosing and/or prognosing and/or predicting progression of and/or treating chronic kidney disease (CKD).

5 Claims, 4 Drawing Sheets

Specification includes a Sequence Listing.

(56) References Cited

OTHER PUBLICATIONS

Iyengar et al., Genome-Wide Association and Trans-Ethnic Meta-Analysis for Advanced Diabetic Kidney Disease, Family Investigation of Nephropathy and Diabetes (FIND), PLOS Genetics, 2015, vol. 11(8), pp. 1-19.
Marimuthu et al., A Comprehensive Map of Human Urinary Proteome, Journal of Proteome Research, 2011, vol. 10(6), pp. 2734-2743.
Ooi et al., Plasma Apolipoprotein C-III Metabolism in Patients with Chronic Kidney Disease, Journal of Lipid Research, 2011, vol. 52, pp. 794-800.
Siwy et al., Multicentre Prospective Validation of a Urinary Peptidome-Based Classifier for the Diagnosis of Type 2 Diabetic Nephropathy, Nephrol Dial Transplant, 2014, vol. 29, pp. 1563-1570.
International Search Report and Written Opinion for PCT/US2018/055726 dated Feb. 4, 2019.
Kidney Week 2017, American Society of Nephrology Meeting, TGF Beta Pathway Enriched as Candidate Plasma Severity Biomarkers in CKD, Abstract: SA-PO359, Nov. 4, 2017, New Orleans, Louisiana, 2 pages.
EP 18867154.9 Extended European Search Report dated Nov. 29, 2021, 32 pages.
Tian et al., Podocyte-associated talin1 is critical for glomerular filatration barrier maintenance, The Journal of Clinical Investigation, 2014, 124(3), pp. 1098-1113.
Vivekanandan-Giri et al., Urine Glycoprotein Profile Reveals Novel Markers for Chronic Kidney Disease, International Journal of Proteomics, 2011, Article ID 214715, pp. 1-18.

* cited by examiner

PROGNOSIS AND PROGRESSION BIOMARKERS FOR CHRONIC KIDNEY DISEASE

CROSS-REFERENCE TO RELATED APPLICATION

This application is a National Phase of International Application No. PCT/US2018/055726, filed Oct. 12, 2018, which designated the U.S. and that International Application was published under PCT Article 21 (2) in English. This application claims the benefit Both applications include a claim of priority under 35 U.S.C. § 119 (e) of to U.S. Provisional Patent Application No. 62/571,688, filed on Oct. 12, 2017, which is incorporated herein by reference in its entirety the entirety of which is hereby incorporated by reference.

STATEMENT REGARDING FEDERALLY SPONSORED RESEARCH OR DEVELOPMENT

This invention was made with government support under Grant No. DK085689 awarded by National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Oct. 11, 2018 is named 065472-000706WO00_SL.txt and is 1,005 bytes in size.

FIELD OF THE INVENTION

Described herein are methods for identification/discovery of protein biomarkers for chronic kidney disease (CKD) and diagnosing and/or prognosing and/or predicting progression of and/or treating chronic kidney disease (CKD).

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Many people are at risk of developing kidney disease. As such there is a need for methods for identification/discovery of protein biomarkers for chronic kidney disease (CKD) and for diagnosing and/or prognosing and/or predicting progression of and/or treating chronic kidney disease (CKD).

SUMMARY OF THE INVENTION

The following embodiments and aspects thereof are described and illustrated in conjunction with systems, articles of manufacture, compositions and methods which are meant to be exemplary and illustrative, not limiting in scope.

In various embodiments, the present invention provides a method for prognosing chronic kidney disease in a subject, comprising: i) obtaining a sample from the subject, ii) detecting and determining an amount of at least one protein in the sample by at least one technique selected from the group consisting of mass spectrometry, antibody method, nucleic acid aptamer method, immunoassay, ELISA, immunoprecipitation, SISCAPA, Western blot, and combinations thereof; wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4). T-lymphoma invasion and metastasis-inducing protein 2 (UniProt Accession No. Q8IVF5), D-tyrosyl-tRNA (Tyr) deacylase 1 (UniProt Accession No. Q8TEA8), Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; iii) constructing a protein biomarker signature for the subject, wherein the biomarker signature comprises the amount of the protein in the sample from the subject; and iv) comparing the amount of the protein in the sample from the subject to an amount of the protein in a reference sample, wherein a change in the amount of the protein in the sample from the subject relative to the amount of the protein in the reference sample is a prognosis of chronic kidney disease in the subject.

In some embodiments, the mass spectrometry is selected from the group consisting of SRM, MRM, PRM, DDA, DIA, LC-MS, LC-MS/MS, LC-SRM-MS, LC-MRM-MS, LC-PRM-MS, LC-DDA-MS, LC-DIA-MS, and combinations thereof. In some embodiments, the subject is human. In some embodiments, the sample is plasma. In some embodiments, the reference sample is obtained from a control subject, wherein the control subject does not have chronic kidney disease. In some embodiments, the reference sample is obtained from the subject before the subject is treated for chronic kidney disease. In some embodiments, the reference sample is from a subject that has been successfully treated for chronic kidney disease. In some embodiments, the method further comprises administering a treatment to the subject. In some embodiments, the method further comprises, administering a treatment to the subject; obtaining a post-treatment sample from the subject; detecting the at least one protein in the post-treatment sample from the subject according to the method; determining the amount of the protein in the post-treatment sample from the subject according to the method; and comparing the amount of the protein in the post-treatment sample from the subject to an amount of the protein in a reference sample, wherein a change in the amount of the protein in the post-treatment sample from the subject relative to the amount of the protein in the reference sample is indicative of the efficacy of the treatment. In some embodiments, the reference sample is obtained from a control subject, wherein the control subject does not have chronic kidney disease. In some embodiments, the reference sample is obtained from the subject before the subject is treated for chronic kidney disease. In some embodiments, the reference sample is from a subject that has been successfully treated for chronic kidney disease.

In various embodiments, the present invention provides a method for determining progression of chronic kidney disease in a subject, comprising: i) obtaining a sample from the subject; ii) detecting and determining an amount of at least one protein in the sample by at least one technique selected from the group consisting of mass spectrometry, antibody method, nucleic acid aptamer method, immunoassay, ELISA, immunoprecipitation, SISCAPA, Western blot, and combinations thereof, wherein the protein is selected from the group consisting of Uteroglobin (UniProt Accession No. P11684), Putative sodium-coupled neutral amino acid transporter 10 (UniProt Accession No. Q9HBR0), Protein AMBP (precursors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859), Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; iii) constructing a protein biomarker signature for the subject, wherein the biomarker signature comprises the amount of the protein in the sample from the subject; and iv) comparing the amount of the protein in the sample from the subject to an amount of the protein in a reference sample, wherein a change in the amount of the protein in the sample from the subject relative to the amount of the protein in the reference sample is indicative of progression of chronic kidney disease in the subject.

In some embodiments, the mass spectrometry is selected from the group consisting of SRM, MRM, PRM, DDA, DIA, LC-MS, LC-MS/MS, LC-SRM-MS, LC-MRM-MS, LC-PRM-MS, LC-DDA-MS, LC-DIA-MS, and combinations thereof. In some embodiments, the subject is human. In some embodiments, the sample is plasma. In some embodiments, the reference sample is obtained from a control subject, wherein the control subject does not have chronic kidney disease. In some embodiments, the reference sample is obtained from the subject before the subject is treated for chronic kidney disease. In some embodiments, the reference sample is from a subject that has been successfully treated for chronic kidney disease. In some embodiments, the method further comprises administering a treatment to the subject. In some embodiments, the method further comprises administering a treatment to the subject; obtaining a post-treatment sample from the subject; detecting the at least one protein in the post-treatment sample from the subject according to the method; determining the amount of the protein in the post-treatment sample from the subject according to the method; and comparing the amount of the protein in the post-treatment sample from the subject to an amount of the protein in a reference sample, wherein a change in the amount of the protein in the post-treatment sample from the subject relative to the amount of the protein in the reference sample is indicative of the efficacy of the treatment. In some embodiments, the reference sample is obtained from a control subject, wherein the control subject does not have chronic kidney disease. In some embodiments, the reference sample is obtained from the subject before the subject is treated for chronic kidney disease. In some embodiments, the reference sample is from a subject that has been successfully treated for chronic kidney disease.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 2 discloses sequence SDVVY (SEQ ID NO: 3) and sequence GWVTDGFSSL (SEQ ID NO: 4).

DETAILED DESCRIPTION OF THE INVENTION

Figure 1:
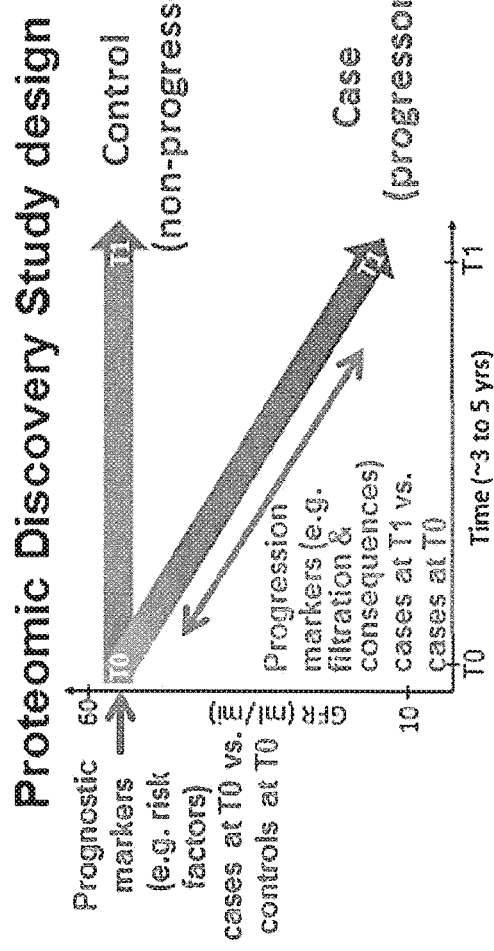
FIG. 1 depicts in accordance with various embodiments of the invention, a schematic representation of design for CKD discovery (and verification/validation). Comparison of cases and controls at time 0 (baseline) yields candidate prognostic markers while comparison of changes over time in cases yields candidate progression markers.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3rd ed., revised ed., J. Wiley & Sons (New York, NY 2006); Smith, *March's Advanced Organic Chemistry Reactions, Mechanisms and Structure* 7$^{th}$ ed., J. Wiley & Sons (New York, NY 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, NY 2012), provide one skilled in the art with a general guide to many of the terms used in the present application.

For references on mass spectrometry and proteomics, see e.g., Salvatore Sechi, *Quantitative Proteomics by Mass Spectrometry* (Methods in Molecular Biology) 2nd ed. 2016 Edition, Humana Press (New York, NY, 2009); Daniel Martins-de-Souza, Shotgun *Proteomics: Methods and Protocols* 2014 edition, Humana Press (New York, NY, 2014); Jörg Reinders and Albert Sickmann, *Proteomics: Methods and Protocols* (Methods in Molecular Biology) 2009 edition, Humana Press (New York, NY, 2009); and Jörg Reinders, *Proteomics in Systems Biology: Methods and Protocols* (Methods in Molecular Biology) 1$^{st}$ ed. 2016 edition, Humana Press (New York, NY, 2009).

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, systems, articles of manufacture, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

"Optional" or "optionally" means that the subsequently described circumstance may or may not occur, so that the description includes instances where the circumstance occurs and instances where it does not.

"Sample" is used herein in its broadest sense. The term "biological sample" as used herein denotes a sample taken or isolated from a biological organism. A sample or biological sample may comprise a bodily fluid including blood, serum, plasma, tears, aqueous and vitreous humor, spinal fluid; a soluble fraction of a cell or tissue preparation, or media in which cells were grown; or membrane isolated or extracted from a cell or tissue; polypeptides, or peptides in solution or bound to a substrate; a cell; a tissue; a tissue print; a fingerprint, skin or hair; fragments and derivatives thereof. Non-limiting examples of samples or biological samples include cheek swab; mucus; whole blood, blood, serum; plasma; urine; saliva; semen; lymph; fecal extract; sputum; other body fluid or biofluid; cell sample; and tissue sample etc. The term also includes a mixture of the above-mentioned samples or biological samples. The term "sample" also includes untreated or pretreated (or pre-processed) biological samples. In some embodiments, a sample or biological sample can comprise one or more cells from the subject. Subject samples or biological samples usually comprise derivatives of blood products, including blood, plasma and serum. In some embodiments, the sample is a biological sample. In some embodiments, the sample is blood. In some embodiments, the sample is plasma. In some embodiments, the sample is blood, plasma, serum, or urine.

The terms "body fluid" or "bodily fluids" are liquids originating from inside the bodies of organisms. Bodily fluids include amniotic fluid, aqueous humour, vitreous humour, bile, blood (e.g., serum), breast milk, cerebrospinal fluid, cerumen (earwax), chyle, chyme, endolymph and perilymph, exudates, feces, female ejaculate, gastric acid, gastric juice, lymph, mucus (e.g., nasal drainage and phlegm), pericardial fluid, peritoneal fluid, pleural fluid, pus, rheum, saliva, sebum (skin oil), serous fluid, semen, smegma, sputum, synovial fluid, sweat, tears, urine, vaginal secretion, and vomit. Extracellular bodily fluids include intravascular fluid (blood plasma), interstitial fluids, lymphatic fluid and transcellular fluid. "Biological sample" also includes a mixture of the above-mentioned body fluids. "Biological samples" may be untreated or pretreated (or pre-processed) biological samples.

Sample collection procedures and devices known in the art are suitable for use with various embodiment of the present invention. Examples of sample collection procedures and devices include but are not limited to: phlebotomy tubes (e.g., a vacutainer blood/specimen collection device for collection and/or storage of the blood/specimen), dried blood spots, Microvette CB300 Capillary Collection Device (Sarstedt), HemaXis blood collection devices (microfluidic technology, Hemaxis), Volumetric Absorptive Microsampling (such as CE-IVD Mitra microsampling device for accurate dried blood sampling (Neoteryx), HemaSpot™-HF Blood Collection Device, a tissue sample collection device; standard collection/storage device (e.g., a collection/storage device for collection and/or storage of a sample (e.g., blood, plasma, serum, urine, etc.); a dried blood spot sampling device. In some embodiments, the Volumetric Absorptive Microsampling (VAMS™) samples can be stored and mailed, and an assay can be performed remotely.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. In various embodiments, the subject is mouse or mice. In various embodiments, the subject is human.

In some embodiments, the subject is selected from the group consisting of a subject suspected of having kidney disease, a subject that has kidney disease, a subject diagnosed with kidney disease, a subject that has been treated for kidney disease, a subject that is being treated for kidney disease, and a subject that is at risk of developing kidney disease.

In some embodiments, the subject is selected from the group consisting of a subject suspected of having chronic kidney disease, a subject that has chronic kidney disease, a subject diagnosed with chronic kidney disease, a subject that has been treated for chronic kidney disease, a subject that is being treated for chronic kidney disease, and a subject that is at risk of developing chronic kidney disease.

In some embodiments, the subject is selected from the group consisting of a subject suspected of having a disease, a subject that has a disease, a subject diagnosed with a disease, a subject that has been treated for a disease, a subject that is being treated for a disease, and a subject that is at risk of developing a disease.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, -carboxyglutamate, and O-phosphoserine. Amino acid analogs refers to compounds that have the same basic chemical structure as a naturally occurring amino acid, i.e., an carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A protein refers to any of a class of nitrogenous organic compounds that comprise large molecules composed of one or more long chains of amino acids and are an essential part of all living organisms. A protein may contain various modifications to the amino acid structure such as disulfide bond formation, phosphorylations and glycosylations. A linear chain of amino acid residues may be called a "polypeptide." A protein contains at least one polypeptide. Short polypeptides, e.g., containing less than 20-30 residues, are sometimes referred to as "peptides."

The term "threshold" as used herein refers to the magnitude or intensity that must be exceeded for a certain reaction, phenomenon, result, or condition to occur or be considered relevant. The relevance can depend on context, e.g., it may refer to a positive, reactive or statistically significant relevance.

The term "condition" (biological state or health state) is understood in the present invention as status of a subject that can be described by physical, mental or social criteria. It includes as well so-called "healthy" and "diseased" conditions, therefore it is not limited to the WHO definition of health as "a state of complete physical, mental, and social well-being and not merely the absence of disease or infirmity." but includes disease and infirmity.

The term "disease" refers to an abnormal condition affecting the body of an organism. The term "disorder" refers to a functional abnormality or disturbance. The terms disease or disorder are used interchangeably herein unless otherwise noted or clear given the context in which the term is used.

The term "state of health" includes at least one condition as defined herein. It may also include a plurality of different conditions. In some embodiments, the state of health is a healthy state. In some embodiments, the state of health is a diseased state.

The term "healthy state" or "normal state" means that the state of a subject (e.g., biological state or health state, etc.) is not abnormal or does not comprise a disease or disorder.

A "healthy subject" or "normal subject" is a subject that does not have a disease or disorder.

As used herein, the terms "treat", "treatment", "treating", or "amelioration" when used in reference to a disease, disorder or medical condition, refer to both therapeutic treatment and prophylactic or preventative measures, wherein the object is to reverse, alleviate, ameliorate, inhibit, lessen, slow down or stop the progression or severity of a symptom, a condition, a disease, or a disorder. The term "treating" includes reducing or alleviating at least one adverse effect or symptom of a condition, a disease, or a disorder. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition, disease, or disorder even if the treatment is ultimately unsuccessful. Those in need of treatment include those already with the condition, disease, or disorder as well as those prone to have the condition, disease, or disorder or those in whom the condition, disease, or disorder is to be prevented.

Non-limiting examples of treatments or therapeutic treatments include pharmacological or biological therapies and/or interventional surgical treatments.

The term "preventative treatment" means maintaining or improving a healthy state or non-diseased state of a healthy subject or subject that does not have a disease. The term "preventative treatment" or "health surveillance" also means to prevent or to slow the appearance of symptoms associated with a condition, disease, or disorder. The term "preventative treatment" also means to prevent or slow a subject from obtaining a condition, disease, or disorder.

In various embodiments, the treatments or kits may be provided as pharmaceutical compositions. In various embodiments, the pharmaceutical compositions may be formulated for delivery via any route of administration. "Route of administration" may refer to any administration pathway known in the art, including but not limited to aerosol, nasal, via inhalation, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. Methods for these administrations are known to one skilled in the art. In certain embodiments, the pharmaceutical compositions are formulated for intravascular, intravenous, or intraarterial administration.

In various embodiments, the pharmaceutical compositions can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its imaging benefits.

The pharmaceutical compositions can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical compositions are made following the conventional techniques of pharmacy involving dry milling, mixing, and blending for powder forms; milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

Before administration to patients, formulants may be added to the pharmaceutical composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, in some embodiments between 2.0 and 6.0 w/v %.

Polymers formulants include polyvinylpyrrolidone (PVP) with an average molecular weight between 2,000 and 3,000, or polyethylene glycol (PEG) with an average molecular weight between 3,000 and 5,000.

A buffer may also be used in the pharmaceutical compositions to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

After the pharmaceutical composition is prepared, it may be lyophilized to prevent degradation and to preserve sterility. Methods for lyophilizing pharmaceutical compositions are known to those of ordinary skill in the art. Just prior to use, the pharmaceutical composition may be reconstituted with a sterile diluent (Ringer's solution, distilled water, or sterile saline, for example) which may include additional ingredients. Upon reconstitution, the pharmaceutical composition is administered to subjects using those methods that are known to those skilled in the art.

The pharmaceutical compositions may be sterilized by conventional, well-known sterilization techniques. The resulting solutions may be packaged for use or filtered under aseptic conditions and lyophilized, the lyophilized preparation being combined with a sterile solution prior to administration. The pharmaceutical compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

Many variations and alternative elements have been disclosed in embodiments of the present invention. Still further variations and alternate elements will be apparent to one of skill in the art. Various embodiments of the invention can specifically include or exclude any of these variations or elements.

In some embodiments, the numbers expressing quantities of ingredients, properties such as concentration, reaction conditions, time, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

"Beneficial results" or "desired results" may include, but are in no way limited to, lessening or alleviating the severity of the disease or condition, preventing the disease or condition from worsening, curing the disease or condition, preventing the disease or condition from developing, lowering the chances of a patient developing the disease or condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of chronic kidney disease, delay or slowing of chronic kidney disease, and amelioration or palliation of symptoms associated with chronic kidney disease.

As used herein, the term "administering," refers to the placement an agent or a treatment as disclosed herein into a subject by a method or route which results in at least partial localization of the agent or treatment at a desired site. "Route of administration" may refer to any administration pathway known in the art, including but not limited to aerosol, nasal, via inhalation, oral, anal, intra-anal, peri-anal, transmucosal, transdermal, parenteral, enteral, topical or local. "Parenteral" refers to a route of administration that is generally associated with injection, including intratumoral, intracranial, intraventricular, intrathecal, epidural, intradural, intraorbital, infusion, intracapsular, intracardiac, intradermal, intramuscular, intraperitoneal, intrapulmonary, intraspinal, intrasternal, intrathecal, intrauterine, intravascular, intravenous, intraarterial, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

"Diagnostic" means identifying the presence or nature of a pathologic condition, disease, or disorder and includes identifying patients who are at risk of developing a specific condition, disease or disorder. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, a disease, or a disorder, it suffices if the method provides a positive indication that aids in diagnosis.

By "at risk of" is intended to mean at increased risk of, compared to a normal subject, or compared to a control group, e.g. a patient population. Thus a subject carrying a particular marker may have an increased risk for a specific condition, disease or disorder, and be identified as needing further testing. "Increased risk" or "elevated risk" mean any statistically significant increase in the probability, e.g., that the subject has the disorder. The risk is increased by at least 10%, at least 20%, and even at least 50% over the control group with which the comparison is being made.

The term "statistically significant" or "significantly" refers to statistical evidence that there is a difference. It is defined as the probability of making a decision to reject the null hypothesis when the null hypothesis is actually true. The decision is often made using the p-value.

The terms "detection", "detecting" and the like, may be used in the context of detecting biomarkers, detecting peptides, detecting proteins, or of detecting a condition, detecting a disease or a disorder (e.g. when positive assay results are obtained). In the latter context, "detecting" and "diagnosing" are considered synonymous.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

"Immunoassay" is an assay that uses an antibody to specifically bind an antigen (e.g., a marker). The immunoassay is characterized by the use of specific binding properties of a particular antibody to isolate, target, and/or quantify the antigen. Non-limiting examples of immunoassays include ELISA (enzyme-linked immunosorbent assay), immunoprecipitation, SISCAPA (stable isotope standards and capture by anti-peptide antibodies), Western blot, etc.

A subject can be one who has been previously diagnosed with or identified as suffering from or having a condition, disease, or disorder in need of treatment (e.g., chronic kidney disease) or one or more complications related to the condition, disease, or disorder, and optionally, have already undergone treatment for the condition, disease, disorder, or the one or more complications related to the condition, disease, or disorder. Alternatively, a subject can also be one who has not been previously diagnosed as having a condition, disease, or disorder or one or more complications related to the condition, disease, or disorder. For example, a subject can be one who exhibits one or more risk factors for a condition, disease, or disorder, or one or more complications related to the condition, disease, or disorder, or a subject who does not exhibit risk factors. A "subject in need" of treatment for a particular condition, disease, or disorder can be a subject suspected of having that condition, disease, or disorder, diagnosed as having that condition, disease, or disorder, already treated or being treated for that condition, disease, or disorder, not treated for that condition, disease, or disorder, or at risk of developing that condition, disease, or disorder.

The terms "proteases" and "peptidases" are used interchangeably herein to mean enzymes that breakdown proteins and peptides.

The term "phenotype" as used herein comprises the composite of an organism's observable characteristics or traits, such as its morphology, development, biochemical or physiological properties, phenology, behavior, and products of behavior.

The term "diagnosis," or "dx," refers to the identification of the nature and cause of a certain phenomenon. As used herein, a diagnosis typically refers to a medical diagnosis, which is the process of determining which disease or condition explains a symptoms and signs. A diagnostic procedure, often a diagnostic test or assay, can be used to provide a diagnosis. A diagnosis can comprise detecting the presence of a disease or disorder, or condition.

The term "prognosis," or "px," as used herein refers to predicting the likely outcome of a current standing. For example, a prognosis can include the expected duration and course of a disease or disorder, such as progressive decline or expected recovery.

The term "theranosis," or "tx" as used herein refers to a diagnosis or prognosis used in the context of a medical treatment. For example, theranostics can include diagnostic testing used for selecting appropriate and optimal therapies (or the inverse) based on the context of genetic content or other molecular or cellular analysis. Theranostics includes pharmacogenomics, personalized and precision medicine.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. Beneficial or desired clinical results include, but are not limited to, alleviation of one or more symptom(s), diminishment of extent of the deficit, stabilized (i.e., not worsening) state of progression, delay or slowing of progression or invasiveness, and amelioration or palliation of symptoms associated with the chronic kidney disease. Treatment also includes a decrease in mortality or an increase in the lifespan of a subject as compared to one not receiving the treatment.

As used herein, the terms "treat," "treatment," "treating," or "amelioration" refer to therapeutic treatments, wherein the object is to reverse, alleviate, ameliorate, inhibit, slow down or stop the progression or severity of a condition, disease or disorder. The term "treating" includes reducing or alleviating at least one adverse effect or symptom of a condition, disease or disorder described herein. Treatment is generally "effective" if one or more symptoms are reduced. Alternatively, treatment is "effective" if the progression of a disease is reduced or halted. That is, "treatment" includes not just the improvement of symptoms, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

The term "preventative treatment" means maintaining or improving a healthy state or non-diseased state of a healthy subject or subject that does not have a disease. The term "preventative treatment" also means to prevent or to slow the appearance of symptoms associated with a condition, disease, or disorder. The term "preventative treatment" also means to prevent or slow a subject from obtaining a condition, disease, or disorder.

General molecular biology terminology and techniques are known to those of skill in the art. See, e.g., Sambrook et al., Molecular Cloning: A Laboratory Manual, Cold Spring Harbor Press, N.Y., (3.sup. rd ed., 2000); and Brent et al., Current Protocols in Molecular Biology, John Wiley & Sons, Inc. (ringbou ed., 2003).

As described herein, the compositions and methods of the invention may be used to characterize a phenotype in a sample of interest. The phenotype can be any phenotype of interest that may be characterized using the subject compositions and methods. Consider a non-limiting example wherein the phenotype comprises a disease or disorder. In such cases, the characterizing may be providing a diagnosis, prognosis or theranosis for the disease or disorder. In an illustrative embodiment, a sample from a subject is analyzed using the compositions and methods of the invention. The analysis is then used to predict or determine the presence, stage, grade, outcome, or likely therapeutic response of a disease or disorder in the subject. The analysis can also be used to assist in making such prediction or determination.

In various embodiments the invention provides a method to identify protein biomarkers and patterns that are indicative of a disease. In various embodiments the invention provides a method to identify protein biomarkers and patterns that are indicative a disease is or may be present. In some embodiments these methods may provide objective rationale for further testing. In various embodiments the invention provides a method for the identification of a plurality of proteins from a sample, wherein each protein is correlated to one or more peptides, wherein each peptide is correlated to one or more transitions, wherein each transition comprises a Q1 mass value. In various embodiments the invention provides a method for the identification of a plurality of proteins from a sample, wherein each protein is correlated to one or more peptides, wherein each peptide is correlated to one or more transitions, wherein each transition comprises a Q1 mass value and a Q3 mass value. In various embodiments the invention provides a method for the identification of a plurality of proteins from a sample, wherein each protein is correlated to one or more peptides, wherein each peptide is correlated to one or more transitions, wherein each transition comprises a Q1/Q3 mass value pair.

As used herein, SRM stands for selected reaction monitoring. As used herein, MRM stands for multiple reaction monitoring. As used herein, PRM stands for parallel reaction monitoring. As used herein, SWATH stands for sequential window acquisition of all theoretical fragment ion spectra. As used herein, DIA stands for data-independent acquisition. As used herein, MS stands for mass spectrometry. As used herein, SIL stands for stable isotope-labeled.

As used herein, "MS data" can be raw MS data obtained from a mass spectrometer and/or processed MS data in which peptides and their fragments (e.g., transitions and MS peaks) are already identified, analyzed and/or quantified. MS data can be Selective Reaction Monitoring (SRM) data, Multiple Reaction Monitoring (MRM) data, parallel reaction monitoring (PRM) data, Shotgun CID MS data, Original DIA MS Data, MSE MS data, p2CID MS Data, PAcIFIC MS Data, AIF MS Data, XDLA MS Data, SWATH MS data, or FT-ARM MS Data, or their combinations.

In some embodiments of the present invention, based on SRM and/or MS, and/or PRM MS, allows for the detection and accurate quantification of specific peptides in complex mixtures.

Selected Reaction Monitoring or Multiple Reaction Monitoring (SRM/MRM) mass spectrometry is a technology with the potential for reliable and comprehensive quantification of substances of low abundance in complex samples. SRM is performed on triple quadrupole-like instruments, in which increased selectivity is obtained through collision-induced dissociation. It is a non-scanning mass spectrometry technique, where two mass analyzers (Q1 and Q3) are used as static mass filters, to monitor a particular fragment of a selected precursor. On triple quadrapole instruments, various ionization methods can be used including without limitation electrospray ionization, chemical ionization, electron ionization, atmospheric pressure chemical ionization, and matrix-assisted laser desorption ionization. Both the first mass analyzer and the collision cell are continuously exposed to ions from the source in a time dependent manner. Once the ions move into the third mass analyzer time dependence becomes a factor. On triple quadrupole instruments, the first quadrapole mass filter, Q1, is the primary m/z selector after the sample leaves the ionization source. Any ions with mass-to-charge ratios other than the one selected for will not be allowed to infiltrate Q1. The collision cell, denoted as "q2", located between the first quadrupole mass filter Q1 and second quadrupole mass filter Q3, is where fragmentation of the sample occurs in the presence of an inert gas like argon, helium, or nitrogen. Upon exiting the collision cell, the fragmented ions then travel onto the second quadrapole mass filter Q3, where m/z selection can occur again. The specific pair of mass-over-charge (m/z) values associated to the precursor and fragment ions selected is referred to as a "transition". The detector acts as a counting device for the ions matching the selected transition thereby returning an intensity distribution over time. MRM is when multiple SRM transitions are measured within the same experiment on the chromatographic time scale by rapidly switching between the different precursor/fragment pairs. Typically, the triple quadrupole instrument cycles through a series of transitions and records the signal of each transition as a function of the elution time. The method allows for additional selectivity by monitoring the chromatographic co-elution of multiple transitions for a given analyte.

In addition to MRM, the choice of peptides can also be quantified through Parallel-Reaction Monitoring (PRM). Parallel reaction monitoring (PRM) is the application of SRM with parallel detection of all transitions in a single analysis using a high resolution mass spectrometer. PRM provides high selectivity, high sensitivity and high-throughput to quantify selected peptide (Q1), hence quantify proteins. Again, multiple peptides can be specifically selected for each protein. PRM methodology uses the quadrupole of a mass spectrometer to isolate a target precursor ion, fragments the targeted precursor ion in the collision cell, and then detects the resulting product ions in the Orbitrap mass analyzer. Quantification is carried out after data acquisition by extracting one or more fragment ions with 5-10 ppm mass windows. PRM uses a quadrupole time-of-flight (QTOF) or hybrid quadrupole-orbitrap (QOrbitrap) mass spectrometer to carry out the peptides/proteins quantitation. Examples of QTOF include but are not limited to: TripleTOF® 6600 or 5600 System (Sciex); X500R QTOF System (Sciex); 6500 Series Accurate-Mass Quadrupole Time-of-Flight (Q-TOF) (Agilent); or Xevo G2-XS QTof Quadrupole Time-of-Flight Mass Spectrometry (Waters). Examples of QObitrap include but are not limited to: Q Exactive™ Hybrid Quadrupole-Orbitrap Mass Spectrometer (the Thermo Scientific); or Orbitrap Fusion™ Tribrid™ (the Thermo Scientific).

Non-limiting advantages of PRM include elimination of most interferences, provides more accuracy and attomole-level limits of detection and quantification, enables the confident confirmation of the peptide identity with spectral library matching, reduces assay development time since no target transitions need to be preselected, ensures UHPLC-compatible data acquisition speeds with spectrum multiplexing and advanced signal processing.

SWATH MS is a data independent acquisition (DIA) method which aims to complement traditional mass spectrometry-based proteomics techniques such as shotgun and SRM methods. In essence, it allows a complete and permanent recording of all fragment ions of the detectable peptide precursors present in a biological sample. It thus combines the advantages of shotgun (high throughput) with those of SRM (high reproducibility and consistency).

In some embodiments, the developed methods herein can be applied to the quantification of polypeptides(s) or protein(s) in biological sample(s). Any kind of biological samples comprising polypeptides or proteins can be the starting point and be analyzed by the methods herein. Indeed, any protein/peptide containing sample can be used for and analyzed by the methods produced here (e.g., tissues, cells). The methods herein can also be used with peptide mixtures obtained by digestion. Digestion of a polypeptide or protein includes any kind of cleavage strategies, such as, enzymatic, chemical, physical or combinations thereof.

The deciding factors of which polypeptide or protein will be the one of interest varies. It can be decided by performing a literature search and identifying proteins that are functionally related, are candidate protein biomarkers which can be used in screening for drug discovery, biomarker discovery and/or disease clinical phase trials or are diagnostic markers to screen for pharmaceutical/medical purposes. The polypeptide or protein of interest may be determined by experimental analysis.

According to some embodiments, the following parameters of the methods provided herein are determined: trypsin (or other protease) digestion and peptide clean up, best responding polypeptides, best responding proteins, best responding peptides, best responding fragments, fragment intensity ratios (increased high and reproducible peak intensities), optimal collision energies, and all the optimal parameters to maximize sensitivity and/or specificity of the methods.

In other embodiments, quantification of the polypeptides and/or of the corresponding proteins or activity/regulation of the corresponding proteins is desired. A selected peptide is labeled with a stable-isotope and used as an internal standard to achieve absolute quantification of a protein of interest. The addition of a quantified stable-labeled peptide analogue of the tag to the peptide sample in known amount; and subsequently the tag and the peptide of interest is quantified by mass spectrometry and absolute quantification of the endogenous levels of the proteins is obtained.

In some embodiments, the analysis and/or comparison is done on protein samples of wild-type or physiological/healthy origin against protein samples of mutant or pathological origin, The present invention supports the use of mass spectrometry as platform to identify signature polypeptides or proteins for quantitative proteomics. The approach is applicable to the analysis of proteins from all organisms, from cells, organs, tissues, and in the context of in vivo and/or in vitro analyses. Examples of applications of the invention include the development, use and commercialization of quantitative assays for sets of polypeptides or proteins of interest. The invention can be beneficial for the pharmaceutical industry (e.g. drug development and assessment), the biotechnology industry (e.g. assay design and development and quality control), and in clinical applications (e.g. identification of biomarkers of disease and quantitative analysis for diagnostic, prognostic and/or therapeutic use).

In some embodiments, the beta coefficients can be negative or positive, and have a t-value and significance of that t-value associated with each. Think of the regression beta coefficient as the slope of a line: the t-value and significance assesses the extent to which the magnitude of the slope is significantly different from the line laying on the X-axis. If the beta coefficient is not statistically significant (i.e., the t-value is not significant), no statistical significance can be interpreted from that predictor. If the beta coefficient is significant, examine the sign of the beta. If the regression beta coefficient is positive, the interpretation is that for every 1-unit increase in the predictor variable, the dependent variable will increase by the unstandardized beta coefficient value. For example, if the beta coefficient is 0.80 and statistically significant, then for each unit increase in the predictor variable, the outcome variable will increase by 0.80 units. The positive beta value indication of increased expression and negative beta value indicative of decreased expression.

The terms "marker" or "biomarker" are used interchangeably herein, and in the context of the present invention refer to a protein or peptide (for example, protein or peptide associated with kidney disease or chronic kidney disease as described herein) is differentially present in a sample taken from patients having a specific disease or disorder as compared to a control value, the control value consisting of, for example average or mean values in comparable samples taken from control subjects (e.g., a person with a negative diagnosis, normal or healthy subject). Biomarkers may be determined as specific peptides or proteins (Tables 1, 2, 6, and/or 7) which may be detected by antibodies or mass spectroscopy. In some applications, for example, a mass spectroscopy or other profile of multiple antibodies may be used to determine multiple biomarkers, and differences between individual biomarkers and/or the partial or complete profile may be used for diagnosis. In some embodiments, the biomarkers may be detected by antibodies, mass spectrometry, or combinations thereof.

A "test amount" of a marker refers to an amount of a marker present in a sample being tested. A test amount can be either in absolute amount (e.g., µg/ml) or a relative amount (e.g., relative intensity of signals).

A "diagnostic amount" of a marker refers to an amount of a marker in a subject's sample that is consistent with a diagnosis of a particular disease or disorder. A diagnostic amount can be either in absolute amount (e.g., µg/ml) or a relative amount (e.g., relative intensity of signals).

A "control amount" of a marker can be any amount or a range of amount which is to be compared against a test amount of a marker. For example, a control amount of a marker can be the amount of a marker in a person who does not suffer from the disease or disorder sought to be diagnosed. A control amount can be either in absolute amount (e.g., µg/ml) or a relative amount (e.g., relative intensity of signals).

The term "differentially present" or "change in level" refers to differences in the quantity and/or the frequency of a marker present in a sample taken from patients having a specific disease or disorder as compared to a control subject. For example, a marker can be present at an elevated level or at a decreased level in samples of patients with the disease or disorder compared to a control value (e.g. determined from samples of control subjects). Alternatively, a marker can be detected at a higher frequency or at a lower frequency in samples of patients compared to samples of control subjects. A marker can be differentially present in terms of quantity, frequency or both as well as a ratio of differences between two or more specific modified amino acid residues and/or the enzyme itself. In one embodiment, an increase in the ratio of modified to unmodified proteins and peptides described herein is diagnostic of any one or more of the diseases described herein.

A marker, compound, composition or substance is differentially present in a sample if the amount of the marker, compound, composition or substance in the sample is statistically significantly different from the amount of the marker, compound, composition or substance in another sample, or from a control value. For example, a compound is differentially present if it is present at least about 120%, at least about 130%, at least about 150%, at least about 180%, at least about 200%, at least about 300%, at least about 500%, at least about 700%, at least about 900%, or at least about 1000% greater or less than it is present in the other sample (e.g. control), or if it is detectable in one sample and not detectable in the other.

Alternatively, or additionally, a marker, compound, composition or substance is differentially present between samples if the frequency of detecting the marker, etc. in samples of patients suffering from a particular disease or disorder, is statistically significantly higher or lower than in the control samples or control values obtained from healthy individuals. For example, a biomarker is differentially present between the two sets of samples if it is detected at least about 10%, at least about 20, at least about 30%, at least about 40%, at least about 50%, at least about 60%, at least about 70%, at least about 80%, at least about 90%, or at least about 100% more frequently or less frequently observed in one set of samples than the other set of samples. These exemplary values notwithstanding, it is expected that a skilled practitioner can determine cut-off points, etc. that represent a statistically significant difference to determine whether the marker is differentially present.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, digoxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, flow cytometry, or direct analysis by mass spectrometry of intact protein or peptides. In some embodiments, the detectable moiety is a stable isotope. In some embodiments, the stable isotope is selected from the group consisting of $^{15}N$, $^{13}C$, $^{18}O$, and $^{2}H$.

By "binding assay" is meant a biochemical assay wherein the biomarkers are detected by binding to an agent, such as an antibody, through which the detection process is carried out. The detection process may involve radioactive or fluorescent labels, and the like. The assay may involve immobilization of the biomarker, or may take place in solution.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity).

The term "peptide" as used herein refers to any compound containing at least two amino acid residues joined by an amide bond formed from the carboxyl group of one amino acid residue and the amino group of the adjacent amino acid residue. In some embodiments, peptide refers to a polymer of amino acid residues typically ranging in length from 2 to about 30, or to about 40, or to about 50, or to about 60, or to about 70 residues. In certain embodiments the peptide ranges in length from about 2, 3, 4, 5, 7, 9, 10, or 11 residues to about 60, 50, 45, 40, 45, 30, 25, 20, or 15 residues. In certain embodiments the peptide ranges in length from about 8, 9, 10, 11, or 12 residues to about 15, 20 or 25 residues. In some embodiments, the peptide ranges in length from 2 to about 12 residues, or 2 to about 20 residues, or 2 to about 30 residues, or 2 to about 40 residues, or 2 to about 50 residues, or 2 to about 60 residues, or 2 to about 70 residues. In certain embodiments the amino acid residues comprising the peptide are "L-form" amino acid residues, however, it is recognized that in various embodiments, "D" amino acids can be incorporated into the peptide. Peptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an a-ester, a ß-ester, a thioamide, phosphonamide, carbamate, hydroxylate, and the like (see, e.g., Spatola, (1983) Chem. Biochem. Amino Acids and Proteins 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

As used herein the terms "one or more" and "at least one" are used interchangeably.

VARIOUS NON-LIMITING EMBODIMENTS OF THE INVENTION

In various embodiments, the disease referred to herein is kidney disease. In various embodiments, the disease referred to herein is chronic kidney disease.

In various embodiments, the present invention provides a method for identifying protein biomarkers of chronic kidney disease in a subject, comprising: obtaining a sample from the subject, wherein the subject has chronic kidney disease; treating the sample with one or more proteases to obtain a digested sample comprising one or more peptides; detecting and/or measuring and/or quantifying the peptides in the digested sample, wherein the detecting and/or measuring and/or quantifying is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample; wherein protein biomarkers of chronic kidney disease are identified. In some embodiments, the detecting and/or measuring and/or quantifying the peptides in the digested sample is performed using an immunoassay or antibody method. In some embodiments, the detecting and/or measuring and/or quantifying the peptides in the digested sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for prognosing chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample provides a prognosis of chronic kidney disease in the subject. In some embodiments, the measuring the peptides in the digested sample is performed using an immunoassay or antibody method. In some embodiments, the measuring the peptides in the digested sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for treating a subject in need thereof, comprising: obtaining protein biomarker signature results for the subject, wherein the protein biomarker signature results provide a prognosis of chronic kidney disease in the subject; and treating the subject and/or selecting a treatment for and/or providing a treatment to the subject based on the prognosis of chronic kidney disease in the subject.

In various embodiments, the present invention provides a method for determining progression of chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample is indicative of progression of chronic kidney disease in the subject. In some embodiments, the measuring the peptides in the digested sample is performed using immunoassay or antibody method. In some embodiments, the measuring the peptides in the digested sample is performed using at least one technique selected from the group consisting of mass spectrometry, antibody method, antibodies, nucleic acid aptamer method, nucleic acid aptamers, immunoassay, ELISA, immunoprecipitation. SISCAPA, Western blot, and combinations thereof.

In various embodiments, the present invention provides a method for treating a subject in need thereof, comprising: receiving protein biomarker signature results for the subject, wherein the protein biomarker signature results are indicative of progression of chronic kidney disease in the subject; and treating the subject and/or selecting a treatment for and/or providing a treatment to the subject based on the progression of chronic kidney disease in the subject.

In various embodiments, the present invention provides a method for diagnosing chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample is indicative of chronic kidney disease in the subject. In some embodiments, the measuring the peptides in the digested sample is performed using immunoassay or antibody method. In some embodiments, the measuring the peptides in the digested sample is performed using at least one technique selected from the group consisting of mass spectrometry, antibody method, antibodies, nucleic acid aptamer method, nucleic acid aptamers, immunoassay, ELISA, immunoprecipitation. SISCAPA, Western blot, and combinations thereof.

In various embodiments, the present invention provides a method for treating a subject in need thereof, comprising: receiving protein biomarker signature results for the subject, providing a diagnosis of chronic kidney disease in the subject based on the protein biomarker signature results; and treating the subject and/or selecting a treatment for and/or providing a treatment to the subject based on the diagnosis.

In various embodiments, the present invention provides a method for assessing and/or determining the risk of developing chronic kidney disease in a subject, comprising:

obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, w herein a change in the protein biomarker signature from the subject relative to the protein biomarker signature from the reference sample is indicative of an increased risk of the subject developing chronic kidney disease. In some embodiments, the measuring the peptides in the digested sample is performed using immunoassay or antibody method. In some embodiments, the measuring the peptides in the digested sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for identifying and/or assessing chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, immunoassay, ELISA, immunoprecipitation, SISCAPA, Western blot, or combination thereof; correlating the peptides to one or more proteins so as to obtain a protein biomarker signature for the subject; comparing the protein biomarker signature from the subject to one or more reference protein biomarker signatures; and identifying and/or assessing chronic kidney disease in the subject based on the comparison. In some embodiments, the measuring the peptides in the digested sample is performed using immunoassay or antibody method. In some embodiments, the measuring the peptides in the digested sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for identifying protein biomarkers of chronic kidney disease in a subject, comprising: obtaining a sample from the subject, wherein the subject has chronic kidney disease; detecting and/or measuring and/or quantifying one or more proteins in the sample to obtain a protein biomarker signature for the subject, wherein the detecting and/or measuring and/or quantifying is performed using any one or more of mass spectrometry, ELISA, immunoprecipitation, SISCAPA, Western blot, or combination thereof; and comparing the protein biomarker signature from the subject to a protein biomarker signature from a reference sample; wherein protein biomarkers of chronic kidney disease are identified. In some embodiments, the detecting and/or measuring and/or quantifying the proteins in the sample is performed using an immunoassay or antibody method. In some embodiments, the detecting and/or measuring and/or quantifying the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for identifying protein biomarkers of chronic kidney disease in a subject, comprising: obtaining a sample from the subject, wherein the subject has chronic kidney disease; detecting and/or measuring and/or quantifying one or more proteins in the sample, wherein the detecting and/or measuring and/or quantifying is performed using any one or more of an ELISA, immunoprecipitation, SISCAPA, Western blot, mass spectrometry or combination thereof, wherein protein biomarkers of chronic kidney disease are identified. In some embodiments, the detecting and/or measuring and/or quantifying the proteins in the sample is performed using an immunoassay or antibody method. In some embodiments, the detecting and/or measuring and/or quantifying the proteins in the sample is performed using at least one technique selected from the group consisting of mass spectrometry, antibody method, antibodies, nucleic acid aptamer method, nucleic acid aptamers, immunoassay, ELISA, immunoprecipitation. SISCAPA, Western blot, and combinations thereof.

In various embodiments, the present invention provides a method for prognosing chronic kidney disease in a subject, comprising: obtaining a sample from the subject; measuring one or more proteins in the sample to obtain a protein biomarker signature for the subject, wherein the measuring is performed using any one or more of mass spectrometry, ELISA, immunoprecipitation, SISCAPA, Western blot, or combination thereof, comparing the protein biomarker signature from the subject to a protein biomarker signature from a reference sample, wherein a change in the protein biomarker signature from the subject relative to the protein biomarker signature from the reference sample provides a prognosis of chronic kidney disease in the subject. In some embodiments, measuring the proteins in the sample is performed using an immunoassay or antibody method. In some embodiments, measuring the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In some embodiments, the sample from the subject comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins listed in Table 1.

In some embodiments, the sample from the subject comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or all of the proteins listed in Table 6.

In various embodiments, the present invention provides a method for determining progression of chronic kidney disease in a subject, comprising: obtaining a sample from the subject; measuring one or more proteins in the sample to obtain a protein biomarker signature for the subject, wherein the measuring is performed using any one or more of mass spectrometry, ELISA, immunoprecipitation, SISCAPA, Western blot, or combination thereof; comparing the protein biomarker signature from the subject to a protein biomarker signature from a reference sample, wherein a change in the protein biomarker signature from the subject relative to the protein biomarker signature from the reference sample is indicative of progression of chronic kidney disease in the subject. In some embodiments, measuring the proteins in the sample is performed using an immunoassay or antibody method. In some embodiments, measuring the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In some embodiments, the sample from the subject comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins listed in Table 2.

In some embodiments, the sample from the subject comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or all of the proteins listed in Table 7.

In various embodiments, the present invention provides a method for diagnosing chronic kidney disease in a subject, comprising: obtaining a sample from the subject; measuring one or more proteins in the sample to obtain a protein biomarker signature for the subject, wherein the measuring is performed using any one or more of mass spectrometry, ELISA, immunoprecipitation, SISCAPA, Western blot, or combination thereof; and comparing the protein biomarker signature from the subject to a protein biomarker signature from a reference sample, wherein a change in the protein biomarker signature from the subject relative to the protein biomarker signature from the reference sample is indicative of chronic kidney disease in the subject. In some embodiments, measuring the proteins in the sample is performed using an immunoassay or antibody method. In some embodiments, measuring the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for assessing and/or determining the risk of developing chronic kidney disease in a subject, comprising: obtaining a sample from the subject; measuring one or more proteins in the sample to obtain a protein biomarker signature for the subject, wherein the measuring is performed using any one or more of mass spectrometry, ELISA, immunoprecipitation, SISCAPA, Western blot, or combination thereof; and comparing the protein biomarker signature from the subject to a protein biomarker signature from a reference sample, wherein a change in the protein biomarker signature from the subject relative to the protein biomarker signature from the reference sample is indicative of an increased risk of the subject developing chronic kidney disease. In some embodiments, measuring the proteins in the sample is performed using an immunoassay or antibody method. In some embodiments, measuring the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for identifying and/or assessing chronic kidney disease in a subject, comprising: obtaining a sample from the subject; measuring one or more proteins in the sample to obtain a protein biomarker signature for the subject, wherein the measuring is performed using any one or more of mass spectrometry, ELISA, immunoprecipitation, SISCAPA, Western blot, or combination thereof; comparing the protein biomarker signature from the subject to one or more reference protein biomarker signatures; and identifying and/or assessing chronic kidney disease in the subject based on the comparison. In some embodiments, measuring the proteins in the sample is performed using an antibody me immunoassay or antibody method. In some embodiments, the measuring the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for identifying protein biomarkers of chronic kidney disease in a subject, comprising: obtaining a sample from the subject, wherein the subject has chronic kidney disease; treating the sample with one or more proteases to obtain a digested sample comprising one or more peptides; detecting and/or measuring and/or quantifying the peptides in the digested sample, wherein the detecting and/or measuring and/or quantifying is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample; wherein protein biomarkers of chronic kidney disease are identified. In some embodiments, the one or more peptides are correlated to one or more proteins according to Table 1 and/or Table 2 and/or Table 6 and/or Table 7. In some embodiments, the subject is a human. In some embodiments, the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof. In some embodiments, the mass spectrometry is multiple reaction monitoring (MRM). In some embodiments, the one or more proteins and/or one or more peptides in the sample are modified. In some embodiments, the one or more proteins and/or one or more peptides in the sample are chemically modified. In some embodiments, the modification is any one or more of any one or more of phosphorylation, methylation, acetylation, o-GlycNacylation, s-nitrosylation, citrullination, sumoylation, ubiquitinylation, neddylation, methyglyoxylation, or a post-translational modification. In some embodiments, the method further comprises adding one or more internal standards to the sample. In some embodiments, the internal standard comprises one or more isotopically labeled peptides, one or more isotopically labeled proteins, or any combination thereof. In some embodiments, the reference sample is obtained from a control subject, wherein the control subject does not have the disease. In some embodiments, the detecting and/or measuring and/or quantifying the peptides in the digested sample is performed using an immunoassay or antibody method. In some embodiments, the detecting and/or measuring and/or quantifying the peptides in the digested sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for prognosing chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample provides a prognosis of chronic kidney disease in the subject. In some embodiments, the one or more peptides are correlated to one or more proteins according to Table 1 and/or Table 6. In some embodiments, the subject is a human. In some embodiments, the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof. In some embodiments, the mass spectrometry is multiple reaction monitoring (MRM). In some embodiments, the one or more proteins and/or one or more peptides in the sample are modified. In some embodiments, the one or more proteins and/or one or more peptides in the sample are chemically modified. In some embodiments, the modification is any one or more of any one or more of phosphorylation, methylation, acetylation, o-GlycNacylation, s-nitrosylation, citrullination, sumoylation, ubiquitinylation, neddylation, methyglyoxylation, or a post-translational modification. In some embodiments, the method further comprises adding one or more internal standards to the sample. In some embodiments, the internal standard comprises one or more isotopically labeled peptides, one or more isotopically labeled proteins, or any combination thereof. In some embodiments, the method further comprises treating the subject and/or selecting a treatment for and/or providing a treatment to the subject based on the prognosis. In some embodiments, the method further comprises assessing the efficacy of the treatment, comprising comparing the protein biomarker signature from the subject to a protein biomarker signature from a reference sample, wherein a change in the protein biomarker signature from the subject relative to the protein biomarker signature from the reference sample is indicative of the efficacy of the treatment. In some embodiments, the reference sample is obtained from a control subject, wherein the control subject does not have the disease. In some embodiments, the reference sample is obtained from the subject before the subject is treated for the disease. In some embodiments, the reference sample is from a subject that has been successfully treated for the disease. In some embodiments, measuring the peptides in the digested sample is performed using an immunoassay or antibody method. In some embodiments, the measuring the peptides in the digested sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for treating a subject in need thereof, comprising: obtaining protein biomarker signature results for the subject, wherein the protein biomarker signature results provide a prognosis of chronic kidney disease in the subject; and treating the subject and/or selecting a treatment for and/or providing a treatment to the subject based on the prognosis of chronic kidney disease in the subject.

In various embodiments, the present invention provides a method for determining progression of chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample is indicative of progression of chronic kidney disease in the subject. In some embodiments, the one or more peptides are correlated to one or more proteins according to Table 2 and/or Table 7. In some embodiments, the subject is a human. In some embodiments, the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof. In some embodiments, the mass spectrometry is multiple reaction monitoring (MRM). In some embodiments, the one or more proteins and/or one or more peptides in the sample are modified. In some embodiments, the one or more proteins and/or one or more peptides in the sample are chemically modified. In some embodiments, the modification is any one or more of any one or more of phosphorylation, methylation, acetylation, o-GlycNacylation, s-nitrosylation, citrullination, sumoylation, ubiquitinylation, neddylation, methyglyoxylation, or a post-translational modification. In some embodiments, the method further comprises adding one or more internal standards to the sample. In some embodiments, the internal standard comprises one or more isotopically labeled peptides, one or more isotopically labeled proteins, or any combination thereof. In some embodiments, the method further comprises treating the subject and/or selecting a treatment for and/or providing a treatment to the subject based on the progression of chronic kidney disease in the subject. In some embodiments, the method further comprises assessing the efficacy of the treatment, comprising comparing the protein biomarker signature from the subject to a protein biomarker signature from a reference sample, wherein a change in the protein biomarker signature from the subject relative to the protein biomarker signature from the reference sample is indicative of the efficacy of the treatment. In some embodiments, the reference sample is obtained from a control subject, wherein the control subject does not have the disease. In some embodiments, the reference sample is obtained from the subject before the subject is treated for the disease. In some embodiments, the reference sample is from a subject that has been successfully treated for the disease. In some embodiments, measuring the peptides in the digested sample is performed using an immunoassay or antibody method. In some embodiments, the measuring the peptides in the digested sample is performed using at least one technique selected from the group consisting of mass spectrometry, antibody method, antibodies, nucleic acid aptamer method, nucleic acid aptamers, immunoassay, ELISA, immunoprecipitation. SISCAPA, Western blot, and combinations thereof.

In various embodiments, the present invention provides a method for treating a subject in need thereof, comprising: receiving protein biomarker signature results for the subject, wherein the protein biomarker signature results are indicative of progression of chronic kidney disease in the subject; and treating the subject and/or selecting a treatment for and/or providing a treatment to the subject based on the progression of chronic kidney disease in the subject.

In various embodiments, the present invention provides a method for diagnosing chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample is indicative of chronic kidney disease in the subject. In some embodiments, the one or more peptides are correlated to one or more proteins according to Table 1 and/or Table 2 and/or Table 6 and/or Table 7. In some embodiments, the subject is a human. In some embodiments, the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof. In some embodiments, the mass spectrometry is multiple reaction monitoring (MRM). In some embodiments, the one or more proteins and/or one or more peptides in the sample are modified. In some embodiments, the one or more proteins and/or one or more peptides in the sample are chemically modified. In some embodiments, the modification is any one or more of any one or more of phosphorylation, methylation, acetylation, o-GlycNacylation, s-nitrosylation, citrullination, sumoylation, ubiquitinylation, neddylation, methyglyoxylation, or a post-translational modification. In some embodiments, the method further comprises adding one or more internal standards to the sample. In some embodiments, the internal standard comprises one or more isotopically labeled peptides, one or more isotopically labeled proteins, or any combination thereof. In some embodiments, the method further comprises treating the subject and/or selecting a treatment for and/or providing a treatment to the subject based on the diagnosis. In some embodiments, the method further comprises assessing the efficacy of the treatment, comprising comparing the protein biomarker signature from the subject to a protein biomarker signature from a reference sample, wherein a change in the protein biomarker signature from the subject relative to the protein biomarker signature from the reference sample is indicative of the efficacy of the treatment. In some embodiments, the reference sample is obtained from a control subject, wherein the control subject does not have the disease. In some embodiments, the reference sample is obtained from the subject before the subject is treated for the disease. In some embodiments, the reference sample is from a subject that has been successfully treated for the disease. In some embodiments, measuring the peptides in the digested sample is performed using an immunoassay or antibody method. In some embodiments, the measuring the peptides in the digested sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for treating a subject in need thereof, comprising: receiving protein biomarker signature results for the subject, providing a diagnosis of chronic kidney disease in the subject based on the protein biomarker signature results; and treating the subject and/or selecting a treatment for and/or providing a treatment to the subject based on the diagnosis.

In various embodiments, the present invention provides a method for assessing and/or determining the risk of developing chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof, correlating the peptides to one or more proteins so as to obtain a protein biomarker signature for the subject; and comparing the protein biomarker signature from the subject to a protein biomarker signature from a reference sample, w herein a change in the protein biomarker signature from the subject relative to the protein biomarker signature from the reference sample is indicative of an increased risk of the subject developing chronic kidney disease. In some embodiments, the one or more peptides are correlated to one or more proteins according to Table 1 and/or Table 2 and/or Table 6 and/or Table 7. In some embodiments, measuring the peptides in the digested sample is performed using an immunoassay or antibody method. In some embodiments, the measuring the peptides in the digested sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for identifying and/or assessing chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, immunoassay, ELISA, immunoprecipitation, SISCAPA, Western blot, or combination thereof; correlating the peptides to one or more proteins so as to obtain a protein biomarker signature for the subject; comparing the protein biomarker signature from the subject to one or more reference protein biomarker signatures; and identifying and/or assessing chronic kidney disease in the subject based on the comparison. In some embodiments, the one or more reference protein biomarker signatures are from one or more diseased subjects having chronic kidney disease. In some embodiments, the one or more reference protein biomarker signatures are from one or more healthy subjects. In some embodiments, the method further comprises treating the subject and/or selecting a treatment and/or providing a treatment and/or selecting a preventative treatment and/or providing a preventative treatment for the subject. In some embodiments, the one or more peptides are correlated to one or more proteins according to Table 1 and/or Table 2 and/or Table 6 and/or Table 7. In some embodiments, measuring the peptides in the digested sample is performed using an immunoassay or antibody method. In some embodiments, the measuring the peptides in the digested sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for identifying protein biomarkers of chronic kidney disease in a subject, comprising: obtaining a sample from the subject, wherein the subject has chronic kidney disease; detecting and/or measuring and/or quantifying one or more proteins in the sample to obtain a protein biomarker signature for the subject, wherein the detecting and/or measuring and/or quantifying is performed using any one or more of mass spectrometry, ELISA, immunoprecipitation, SISCAPA, Western blot, or combination thereof; and comparing the protein biomarker signature from the subject to a protein biomarker signature from a reference sample; wherein protein biomarkers of chronic kidney disease are identified. In some embodiments, the detecting and/or measuring and/or quantifying the proteins in the sample is performed using an immunoassay or antibody method. In some embodiments, the detecting and/or measuring and/or quantifying the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for identifying protein biomarkers of chronic kidney disease in a subject, comprising: obtaining a sample from the subject, wherein the subject has chronic kidney disease; detecting and/or measuring and/or quantifying one or more proteins in the sample, wherein the detecting and/or measuring and/or quantifying is performed using any one or more of an ELISA, immunoprecipitation, SISCAPA, Western blot, mass spectrometry or combination thereof, wherein protein biomarkers of chronic kidney disease are identified. In some embodiments, the detecting and/or measuring and/or quantifying the proteins in the sample is performed using an immunoassay or antibody method. In some embodiments, the detecting and/or measuring and/or quantifying the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for prognosing chronic kidney disease in a subject, comprising: obtaining a sample from the subject; measuring one or more proteins in the sample to obtain a protein biomarker signature for the subject, wherein the measuring is performed using any one or more of mass spectrometry, ELISA, immunoprecipitation, SISCAPA, Western blot, or combination thereof; comparing the protein biomarker signature from the subject to a protein biomarker signature from a reference sample, wherein a change in the protein biomarker signature from the subject relative to the protein biomarker signature from the reference sample provides a prognosis of chronic kidney disease in the subject. In some embodiments, measuring the proteins in the sample is performed using an immunoassay or antibody method. In some embodiments, the measuring the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for determining progression of chronic kidney disease in a subject, comprising: obtaining a sample from the subject; measuring one or more proteins in the sample to obtain a protein biomarker signature for the subject, wherein the measuring is performed using any one or more of mass spectrometry, ELISA, immunoprecipitation, SISCAPA, Western blot, or combination thereof; comparing the protein biomarker signature from the subject to a protein biomarker signature from a reference sample, wherein a change in the protein biomarker signature from the subject relative to the protein biomarker signature from the reference sample is indicative of progression of chronic kidney disease in the subject. In some embodiments, measuring the proteins in the sample is performed using an immunoassay or antibody method. In some embodiments, the measuring the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for diagnosing chronic kidney disease in a subject, comprising: obtaining a sample from the subject; measuring one or more proteins in the sample to obtain a protein biomarker signature for the subject, wherein the measuring is performed using any one or more of mass spectrometry, ELISA, immunoprecipitation, SISCAPA, Western blot, or combination thereof; and comparing the protein biomarker signature from the subject to a protein biomarker signature from a reference sample, wherein a change in the protein biomarker signature from the subject relative to the protein biomarker signature from the reference sample is indicative of chronic kidney disease in the subject. In some embodiments, measuring the proteins in the sample is performed using an immunoassay or antibody method. In some embodiments, the measuring the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for assessing and/or determining the risk of developing chronic kidney disease in a subject, comprising: obtaining a sample from the subject; measuring one or more proteins in the sample to obtain a protein biomarker signature for the subject, wherein the measuring is performed using any one or more of mass spectrometry, ELISA, immunoprecipitation, SISCAPA, Western blot, or combination thereof; and comparing the protein biomarker signature from the subject to a protein biomarker signature from a reference sample, wherein a change in the protein biomarker signature from the subject relative to the protein biomarker signature from the reference sample is indicative of an increased risk of the subject developing chronic kidney disease. In some embodiments, measuring the proteins in the sample is performed using an immunoassay or antibody method. In some embodiments, the measuring the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for identifying and/or assessing chronic kidney disease in a subject, comprising: obtaining a sample from the subject; measuring one or more proteins in the sample to obtain a protein biomarker signature for the subject, wherein the measuring is performed using any one or more of mass spectrometry, ELISA, immunoprecipitation, SISCAPA, Western blot, or combination thereof; comparing the protein biomarker signature from the subject to one or more reference protein biomarker signatures; and identifying and/or assessing chronic kidney disease in the subject based on the comparison. In some embodiments, measuring the proteins in the sample is performed using an immunoassay or antibody method. In some embodiments, the measuring the proteins in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for prognosing and treating chronic kidney disease in a subject, comprising: i) obtaining a sample from the subject, ii) detecting at least one protein in the sample by at least one technique selected from the group consisting of mass spectrometry, antibody method, nucleic acid aptamer method, immunoassay, ELISA, immunoprecipitation, SISCAPA, Western blot, and combinations thereof, wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1 (UniProt Accession No. Q8TEA8), Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; iii) determining an amount of the protein in the sample from the subject; iv) constructing a protein biomarker signature for the subject, wherein the biomarker signature comprises the amount of the protein in the sample from the subject; v) comparing the amount of the protein in the sample from the subject to an amount of the protein in a reference sample, wherein a change in the amount of the protein in the sample from the subject relative to the amount of the protein in the reference sample is a prognosis of chronic kidney disease in the subject; and vi) administering a treatment to the subject. In some embodiments, the determining an amount of the protein in the sample from the subject is by at least one technique selected from the group consisting of mass spectrometry, antibody method, nucleic acid aptamer method, immunoassay, ELISA, immunoprecipitation, SISCAPA, Western blot, and combinations thereof. In some embodiments, detecting at least one protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof. In some embodiments, the determining an amount of the protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for prognosing and treating chronic kidney disease in a subject, comprising: i) obtaining a sample from the subject, ii) detecting and determining an amount of at least one protein in the sample by at least one technique selected from the group consisting of mass spectrometry, antibody method, nucleic acid aptamer method, immunoassay, ELISA, immunoprecipitation, SISCAPA, Western blot, and combination thereof; wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1 (UniProt Accession No. Q8TEA8). Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; iii) constructing a protein biomarker signature for the subject, wherein the biomarker signature comprises the amount of the protein in the sample from the subject; iv) comparing the amount of the protein in the sample from the subject to an amount of the protein in a reference sample, wherein a change in the amount of the protein in the sample from the subject relative to the amount of the protein in the reference sample is a prognosis of chronic kidney disease in the subject; and v) administering a treatment to the subject. In some embodiments, detecting at least one protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof. In some embodiments, the determining an amount of the protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof. In some embodiments, detecting and determining an amount of at least one protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for determining progression of and treating chronic kidney disease in a subject, comprising: i) obtaining a sample from the subject, ii) detecting at least one protein in the sample by at least one technique selected from the group consisting of mass spectrometry, antibody method, nucleic acid aptamer method, immunoassay, ELISA, immunoprecipitation, SISCAPA, Western blot, and combinations thereof; wherein the protein is selected from the group consisting of Uteroglobin (UniProt Accession No. P11684), Putative sodium-coupled neutral amino acid transporter 10 (UniProt Accession No. Q9HBR0), Protein AMBP (precursors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859), Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; iii) determining an amount of the protein in the sample from the subject; iv) constructing a protein biomarker signature for the subject, wherein the biomarker signature comprises the amount of the protein in the sample from the subject; v) comparing the amount of the protein in the sample from the subject to an amount of the protein in a reference sample, wherein a change in the amount of the protein in the sample from the subject relative to the amount of the protein in the reference sample is indicative of progression of chronic kidney disease in the subject; and vi) administering a treatment to the subject. In some embodiments, the determining an amount of the protein in the sample from the subject is by at least one technique selected from the group consisting of mass spectrometry, antibody method, nucleic acid aptamer method, immunoassay, ELISA, immunoprecipitation, SISCAPA, Western blot, and combinations thereof. In some embodiments, detecting at least one protein in the sample is performed using at least one technique selected from the group consisting of mass spectrometry, antibody method, antibodies, nucleic acid aptamer method, nucleic acid aptamers, immunoassay, ELISA, immunoprecipitation. SISCAPA, Western blot, and combinations thereof. In some embodiments, the determining an amount of the protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for determining progression of and treating chronic kidney disease in a subject, comprising: i) obtaining a sample from the subject, ii) detecting and determining an amount of at least one protein in the sample by at least one technique selected from the group consisting of mass spectrometry, antibody method, nucleic acid aptamer method, immunoassay, ELISA, immunoprecipitation, SISCAPA, Western blot, and combinations thereof; wherein the protein is selected from the group consisting of Uteroglobin (UniProt Accession No. P11684), Putative sodium-coupled neutral amino acid transporter 10 (UniProt Accession No. Q9HBR0), Protein AMBP (precursors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859). Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; iii) constructing a protein biomarker signature for the subject, wherein the biomarker signature comprises the amount of the protein in the sample from the subject; iv) comparing the amount of the protein in the sample from the subject to an amount of the protein in a reference sample, wherein a change in the amount of the protein in the sample from the subject relative to the amount of the protein in the reference sample is indicative of progression of chronic kidney disease in the subject; and v) administering a treatment to the subject. In some embodiments, detecting at least one protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof. In some embodiments, the determining an amount of the protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof. In some embodiments, detecting and determining an amount of at least one protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for prognosing and treating chronic kidney disease in a subject, comprising: i) obtaining a sample from the subject, wherein the sample comprises at least one protein, and wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96). Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1 (UniProt Accession No. Q8TEA8), Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; ii) identifying the protein and determining an amount of the protein in the sample from the subject by at least one technique selected from the group consisting of mass spectrometry, antibody method, nucleic acid aptamer method, immunoassay, ELISA, immunoprecipitation, SISCAPA, Western blot, or combination thereof; iii) constructing a protein biomarker signature for the subject, wherein the biomarker signature comprises the amount of the protein in the sample from the subject; iv) comparing the amount of the protein in the sample from the subject to an amount of the protein in a reference sample, wherein a change in the amount of the protein in the sample from the subject relative to the amount of the protein in the reference sample is a prognosis of chronic kidney disease in the subject; and v) administering a treatment to the subject. In some embodiments, identifying the protein and determining an amount of the protein in the sample from the subject is by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for determining progression of and treating chronic kidney disease in a subject, comprising: i) obtaining a sample from the subject, wherein the sample comprises at least one protein, and wherein the protein is selected from the group consisting of Uteroglobin (UniProt Accession No. P11684), Putative sodium-coupled neutral amino acid transporter 10 (UniProt Accession No. Q9HBR0), Protein AMBP (precusors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859), Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; ii) identifying the protein and determining an amount of the protein in the sample from the subject by at least one technique selected from the group consisting of mass spectrometry, antibody method, nucleic acid aptamer method, immunoassay, ELISA, immunoprecipitation, SISCAPA, Western blot, or combination thereof; iii) constructing a protein biomarker signature for the subject, wherein the biomarker signature comprises the amount of the protein in the sample from the subject; and iv) comparing the amount of the protein in the sample from the subject to an amount of the protein in a reference sample, wherein a change in the amount of the protein in the sample from the subject relative to the amount of the protein in the reference sample is indicative of progression of chronic kidney disease in the subject; and v) administering a treatment to the subject. In some embodiments, identifying the protein and determining an amount of the protein in the sample from the subject is by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments the present invention provides a method for prognosing chronic kidney disease in a subject, comprising: i) obtaining a sample from the subject, wherein the sample comprises at least one protein, and wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1 (UniProt Accession No. Q8TEA8), Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; ii) identifying the protein and determining an amount of the protein in the sample from the subject by at least one technique selected from the group consisting of mass spectrometry, antibody method, nucleic acid aptamer method, immunoassay, ELISA, immunoprecipitation. SISCAPA, Western blot, or combination thereof; iii) constructing a protein biomarker signature for the subject, wherein the biomarker signature comprises the amount of the protein in the sample from the subject; and iv) comparing the amount of the protein in the sample from the subject to an amount of the protein in a reference sample, wherein a change in the amount of the protein in the sample from the subject relative to the amount of the protein in the reference sample is a prognosis of chronic kidney disease in the subject. In some embodiments, the mass spectrometry is selected from the group consisting of SRM, MRM, PRM, DDA, DIA, LC-MS, LC-MS/MS, LC-SRM-MS, LC-MRM-MS, LC-PRM-MS, LC-DDA-MS, LC-DIA-MS, and combinations thereof. In some embodiments, the subject is human. In some embodiments, the sample is plasma. In some embodiments, the reference sample is obtained from a control subject, wherein the control subject does not have chronic kidney disease. In some embodiments, the reference sample is obtained from the subject before the subject is treated for chronic kidney disease. In some embodiments, the reference sample is from a subject that has been successfully treated for chronic kidney disease. In some embodiments, the method further comprises administering a treatment to the subject. In some embodiments, the method further comprises administering a treatment to the subject; obtaining a post-treatment sample from the subject, wherein the post-treatment sample comprises at least one protein according to the method; identifying the protein in the post-treatment sample from the subject according to the method; determining an amount of the protein in the post-treatment sample from the subject according to the method; and comparing the amount of the protein in the post-treatment sample from the subject to an amount of the protein in a reference sample, wherein a change in the amount of the protein in the post-treatment sample from the subject relative to the amount of the protein in the reference sample is indicative of the efficacy of the treatment. In some embodiments, the reference sample is obtained from a control subject, wherein the control subject does not have chronic kidney disease. In some embodiments, the reference sample is obtained from the subject before the subject is treated for chronic kidney disease. In some embodiments, the reference sample is from a subject that has been successfully treated for chronic kidney disease. In some embodiments, identifying the protein and determining an amount of the protein in the sample from the subject is by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In some embodiments, the sample from the subject comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins listed in Table 1.

In some embodiments, the sample from the subject comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or all of the proteins listed in Table 6.

In various embodiments, the present invention provides a method for determining progression of chronic kidney disease in a subject, comprising: i) obtaining a sample from the subject, wherein the sample comprises at least one protein, and wherein the protein is selected from the group consisting of Uteroglobin (UniProt Accession No. P11684), Putative sodium-coupled neutral amino acid transporter 10 (UniProt Accession No. Q9HBR0), Protein AMBP (precursors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859), Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; ii) identifying the protein and determining an amount of the protein in the sample from the subject by at least one technique selected from the group consisting of mass spectrometry, antibody method, nucleic acid aptamer method, immunoassay, ELISA, immunoprecipitation, SIS-CAPA, Western blot, or combination thereof; iii) constructing a protein biomarker signature for the subject, wherein the biomarker signature comprises the amount of the protein in the sample from the subject; and iv) comparing the amount of the protein in the sample from the subject to an amount of the protein in a reference sample, wherein a change in the amount of the protein in the sample from the subject relative to the amount of the protein in the reference sample is indicative of progression of chronic kidney disease in the subject. In some embodiments, the mass spectrometry is selected from the group consisting of SRM, MRM, PRM, DDA, DIA, LC-MS, LC-MS/MS, LC-SRM-MS, LC-MRM-MS, LC-PRM-MS, LC-DDA-MS, LC-DIA-MS, and combinations thereof. In some embodiments, the subject is human. In some embodiments, the sample is plasma. In some embodiments, the reference sample is obtained from a control subject, wherein the control subject does not have chronic kidney disease. In some embodiments, the reference sample is obtained from the subject before the subject is treated for chronic kidney disease. In some embodiments, the reference sample is from a subject that has been successfully treated for chronic kidney disease. In some embodiments, the method further comprises administering a treatment to the subject. In some embodiments, the method further comprises administering a treatment to the subject; obtaining a post-treatment sample from the subject, wherein the post-treatment sample comprises at least one protein according to the method; identifying the protein in the post-treatment sample from the subject according to the method; determining an amount of the protein in the post-treatment sample from the subject according to the method; and comparing the amount of the protein in the post-treatment sample from the subject to an amount of the protein in a reference sample, wherein a change in the amount of the protein in the post-treatment sample from the subject relative to the amount of the protein in the reference sample is indicative of the efficacy of the treatment. In some embodiments, the reference sample is obtained from a control subject, wherein the control subject does not have chronic kidney disease. In some embodiments, the reference sample is obtained from the subject before the subject is treated for chronic kidney disease. In some embodiments, the reference sample is from a subject that has been successfully treated for chronic kidney disease. In some embodiments, identifying the protein and determining an amount of the protein in the sample from the subject is by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In some embodiments, the sample from the subject comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins listed in Table 2.

In some embodiments, the sample from the subject comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or all of the proteins listed in Table 7.

In various embodiments, the present invention provides a method for prognosing chronic kidney disease in a subject, comprising: i) obtaining a sample from the subject, ii) detecting at least one protein in the sample by at least one technique selected from the group consisting of mass spectrometry, antibody method, nucleic acid aptamer method, immunoassay, ELISA, immunoprecipitation, SISCAPA, Western blot, and combinations thereof; wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1 (UniProt Accession No. Q8TEA8), Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; iii) determining an amount of the protein in the sample from the subject; iv) constructing a protein biomarker signature for the subject, wherein the biomarker signature comprises the amount of the protein in the sample from the subject, and v) comparing the amount of the protein in the sample from the subject to an amount of the protein in a reference sample, wherein a change in the amount of the protein in the sample from the subject relative to the amount of the protein in the reference sample is a prognosis of chronic kidney disease in the subject. In some embodiments, the determining an amount of the protein in the sample from the subject is by at least one technique selected from the group consisting of mass spectrometry, antibody method, nucleic acid aptamer method, immunoassay, ELISA, immunoprecipitation, SISCAPA, Western blot, and combinations thereof. In some embodiments, detecting at least one protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof. In some embodiments, the determining an amount of the protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for prognosing chronic kidney disease in a subject, comprising: i) obtaining a sample from the subject, ii) detecting and determining an amount of at least one protein in the sample by at least one technique selected from the group consisting of mass spectrometry, antibody method, nucleic acid aptamer method, immunoassay, ELISA, immunoprecipitation, SISCAPA, Western blot, and combinations thereof; wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1 (UniProt Accession No. Q8TEA8), Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; iii) constructing a protein biomarker signature for the subject, wherein the biomarker signature comprises the amount of the protein in the sample from the subject, and iv) comparing the amount of the protein in the sample from the subject to an amount of the protein in a reference sample, wherein a change in the amount of the protein in the sample from the subject relative to the amount of the protein in the reference sample is a prognosis of chronic kidney disease in the subject. In some embodiments, detecting at least one protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof. In some embodiments, the determining an amount of the protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof. In some embodiments, detecting and determining an amount of at least one protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins are detected in the sample from the subject.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins are detected and/or an amount determined in the sample from the subject.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins from Table 1 are detected in the sample from the subject.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins from Table 1 are detected and/or an amount determined in the sample from the subject.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or all of the proteins from Table 6 are detected in the sample from the subject.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or all of the proteins from Table 6 are detected and/or an amount determined in the sample from the subject.

In various embodiments, the present invention provides a method for determining progression of chronic kidney disease in a subject, comprising: i) obtaining a sample from the subject, ii) detecting at least one protein in the sample by at least one technique selected from the group consisting of mass spectrometry, antibody method, nucleic acid aptamer method, immunoassay, ELISA, immunoprecipitation, SISCAPA, Western blot, and combinations thereof, wherein the protein is selected from the group consisting of Uteroglobin (UniProt Accession No. P11684), Putative sodium-coupled neutral amino acid transporter 10 (UniProt Accession No. Q9HBR0), Protein AMBP (precusors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859), Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; iii) determining an amount of the protein in the sample from the subject; iv) constructing a protein biomarker signature for the subject, wherein the biomarker signature comprises the amount of the protein in the sample from the subject; and v) comparing the amount of the protein in the sample from the subject to an amount of the protein in a reference sample, wherein a change in the amount of the protein in the sample from the subject relative to the amount of the protein in the reference sample is indicative of progression of chronic kidney disease in the subject. In some embodiments, the determining an amount of the protein in the sample from the subject is by at least one technique selected from the group consisting of mass spectrometry, antibody method, nucleic acid aptamer method, immunoassay, ELISA, immunoprecipitation, SISCAPA, Western blot, and combinations thereof. In some embodiments, detecting at least one protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof. In some embodiments, the determining an amount of the protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a method for determining progression of chronic kidney disease in a subject, comprising: i) obtaining a sample from the subject, ii) detecting and determining an amount of at least one protein in the sample by at least one technique selected from the group consisting of mass spectrometry, antibody method, nucleic acid aptamer method, immunoassay, ELISA, immunoprecipitation, SISCAPA, Western blot, and combinations thereof; wherein the protein is selected from the group consisting of Uteroglobin (UniProt Accession No. P11684), Putative sodium-coupled neutral amino acid transporter 10 (UniProt Accession No. Q9HBR0), Protein AMBP (precusors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859). Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; iii) determining an amount of the protein in the sample from the subject; iv) constructing a protein biomarker signature for the subject, wherein the biomarker signature comprises the amount of the protein in the sample from the subject; and v) comparing the amount of the protein in the sample from the subject to an amount of the protein in a reference sample, wherein a change in the amount of the protein in the sample from the subject relative to the amount of the protein in the reference sample is indicative of progression of chronic kidney disease in the subject. In some embodiments, detecting at least one protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof. In some embodiments, the determining an amount of the protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof. In some embodiments, detecting and determining an amount of at least one protein in the sample is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins are detected in the sample from the subject.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins are detected and/or determined in the sample from the subject.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins from Table 2 are detected in the sample from the subject.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the proteins from Table 2 are detected and/or determined in the sample from the subject.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or all of the proteins from Table 7 are detected in the sample from the subject.

In some embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or all of the proteins from Table 7 are detected and/or determined in the sample from the subject.

In some embodiments, the reference sample is a post-treatment reference sample.

In some embodiments, the proteins in Table 1 are markers for prognosing chronic kidney disease. In some embodiments, the proteins in Table 6 are markers for prognosing chronic kidney disease.

In some embodiments, the proteins in Table 2 are markers for determining progression of chronic kidney disease. In some embodiments, the proteins in Table 7 are markers for determining progression of chronic kidney disease.

In some embodiments, an antibody method is selected from the group consisting of a polyclonal antibody method, monoclonal antibody method, synthetic antibody method, single antibody method, sandwich based antibody method, and combinations thereof.

In some embodiments, an antibody method uses antibodies as capture reagents. In some embodiments, an antibody method uses antibodies as peptide capture reagents. In some embodiments, an antibody method uses antibodies as protein capture reagents.

In some embodiments, a nucleic acid aptamer method uses nucleic acid aptamers as capture reagents. In some embodiments, a nucleic acid aptamer method uses nucleic acid aptamers as peptide capture reagents. In some embodiments, a nucleic acid aptamer method uses nucleic acid aptamers as protein capture reagents.

In some embodiments, a change in the amount of the protein in the sample from the subject relative to the amount of the protein in the reference sample is an increase in the amount of the protein in the sample from the subject relative to the amount of the protein in the reference sample. In some embodiments, a change in the amount of the protein in the sample from the subject relative to the amount of the protein in the reference sample is characterized by an increase in the amount of the protein in the sample from the subject relative to the amount of the protein in the reference sample. In some embodiments, a difference in the amount of the protein in the sample from the subject relative to the amount of the protein in the reference sample is characterized by an increase in the amount of the protein in the sample from the subject relative to the amount of the protein in the reference sample.

In some embodiments, a change in the amount of the protein in the sample from the subject relative to the amount of the protein in the reference sample is a decrease in the amount of the protein in the sample from the subject relative to the amount of the protein in the reference sample. In some embodiments, a change in the amount of the protein in the sample from the subject relative to the amount of the protein in the reference sample is characterized by a decrease in the amount of the protein in the sample from the subject relative to the amount of the protein in the reference sample. In some embodiments, a difference in the amount of the protein in the sample from the subject relative to the amount of the protein in the reference sample is characterized by a decrease in the amount of the protein in the sample from the subject relative to the amount of the protein in the reference sample.

In some embodiments, comparing the amount of the protein in the sample from the subject to an amount of the protein in a reference sample, wherein a difference in the amount of the protein in the sample from the subject relative to the amount of the protein in the reference sample is a prognosis of chronic kidney disease in the subject.

In some embodiments, comparing the amount of the protein in the sample from the subject to an amount of the protein in a reference sample, wherein a difference in the amount of the protein in the sample from the subject relative to the amount of the protein in the reference sample is indicative of progression of chronic kidney disease in the subject.

In various embodiments, the present invention provides a method for prognosing chronic kidney disease in a subject, comprising: i) obtaining a sample from the subject; ii) detecting and determining an amount of at least one protein in the sample by at least one technique selected from the group consisting of mass spectrometry, antibody method, nucleic acid aptamer method, immunoassay, ELISA, immunoprecipitation, SISCAPA, Western blot, and combinations thereof; wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1 (UniProt Accession No. Q8TEA8), Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; iii) constructing a protein biomarker signature for the subject, wherein the biomarker signature comprises the amount of the protein in the sample from the subject; and iv) comparing the amount of the protein in the sample from the subject to an amount of the protein in a reference sample, wherein a difference in the amount of the protein in the sample from the subject relative to the amount of the protein in the reference sample is a prognosis of chronic kidney disease in the subject.

In various embodiments, the present invention provides a method for determining progression of chronic kidney disease in a subject, comprising: i) obtaining a sample from the subject; ii) detecting and determining an amount of at least one protein in the sample by at least one technique selected from the group consisting of mass spectrometry, antibody method, nucleic acid aptamer method, immunoassay, ELISA, immunoprecipitation, SISCAPA, Western blot, and combinations thereof; wherein the protein is selected from the group consisting of Uteroglobin (UniProt Accession No. P11684), Putative sodium-coupled neutral amino acid transporter 10 (UniProt Accession No. Q9HBR0), Protein AMBP (precusors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859), Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; iii) constructing a protein biomarker signature for the subject, wherein the biomarker signature comprises the amount of the protein in the sample from the subject; and iv) comparing the amount of the protein in the sample from the subject to an amount of the protein in a reference sample, wherein a difference in the amount of the protein in the sample from the subject relative to the amount of the protein in the reference sample is indicative of progression of chronic kidney disease in the subject.

A method for prognosing chronic kidney disease in a subject, comprising: i) obtaining a sample from the subject; ii) detecting the presence of at least one protein in the sample by at least one technique selected from the group consisting of mass spectrometry, antibody method, nucleic acid aptamer method, immunoassay, ELISA, immunoprecipitation, SISCAPA, Western blot, and combinations thereof; wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1 (UniProt Accession No. Q8TEA8), Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; iii) constructing a protein biomarker signature for the subject, wherein the biomarker signature comprises the at least one protein detected in the sample from the subject; and iv) comparing the protein biomarker signature for the subject to a protein biomarker signature from a reference sample, wherein a difference in the protein biomarker signature from the subject relative to the biomarker signature from the reference sample is a prognosis of chronic kidney disease in the subject.

A method for determining progression of chronic kidney disease in a subject, comprising: i) obtaining a sample from the subject; ii) detecting the presence of at least one protein in the sample by at least one technique selected from the group consisting of mass spectrometry, antibody method, nucleic acid aptamer method, immunoassay, ELISA, immunoprecipitation, SISCAPA, Western blot, and combinations thereof; wherein the protein is selected from the group consisting of Uteroglobin (UniProt Accession No. P11684), Putative sodium-coupled neutral amino acid transporter 10 (UniProt Accession No. Q9HBR0), Protein AMBP (precusors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859), Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; iii) constructing a protein biomarker signature for the subject, wherein the biomarker signature comprises the at least one protein detected in the sample from the subject; and iv) comparing the protein biomarker signature for the subject to a protein biomarker signature from a reference sample, wherein a difference in the protein biomarker signature from the subject relative to the biomarker signature from the reference sample is indicative of progression of chronic kidney disease in the subject.

In some embodiments, the mass spectrometer is a triple quadrupole mass spectrometer. In some embodiments the mass spectrometer is a Triple-Time Of Flight (Triple-TOF) mass spectrometer configured for SWATH or a Q-Exactive mass spectrometer (Thermo Scientific), or any instrument with sufficiently high scan speed and a quadrupole mass filter to perform data independent acquisition. Examples of triple quadrupole mass spectrometers (TQMS) that can perform MRM/SRM/SIM include but are not limited to: QTRAP® 6500 and 5500 System (Sciex); Triple QTriple Quad 6500 System (Sciex); Agilent 6400 Series Triple Quadrupole LC/MS systems; Thermo Scientific™ TSQ™ Triple Quadrupole system; quadrupole time-of-flight (QTOF) mass spectrometers, or hybrid quadrupole-orbitrap (QOrbitrap) mass spectrometers to carry out the peptides/proteins quantitation. Examples of quadrupole time-of-flight (QTOF) mass spectrometers include but are not limited to: TripleTOF® 6600 or 5600 System (Sciex); X500R QTOF System (Sciex); 6500 Series Accurate-Mass Quadrupole Time-of-Flight (Q-TOF) (Agilent); or Xevo G2-XS QTof Quadrupole Time-of-Flight Mass Spectrometry (Waters). Examples of hybrid quadrupole-orbitrap (QObitrap) mass spectrometers include but are not limited to: Q Exactive™ Hybrid Quadrupole-Orbitrap Mass Spectrometer (the Thermo Scientific); or Orbitrap Fusion™ Tribrid™ (the Thermo Scientific).

In some embodiments, the mass spectrometry technique is tandem mass spectrometry (MS/MS). In some embodiments, the mass spectrometry technique is liquid chromatography-tandom mass spectrometry (LC-MS/MS). In some embodiments, the mass spectrometry technique is liquid chromatography-selected reaction monitoring-mass spectrometry (LC-SRM-MS). In some embodiments, the mass spectrometry technique is liquid chromatography-multiple reaction monitoring-mass spectrometry (LC-MRM-MS). In some embodiments, the mass spectrometry technique is selected reaction monitoring. In some embodiments, the mass spectrometry technique is multiple reaction monitoring (MRM). In some embodiments, the mass spectrometry technique is parallel reaction monitoring (PRM). In some embodiments, the mass spectrometry is selected from the group consisting of selected reaction monitoring (SRM), multiple reaction monitoring (MRM), parallel reaction monitoring (PRM), data dependent acquisition (DDA), data independent acquisition (DIA), liquid chromatography-mass spectrometry (LC-MS), liquid chromatography-tandom mass spectrometry (LC-MS/MS), liquid chromatography-selected reaction monitoring-mass spectrometry (LC-SRM-MS), liquid chromatography-multiple reaction monitoring-mass spectrometry (LC-MRM-MS), liquid chromatography-parallel reaction monitoring (LC-PRM-MS), liquid chromatography-data dependent acquisition-mass spectrometry (LC-DDA-MS), liquid chromatography-data independent acquisition-mass spectrometry (LC-DIA-MS), and combinations thereof.

In various embodiments, the samples are biological samples or complex biological samples. In exemplary embodiments, the complex samples include, but are not limited to tissues and/or tissue extracts, and/or cells.

In various embodiments, the peptides are derived by proteolysis or chemical cleavage of the polypeptide or protein. In an embodiment, a protease is utilized to cleave the polypeptide or protein into peptides. For example, the protease is trypsin. In additional embodiments, proteases or cleavage agents may be used including but not limited to trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof. In some embodiments, the protease is trypsin.

In some embodiments, the proteins can be measured as intact mass using a mass spectrometer. In some embodiments, no digestion of the proteins is required prior to mass spectrometry.

In some embodiments, the proteins can be measured as intact mass using an immunoassay. In some embodiments, no digestion of the proteins is required prior to performing an immunoassay.

In some embodiments, the proteins can be measured as intact mass using a mass spectrometer, and immunoassay, or combination thereof. In some embodiments, no digestion of the proteins is required prior to mass spectrometry, immunoassay, or combination thereof.

In some embodiments, the proteins can be measured as intact mass using antibody methods. In some embodiments, no digestion of the proteins is required prior to using the antibody methods.

In some embodiments, the proteins can be measured as intact mass using nucleic acid aptamer methods. In some embodiments, no digestion of the proteins is required prior to using the nucleic acid aptamer methods.

In various other embodiments, a list of candidate peptides to be targeted for detection on the analytical instrument is generated by modeling protein cleavage. In exemplary embodiments, a list of candidate peptides to be targeted for detection on the analytical instrument is generated by modeling trypsin digestion of the polypeptide or protein. In some embodiments, the list of candidate peptides is narrowed by eliminating peptides that, for example, cannot be detected on the analytical instrument. In some embodiments, a list of candidate peptides is narrowed by eliminating: a peptide that has not been previously detected on a mass spectrometer, a peptide susceptible to a modification that interferes with accurate quantitation, a miscleaved peptide comprising an internal protease recognition site, a peptide with relatively inaccessible ends evidenced by the presence of miscleaved peptides, a peptide that is not unique to the sequence of the protein of interest, a peptide not present in the mature protein, or a combination thereof.

In an embodiment, the detection of a peptide is improved by changing the conditions for fragmenting that peptide prior to detecting a multiplicity of the peptides with the mass spectrometer. In exemplary embodiments, the fragmentation condition is the collision energy.

In various other embodiments, the method further comprises adding a stable isotope-labeled peptide to the sample prior to mass spectrometry. In some embodiments, the absolute amount of a peptide in the sample is determined by comparing the MS signals of natural and stable isotope-labeled peptides.

In other embodiments, the comprehensive list of candidate peptides is narrowed by eliminating peptides. In other embodiments, conventional criteria are used to eliminate peptides from the comprehensive list of candidate peptides by eliminating peptides that: (i) were never detected by MS on any instrument, (ii) are not unique to the sequence of the protein of interest, (iii) are not located within the mature protein, (iv) contain amino acid residues such as methionine, cysteine, and/or asparagine that are subjected to posttranslational modifications that interfere with accurate quantitation by mass spectrometry, (v) are miscleaved or partially cleaved, (vi) are post-translationally modified in vivo, (vii) and/or a combination thereof.

In various other embodiments, transitions for each peptide with high and reproducible peak intensities are identified. In other embodiments, the collision energy for each transition is optimized. In other embodiments, mass spectrometry comprises selected reaction monitoring (SRM), or multiple reaction monitoring (MRM). In other embodiments, SRM or MRM is performed on a triple quadrapole mass spectrometer. In other embodiments, the peptides uniquely associated with the polypeptide or protein of interest are those with high correlations, strong signals, high signal/noise and/or sequences unique to the protein of interest.

Selected-ion monitoring (SIM) or selected reaction monitoring (SRM) or multiple reaction monitoring (MRM) provide the simplest method set up and the most selective and sensitive quantification. SRM/MRM/SIM is a method used in tandem mass spectrometry in which an ion of a particular mass is selected in the first stage of a tandem mass spectrometer and an ion product of a fragmentation reaction of the precursor ion is selected in the second mass spectrometer stage for detection. Examples of triple quadrupole mass spectrometers (TQMS) that can perform MRM/SRM/SIM include but are not limited to: QTRAP® 6500 and 5500 System (Sciex); Triple QTriple Quad 6500 System (Sciex); Agilent 6400 Series Triple Quadrupole LC/MS systems; or Thermo Scientific™ TSQ™ Triple Quadrupole system.

In various other embodiments, stable isotope-labeled peptide standards for absolute quantification are used. In other embodiments, the peptide labeled with a stable isotope is used as an internal standard to obtain absolute quantification of the polypeptide or protein of interest. In other embodiments, the peptides are quantified and then the amount of the parent protein present is inferred before digesting the sample with trypsin. In other embodiments, MS responses are used to determine an upper limit of quantification (ULOQ) and a lower limit of quantification (LLOQ).

In various embodiments, the MS data comprises raw MS data obtained from a mass spectrometer and/or processed MS data in which peptides and their fragments (e.g., transitions and MS peaks) are already identified, analyzed and/or quantified. In various embodiments, the MS data is Selective Reaction Monitoring (SRM) data or Parallel-Reaction Monitoring (PRM) data and/or Multiple Reaction Monitoring (MRM) data. In various embodiments, the MS data is Shotgun CID MS data, Original DIA MS Data, MSE MS data, p2CID MS Data, PAcIFIC MS Data, AIF MS Data, XDLA MS Data, SWATH MS data, or FT-ARM MS Data, or a combination thereof.

In various embodiments, acquiring MS data comprises operating a TripleTOF mass spectrometer, a triple quadrupole mass spectrometer, a liquid chromatography-mass spectrometry (LC-MS) system, a gas chromatography-mass spectrometry (GC-MS) system, or a tandem mass spectrometry (MS/MS) system, a dual time-of-flight (TOF-TOF) mass spectrometer, or a combination thereof.

In various embodiments, acquiring MS data comprises operating a mass spectrometer. Examples of the mass spectrometer include but are not limited to high-resolution instruments such as Triple-TOF, Orbitrap, Fourier transform, and tandem time-of-flight (TOF/TOF) mass spectrometers; and high-sensitivity instruments such as triple quadrupole, ion trap, quadrupole TOF (QTOF), and Q trap mass spectrometers, and their hybrid and/or combination. High-resolution instruments are used to maximize the detection of peptides with minute mass-to-charge ratio (m/z) differences. Conversely, because targeted proteomics emphasize sensitivity and throughput, high-sensitivity instruments are used. In some embodiments, the mass spectrometer is a TripleTOF mass spectrometer. In some embodiments, the mass spectrometer is a triple quadrupole mass spectrometer.

In various embodiments, the MS data is collected by a targeted acquisition method. Examples of the targeted acquisition method include but are not limited to Selective Reaction Monitoring (SRM) and/or Multiple Reaction Monitoring (MRM) methods. In various embodiments, acquiring MS data comprises acquiring Selective Reaction Monitoring (SRM) data and/or Multiple Reaction Monitoring (MRM) data.

In various embodiments, the MS data is collected by a data independent acquisition (DIA) method. In various embodiments, the MS data is collected by data dependent acquisition (DDA) method.

Non-limiting examples of mass spectrometry techniques include collision-induced dissociation (CID), higher-energy collisional dissociation (HCD), electron-transfer dissociation (ETD), etc.

Abbreviations: MS, Mass Spectrometry; LC-MS/MS, liquid chromatography-tandem mass spectrometry; LC-SRM-MS, liquid chromatography selected reaction monitoring mass spectrometry; CV %. Coefficient of variation; SIL peptide, Stable Isotope-Labeled Peptide; DIA-MS, Data Independent acquisition mass spectrometry.

Kits

The exact nature of the components configured in the inventive kit depends on its intended purpose. In one embodiment, the kit is configured particularly for human subjects. In further embodiments, the kit is configured for research and/or veterinary applications, treating subjects such as, but not limited to, farm animals, domestic animals, and laboratory animals (e.g., mouse or mice).

The materials or components assembled in the kit can be provided to the practitioner stored in any convenient and suitable ways that preserve their operability and utility. For example, the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

In various embodiments, the present invention provides a kit for identifying protein biomarkers of chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) one or more proteases; (c) reagents and instructions for sample processing and preparation; and (d) instructions for using the kit to identify protein biomarkers of chronic kidney disease in the subject. In some embodiments, the kit further comprises instructions for using the kit to identify protein biomarkers of chronic kidney disease by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a kit for diagnosing chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) one or more proteases; (c) reagents and instructions for sample processing and preparation; and (d) instructions for using the kit to provide a diagnosis of chronic kidney disease in the subject.

In various embodiments, the present invention provides a kit for prognosing chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) one or more proteases; (c) reagents and instructions for sample processing and preparation; and (d) instructions for using the kit to provide a prognosis of chronic kidney disease in the subject.

In various embodiments, the present invention provides a kit for determining progression of chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) one or more proteases; (c) reagents and instructions for sample processing and preparation; and (d) instructions for using the kit to determine progression of chronic kidney disease in the subject.

In various embodiments, the present invention provides a kit for identifying protein biomarkers of chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to identify protein biomarkers of chronic kidney disease in the subject.

In various embodiments, the present invention provides a kit for diagnosing chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to provide a diagnosis of chronic kidney disease in the subject.

In various embodiments, the present invention provides a kit for prognosing chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to provide a prognosis of chronic kidney disease in the subject.

In various embodiments, the present invention provides a kit for determining progression of chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to determine progression of chronic kidney disease in the subject.

In various embodiments, the present invention provides a kit for identifying protein biomarkers of chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) one or more proteases; (c) reagents and instructions for sample processing and preparation; and (d) instructions for using the kit to identify protein biomarkers of chronic kidney disease in the subject. In some embodiments, the internal standard comprises one or more isotopically labeled peptides, one or more isotopically labeled proteins, or any combination thereof. In some embodiments, the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof. In some embodiments, identification of protein biomarkers of chronic kidney disease comprises, obtaining a sample from the subject, wherein the subject has chronic kidney disease; treating the sample with one or more proteases to obtain a digested sample comprising one or more peptides; detecting and/or measuring and/or quantifying the peptides in the digested sample, wherein the detecting and/or measuring and/or quantifying is performed using mass spectrometry; correlating the peptides to one or more proteins so as to obtain a protein biomarker signature for the sample; and comparing the protein biomarker signature from the sample to a protein biomarker signature from a reference sample; wherein protein biomarkers of chronic kidney disease are identified. In some embodiments, the one or more peptides are correlated to one or more proteins according to Table 1 and/or Table 2 and/or Table 6 and/or Table 7.

In various embodiments, the present invention provides a kit for identifying at least one protein biomarker of chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to identify the protein biomarker of chronic kidney disease in the subject. In some embodiments, the internal standard comprises one or more proteins labeled with a detectable moiety, wherein the one or more proteins are selected from Table 1 and/or Table 2 and/or Table 6 and/or Table 7. In some embodiments, identification of the at least one protein biomarker of chronic kidney disease comprises, obtaining a sample from the subject, wherein the subject has chronic kidney disease; detecting and/or measuring and/or quantifying the protein biomarker in the sample, wherein the detecting and/or measuring and/or quantifying is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof; constructing a protein biomarker signature for the subject from the sample; and comparing the protein biomarker signature from the subject's sample to a protein biomarker signature from a reference sample so as to identify protein biomarkers of chronic kidney disease in the subject. In some embodiments, the one or more protein biomarkers are selected from Table 1 and/or Table 2 and/or Table 6 and/or Table 7.

In various embodiments, the present invention provides a kit for diagnosing chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) one or more proteases; (c) reagents and instructions for sample processing and preparation; and (d) instructions for using the kit to provide a diagnosis of chronic kidney disease in the subject. In some embodiments, the internal standard comprises one or more isotopically labeled peptides, one or more isotopically labeled proteins, or any combination thereof. In some embodiments, the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof. In some embodiments, the diagnosis of chronic kidney disease comprises, obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample provides a diagnosis of chronic kidney disease in the subject. In some embodiments, the one or more peptides are correlated to one or more proteins according to Table 1 and/or Table 2 and/or Table 6 and/or Table 7. In some embodiments, measuring the peptides in the digested sample is performed using at least one selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides a kit for diagnosing chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to provide a diagnosis of chronic kidney disease in the subject. In some embodiments, the internal standard comprises one or more proteins labeled with a detectable moiety, wherein the one or more proteins are selected from Table 1 and/or Table 2 and/or Table 6 and/or Table 7. In some embodiments, identification of the at least one protein biomarker of chronic kidney disease comprises, obtaining a sample from the subject; detecting and/or measuring and/or quantifying the protein biomarker in the sample, wherein the detecting and/or measuring and/or quantifying is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof; constructing a protein biomarker signature for the subject from the sample; comparing the protein biomarker signature from the subject's sample to a protein biomarker signature from a reference sample; wherein a change in the protein biomarker signature from the subject relative to the protein biomarker signature from the reference sample provides a diagnosis of chronic kidney disease in the subject. In some embodiments, the one or more protein biomarkers are selected from Table 1 and/or Table 2 and/or Table 6 and/or Table 7.

In various embodiments, the present invention provides a kit for prognosing chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) one or more proteases; (c) reagents and instructions for sample processing and preparation; and (d) instructions for using the kit to provide a prognosis of chronic kidney disease in the subject. In some embodiments, the internal standard comprises one or more isotopically labeled peptides, one or more isotopically labeled proteins, or any combination thereof. In some embodiments, the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof. In some embodiments, the prognosis of chronic kidney disease comprises, obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample provides a prognosis of chronic kidney disease in the subject. In some embodiments, the one or more peptides are correlated to one or more proteins according to Table 1 and/or Table 6. In some embodiments, measuring the peptides in the digested sample is performed using at least one selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, present invention provides a kit for prognosing chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to provide a prognosis of chronic kidney disease in the subject. In some embodiments, the internal standard comprises one or more proteins labeled with a detectable moiety, wherein the one or more proteins are selected from Table 1 and/or Table 6. In some embodiments, identification of the at least one protein biomarker of chronic kidney disease comprises, obtaining a sample from the subject; detecting and/or measuring and/or quantifying the protein biomarker in the sample, wherein the detecting and/or measuring and/or quantifying is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof; constructing a protein biomarker signature for the subject from the sample; comparing the protein biomarker signature from the subject's sample to a protein biomarker signature from a reference sample, wherein a change in the protein biomarker signature from the subject relative to the protein biomarker signature from the reference sample provides a prognosis of chronic kidney disease in the subject. In some embodiments, the one or more protein biomarkers are selected from Table 1 and/or Table 6.

In various embodiments, the present invention provides a kit for determining progression of chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) one or more proteases; (c) reagents and instructions for sample processing and preparation; and (d) instructions for using the kit to determine progression of chronic kidney disease in the subject. In some embodiments, the internal standard comprises one or more isotopically labeled peptides, one or more isotopically labeled proteins, or any combination thereof. In some embodiments, the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof. In some embodiments, determining the progression of chronic kidney disease comprises, obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample is indicative of progression of chronic kidney disease in the subject. In some embodiments, the one or more peptides are correlated to one or more proteins according to Table 2 and/or Table 7. In some embodiments, measuring the peptides in the digested sample is performed using at least one selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, present invention provides a kit for determining progression of chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to determine progression of chronic kidney disease in the subject. In some embodiments, the internal standard comprises one or more proteins labeled with a detectable moiety, wherein the one or more proteins are selected from Table 2 and/or Table 7. In some embodiments, identification of the at least one protein biomarker of chronic kidney disease comprises, obtaining a sample from the subject; detecting and/or measuring and/or quantifying the protein biomarker in the sample, wherein the detecting and/or measuring and/or quantifying is performed using at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof, constructing a protein biomarker signature for the subject from the sample; comparing the protein biomarker signature from the subject's sample to a protein biomarker signature from a reference sample, wherein a change in the protein biomarker signature from the subject relative to the protein biomarker signature from the reference sample is indicative of progression of chronic kidney disease in the subject. In some embodiments, the one or more protein biomarkers are selected from Table 2 and/or Table 7.

In various embodiments, the present invention provides a kit for identifying protein biomarkers of chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to identify protein biomarkers of chronic kidney disease in the subject.

In various embodiments, the present invention provides a kit for diagnosing chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to provide a diagnosis of chronic kidney disease in the subject.

In various embodiments, present invention provides a kit for prognosing chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to provide a prognosis of chronic kidney disease in the subject.

In various embodiments, the present invention provides a kit for determining progression of chronic kidney disease in a subject, the kit comprising: (a) one or more internal standards suitable for any one or more of mass spectrometry, antibody method, antibodies, nucleic acid aptamer method, nucleic acid aptamers, immunoassay, ELISA, immunoprecipitation, SISCAPA, Western blot, or combination thereof; (b) reagents and instructions for sample processing and preparation; and (c) instructions for using the kit to determine progression of chronic kidney disease in the subject.

In some embodiments, the kit further comprises instructions for using the kit to identify protein biomarkers of chronic kidney disease by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In some embodiments, the kit further comprises instructions for using the kit to identify protein biomarkers of chronic kidney disease by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof, so as to provide a prognosis of chronic kidney disease in the subject.

In some embodiments, the kit further comprises instructions for using the kit to identify protein biomarkers of chronic kidney disease by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof, so as to determine progression of chronic kidney disease in the subject.

In some embodiments, the kit further comprises instructions for using the kit to identify and quantify protein biomarkers of chronic kidney disease by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In some embodiments, the kit further comprises instructions for using the kit to identify and quantify protein biomarkers of chronic kidney disease by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof, so as to provide a prognosis of chronic kidney disease in the subject.

In some embodiments, the kit further comprises instructions for using the kit to identify and quantify protein biomarkers of chronic kidney disease by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof, so as to determine progression of chronic kidney disease in the subject.

In some embodiments, the kit further comprises instructions for using the kit to detect and determine an amount of protein biomarkers of chronic kidney disease by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In some embodiments, the kit further comprises instructions for using the kit to detect and determine an amount of protein biomarkers of chronic kidney disease by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof, so as to provide a prognosis of chronic kidney disease in the subject.

In some embodiments, the kit further comprises instructions for using the kit to detect and determine an amount of protein biomarkers of chronic kidney disease by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof, so as to determine progression of chronic kidney disease in the subject.

Assays

In various embodiments, the present invention provides an assay for prognosing chronic kidney disease in a subject, comprising: i) obtaining a sample from the subject, wherein the sample comprises at least one protein, and wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q81IVF5), D-tyrosyl-tRNA (Tyr) deacylase 1 (UniProt Accession No. Q8TEA8), Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; ii) identifying the protein and determining an amount of the protein in the sample from the subject by at least one technique selected from the group consisting of mass spectrometry, antibody method, antibodies, nucleic acid aptamer method, nucleic acid aptamers, immunoassay, ELISA, immunoprecipitation, SISCAPA, Western blot, or combination thereof; iii) constructing a protein biomarker signature for the subject, wherein the biomarker signature comprises the amount of the protein in the sample from the subject; and iv) comparing the amount of the protein in the sample from the subject to an amount of the protein in a reference sample, wherein a change in the amount of the protein in the sample from the subject relative to the amount of the protein in the reference sample is a prognosis of chronic kidney disease in the subject.

In various embodiments, the present invention provides an assay for determining progression of chronic kidney disease in a subject, comprising: i) obtaining a sample from the subject, wherein the sample comprises at least one protein, and wherein the protein is selected from the group consisting of Uteroglobin (UniProt Accession No. P11684), Putative sodium-coupled neutral amino acid transporter 10 (UniProt Accession No. Q9HBR0), Protein AMBP (precursors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859), Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; ii) identifying the protein and determining an amount of the protein in the sample from the subject by at least one technique selected from the group consisting of mass spectrometry, antibody method, antibodies, nucleic acid aptamer method, nucleic acid aptamers, immunoassay, ELISA, immunoprecipitation, SISCAPA, Western blot, or combination thereof; iii) constructing a protein biomarker signature for the subject, wherein the biomarker signature comprises the amount of the protein in the sample from the subject; and iv) comparing the amount of the protein in the sample from the subject to an amount of the protein in a reference sample, wherein a change in the amount of the protein in the sample from the subject relative to the amount of the protein in the reference sample is indicative of progression of chronic kidney disease in the subject.

In various embodiments, the present invention provides an assay for prognosing chronic kidney disease in a subject, comprising: i) obtaining a sample from the subject, ii) detecting at least one protein in the sample by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof; wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1 (UniProt Accession No. Q8TEA8), Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; iii) determining an amount of the protein in the sample from the subject; iv) constructing a protein biomarker signature for the subject, wherein the biomarker signature comprises the amount of the protein in the sample from the subject; and v) comparing the amount of the protein in the sample from the subject to an amount of the protein in a reference sample, wherein a change in the amount of the protein in the sample from the subject relative to the amount of the protein in the reference sample is a prognosis of chronic kidney disease in the subject. In some embodiments, the determining an amount of the protein in the sample from the subject is by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides an assay for prognosing chronic kidney disease in a subject, comprising: i) obtaining a sample from the subject, ii) detecting and determining an amount of at least one protein in the sample by at least one technique selected from the group consisting of mass spectrometry, antibody method, antibodies, nucleic acid aptamer method, nucleic acid aptamers, immunoassay, ELISA, immunoprecipitation, SISCAPA, Western blot, or combination thereof; wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1

(UniProt Accession No. Q8TEA8), Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof; iii) constructing a protein biomarker signature for the subject, wherein the biomarker signature comprises the amount of the protein in the sample from the subject; and iv) comparing the amount of the protein in the sample from the subject to an amount of the protein in a reference sample, wherein a change in the amount of the protein in the sample from the subject relative to the amount of the protein in the reference sample is a prognosis of chronic kidney disease in the subject.

In various embodiments, the present invention provides an assay for determining progression of chronic kidney disease in a subject, comprising: i) obtaining a sample from the subject, ii) detecting at least one protein in the sample by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof; wherein the protein is selected from the group consisting of Uteroglobin (UniProt Accession No. P11684), Putative sodium-coupled neutral amino acid transporter 10 (UniProt Accession No. Q9HBR0), Protein AMBP (precusors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859), Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; iii) determining an amount of the protein in the sample from the subject; iv) constructing a protein biomarker signature for the subject, wherein the biomarker signature comprises the amount of the protein in the sample from the subject; and v) comparing the amount of the protein in the sample from the subject to an amount of the protein in a reference sample, wherein a change in the amount of the protein in the sample from the subject relative to the amount of the protein in the reference sample is indicative of progression of chronic kidney disease in the subject. In some embodiments, the determining an amount of the protein in the sample from the subject is by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof.

In various embodiments, the present invention provides an assay for determining progression of chronic kidney disease in a subject, comprising: i) obtaining a sample from the subject, ii) detecting and determining an amount of at least one protein in the sample by at least one technique selected from the group consisting of mass spectrometry, antibody method, antibodies, nucleic acid aptamer method, nucleic acid aptamers, immunoassay, ELISA, immunoprecipitation, SISCAPA, Western blot, and combinations thereof, wherein the protein is selected from the group consisting of Uteroglobin (UniProt Accession No. P11684), Putative sodium-coupled neutral amino acid transporter 10 (UniProt Accession No. Q9HBR0), Protein AMBP (precusors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859), Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof; iii) constructing a protein biomarker signature for the subject, wherein the biomarker signature comprises the amount of the protein in the sample from the subject; and iv) comparing the amount of the protein in the sample from the subject to an amount of the protein in a reference sample, wherein a change in the amount of the protein in the sample from the subject relative to the amount of the protein in the reference sample is indicative of progression of chronic kidney disease in the subject.

TABLE 1

Candidate prognosis markers (Ranked by Wilcoxon P-value).

| UniProt KB Accessions | Protein Group Description | % Missing | MW, kDA | Random Effects Model (log transformed) | | | Wilcoxon Sign Rank | |
|---|---|---|---|---|---|---|---|---|
| | | | | Beta | SD | p-value | p-value | Rank |
| P04075 | Fructose-bisphosphatealdolase A | 2 | 39 | −0.559 | 0.159 | 0.000 | 0.002 | 1 |
| P35555 | Fibrillin-1 | 70 | 312 | 0.515 | 0.153 | 0.001 | 0.005 | 2 |
| P13987 | CD59 glycoprotein | 41 | 14 | 0.477 | 0.113 | 0.000 | 0.005 | 3 |
| P02652 | Apolipoprotein A-II (APOA2) | 44 | 11 | 0.827 | 0.248 | 0.001 | 0.006 | 4 |
| P04746 | Pancreatic alpha-amylase | 20 | 58 | −0.729 | 0.225 | 0.001 | 0.010 | 5 |
| Q76M96-2 | Coiled-coil domain-containing protein 80 (CCDC80) including isoform 2 | 55 | 110 | −0.303 | 0.105 | 0.004 | 0.011 | 6 |
| P02656 | Apolipoprotein C-III (APOC3) | 3 | 11 | 0.738 | 0.208 | 0.000 | 0.011 | 7 |
| P81605-2 | Dermcidin | 0 | 12 | 0.395 | 0.113 | 0.000 | 0.013 | 8 |
| P01833 | Polymeric immunoglobulin receptor | 5 | 83 | 0.462 | 0.184 | 0.012 | 0.013 | 9 |
| Q8NBJ4-2 | Golgi membrane protein 1 | 67 | 44 | 0.587 | 0.157 | 0.000 | 0.014 | 10 |
| Q8IVF5-2 | T-lymphoma invasion and metastasis-inducing protein 2 | 22 | 193 | −0.611 | 0.248 | 0.014 | 0.014 | 11 |
| Q8TEA8 | D-tyrosyl-tRNA(Tyr) deacylase 1 | 70 | 2.3 | −0.329 | 0.111 | 0.003 | 0.015 | 12 |
| P55160-2 | Nck-associated protein 1 | 0 | 12.3 | −0.277 | 0.12 | 0.022 | 0.017 | 13 |
| P00738 | Haptoglobin | 52 | 45 | 1.045 | 0.425 | 0.014 | 0.018 | 14 |
| Q9Y490 | Talin-1 | 48 | 270 | −0.536 | 0.188 | 0.004 | 0.019 | 15 |
| Q9Y5K6 | CD2-associated protein | 88 | 71 | −0.26 | 0.074 | 0.000 | 0.020 | 16 |
| Q27J81-2 | Inverted formin-2 | 88 | 135 | −0.26 | 0.068 | 0.000 | 0.020 | 17 |
| P47756-2 | F-actin-capping protein subunit beta | 88 | 31 | −0.258 | 0.108 | 0.017 | 0.020 | 18 |
| P01023 | Alpha-2-macroglobulin | 0 | 163 | 0.279 | 0.103 | 0.007 | 0.020 | 19 |
| Q8N6C8-3 | Leukocyte immunoglobulin-like receptor subfamily A member 3 | 45 | 49 | 0.385 | 0.169 | 0.022 | 0.020 | 20 |
| Q99784-3 | Noelin including isoform 3 | 63 | 54 | −0.387 | 0.144 | 0.007 | 0.022 | 21 |
| P02768 | Serum albumin | 0 | 69 | 0.781 | 0.296 | 0.008 | 0.024 | 22 |
| O14791-2 | Apolipoprotein L1 (APOL1) | 48 | 46 | 0.393 | 0.143 | 0.006 | 0.025 | 23 |
| P02763 | Alpha-1-acid glycoprotein 1 (ORM1) | 22 | 24 | 0.867 | 0.374 | 0.021 | 0.027 | 24 |
| Q86YZ3 | Hornerin | 0 | 282 | 0.421 | 0.214 | 0.049 | 0.028 | 25 |

Small p-values are p < 0.05; p < 0.01
Isoforms are determined based on peptide observations in the original discovery cohort analysis.

TABLE 2

Candidate progression markers (Ranked by Wilcoxon sign rank P-value).

| UniProt KB Accessions | Protein Group Description | % Missing | MW, kDa | Random Effects Model (log transformed) | | | Wilcoxon Sign Rank | |
|---|---|---|---|---|---|---|---|---|
| | | | | Beta | SD | p-value | p-value | Rank |
| P11684 | Uteroglobin | 17 | 10 | 0.770 | 0.188 | 0.000 | 0.001 | 1 |
| Q9HBR0 | Putative sodium-coupled neutral amino acid transporter 10 | 2 | 120 | 0.741 | 0.181 | 0.000 | 0.001 | 2 |
| P02760 | Protein AMBP (precusors of alpha-1 microglobulin) | 0 | 39 | 0.365 | 0.134 | 0.007 | 0.004 | 3 |
| P15144 | Aminopeptidase N | 5 | 110 | −0.510 | 0.193 | 0.008 | 0.004 | 4 |
| P02741 | C-reactive protein (CRP) | 0 | 25 | −0.370 | 0.180 | 0.039 | 0.004 | 5 |
| P50552 | Vasodilator-stimulated phosphoprotein (VASP) | 9 | 40 | −0.396 | 0.124 | 0.001 | 0.005 | 6 |
| P01034 | Cystatin-C | 0 | 16 | 0.370 | 0.162 | 0.023 | 0.006 | 7 |
| P27797 | Calreticulin | 55 | 48 | 0.671 | 0.184 | 0.000 | 0.006 | 8 |
| P31944 | Caspase-14 | 11 | 28 | −0.805 | 0.305 | 0.008 | 0.007 | 9 |
| P08123 | Collagen alpha-2(I) chain | 13 | 129 | −0.473 | 0.169 | 0.005 | 0.007 | 10 |
| P24S92 | Insulin-like growth factor-binding protein 6 | 0 | 25 | 0.299 | 0.160 | 0.061 | 0.008 | 11 |
| Q92859-2 | Neogenin | 31 | 154 | −0.585 | 0.214 | 0.006 | 0.008 | 12 |
| Q15517 | Corneodesmosin | 42 | 52 | −0.594 | 0.184 | 0.001 | 0.009 | 13 |
| Q9UDY2-3 | Isoform C1 of Tight junction protein ZO-2 | 52 | 131 | −0.411 | 0.183 | 0.024 | 0.010 | 14 |
| P80188 | Neutrophil gelatinase-associated lipocalin (NGAL) | 0 | 23 | 0.294 | 0.155 | 0.058 | 0.010 | 15 |
| Q14767 | Latent-transforming growth factor beta-binding protein 2 | 3 | 195 | 0.385 | 0.143 | 0.007 | 0.011 | 16 |

TABLE 2-continued

Candidate progression markers (Ranked by Wilcoxon sign rank P-value).

| UniProt KB Accessions | Protein Group Description | % Missing | MW, kDa | Random Effects Model (log transformed) Beta | SD | p-value | Wilcoxon Sign Rank p-value | Rank |
|---|---|---|---|---|---|---|---|---|
| P13591-1 | Neural cell adhesion molecule 1 (NCAM1) | 25 | 93 | −0.444 | 0.217 | 0.041 | 0.012 | 17 |
| P81605-2 | Dermcidin (DCD) | 0 | 12 | −0.160 | 0.113 | 0.158 | 0.013 | 18 |
| P05543 | Thyroxine-binding globulin (SERPINA7) | 0 | 46 | −0.200 | 0.080 | 0.013 | 0.013 | 19 |
| P08237-2 | 6-phosphofructokinase, muscle type (PFKM) | 70 | 82 | −0.344 | 0.135 | 0.011 | 0.013 | 20 |
| P41222 | BTP (Prostaglandin-H2 D-isomerase) | 0 | 21 | 0.177 | 0.138 | 0.201 | 0.014 | 21 |
| Q8N6C8-3 | Leukocyte immunoglobulin-like receptor subfamily A member 3 (LILRA3) | 45 | 49 | −0.324 | 0.169 | 0.055 | 0.017 | 22 |
| P04080 | Cystatin-B | 66 | 11 | 0.480 | 0.186 | 0.010 | 0.018 | 23 |
| Q6UX71 | Plexin domain-containing protein 2 | 13 | 60 | −0.379 | 0.156 | 0.015 | 0.019 | 24 |
| Q9BXX0 | EMILIN-2 | 70 | 116 | 0.242 | 0.099 | 0.014 | 0.020 | 25 |

Small p-values are p < 0.05; p < 0.01
Isoforms are determined based on peptide observations in the original discovery cohort analysis.

TABLE 6

Table 6: candidate prognostic markers

| UniPro tKB Accessions | pval_t0 | % missing data | Beta | SD | Protein name (species (OS), gene name (GN), isoform) |
|---|---|---|---|---|---|
| P04075 | 0.0021 | 2 | −0.5 | 0.12 | Fructose-bisphosphate aldolase A OS = *Homo sapiens* GN = ALDOA |
| P35555 | 0.0048 | 70 | 1.15 | 0.41 | Fibrillin-1 OS = *Homo sapiens* GN = FBN1 |
| P02652 | 0.0058 | 44 | 1.39 | 0.29 | Apolipoprotein A-II OS = *Homo sapiens* GN = APOA2 |
| Q76M96 | 0.0107 | 55 | −0.3 | 0.40 | Coiled-coil domain-containing protein 80 OS = *Homo sapiens* GN = CCDC80 (including isoform 2) |
| P02656 | 0.0112 | 3 | 0.81 | 0.16 | Apolipoprotein C-III OS = *Homo sapiens* GN = APOC3 |
| P81605 | 0.013 | 0 | 0.37 | 0.09 | Dermcidin OS = *Homo sapiens* GN = DCD (isoform 2) |
| P01833 | 0.013 | 5 | 0.73 | 0.20 | Polymeric immunoglobulin receptor OS = *Homo sapiens* GN = PIGR |
| Q8NBJ4 | 0.0137 | 67 | 1.1 | 0.41 | Golgi membrane protein 1 OS = *Homo sapiens* GN = GOLM1(isoform 2) |
| P04746 | 0.0144 | 20 | −0.8 | 0.21 | Pancreatic alpha-amylase OS = *Homo sapiens* GN = AMY2A |
| Q8TEA8 | 0.0147 | 70 | −0.4 | 0.42 | D-tyrosyl-tRNA(Tyr) deacylase 1 OS = *Homo sapiens* GN = DTD1 |
| P55160 | 0.0168 | 0 | −0.3 | 0.14 | Nck-associated protein 1-like OS = *Homo sapiens* GN = NCKAP1L (isoform 2) |
| Q8IVF5 | 0.0173 | 22 | −1 | 0.24 | T-lymphoma invasion and metastasis-inducing protein 2 OS = *Homo sapiens* GN = TIAM2 (including isoform 2) |
| P00738 | 0.0185 | 52 | 2.08 | 0.18 | Haptoglobin OS = *Homo sapiens* GN = HP |
| P47756 | 0.0197 | 88 | −0.3 | 0.47 | F-actin-capping protein subunit beta OS = *Homo sapiens* GN = CAPZB (including isoform 2) |
| Q27J81 | 0.0197 | 88 | −0.3 | 0.47 | Inverted formin-2 OS = *Homo sapiens* GN = INF2 |
| Q9Y5K6 | 0.0197 | 88 | −0.3 | 0.47 | CD2-associated protein OS = *Homo sapiens* GN = CD2AP |
| P01023 | 0.02 | 0 | 0.27 | 0.02 | Alpha-2-macroglobulin OS = *Homo sapiens* GN = A2M |
| P13987 | 0.021 | 41 | 0.42 | 0.40 | CD59 glycoprotein OS = *Homo sapiens* GN = CD59 |
| O14791 | 0.021 | 48 | 0.76 | 0.36 | Apolipoprotein L1 OS = *Homo sapiens* GN = APOL1 (isoform 2) |

TABLE 7

Table 7: Candidate progression markers

| UniProtKB Accessions | pval_case | % missing data | Beta | SD | Protein name (species (OS), gene (GN), isoform) |
|---|---|---|---|---|---|
| P11684 | 0.0011 | 17 | 1.04 | 0.3 | Uteroglobin OS = *Homo sapiens* GN = SCGB1A1 |
| Q9HBR0 | 0.0012 | 2 | 0.73 | 0.1 | sodium-coupled neutral amino acid transporter 10 OS = *Homo sapiens* GN = SLC38A10 (putative) |
| P15144 | 0.0034 | 5 | −0.54 | 0.1 | Aminopeptidase N OS = *Homo sapiens* GN = ANPEP |
| P02760 | 0.0041 | 0 | 0.39 | 0.0 | Protein AMBP OS = *Homo sapiens* GN = AMBP |
| P02741 | 0.0044 | 0 | −0.35 | 0.1 | C-reactive protein OS = *Homo sapiens* GN = CRP |
| P50552 | 0.0048 | 9 | −0.68 | 0.3 | Vasodilator-stimulated phosphoprotein OS = *Homo sapiens* GN = VASP |
| P01034 | 0.0056 | 0 | 0.41 | 0.1 | Cystatin-C OS = *Homo sapiens* GN = CST3 |
| P27797 | 0.0058 | 55 | 1.09 | 0.3 | Calreticulin OS = *Homo sapiens* GN = CALR |

TABLE 7-continued

Table 7: Candidate progression markers

| UniProtKB Accessions | pval_case | % missing data | Beta | SD | Protein name (species (OS), gene (GN), isoform) |
|---|---|---|---|---|---|
| P08123 | 0.0073 | 13 | −0.77 | 0.2 | Collagen alpha-2(I) chain OS = Homo sapiens GN = COL1A2 |
| P31944 | 0.0075 | 11 | −1.08 | 0.2 | Caspase-14 OS = Homo sapiens GN = CASP14 |
| P24592 | 0.0083 | 0 | 0.25 | 0.1 | Insulin-like growth factor-binding protein 6 OS = Homo sapiens GN = IGFBP6 |
| Q9UDY2 | 0.0091 | 52 | −0.67 | 0.4 | Tight junction protein ZO-2 OS = Homo sapiens GN = TJP2 (isoform C1) |
| P80188 | 0.0105 | 0 | 0.36 | 0.1 | Neutrophil gelatinase-associated lipocalin OS = Homo sapiens GN = LCN2 |
| Q14767 | 0.0114 | 3 | 0.49 | 0.2 | Latent-transforming growth factor beta-binding protein 2 OS = Homo sapiens GN = LTBP2 |
| P81605 | 0.0128 | 0 | −0.18 | 0.1 | Dermcidin OS = Homo sapiens GN = DCD (including isoform 2) |
| P05543 | 0.013 | 0 | −0.19 | 0.0 | Thyroxine-binding globulin OS = Homo sapiens GN = SERPINA7 |
| P08237 | 0.0134 | 70 | −0.36 | 0.4 | 6-phosphofructokinase, muscle type OS = Homo sapiens GN = PFKM including isoform 2 |
| P41222 | 0.014 | 0 | 0.2 | 0.1 | BTP = Prostaglandin-H2 D-isomerase OS = Homo sapiens GN = PTGDS |
| P13591 | 0.0144 | 25 | −0.59 | 0.2 | Neural cell adhesion molecule 1 OS = Homo sapiens GN = NCAM1 (Isoform 1) |
| Q15517 | 0.0144 | 42 | −0.93 | 0.3 | Corneodesmosin OS = Homo sapiens GN = CDSN PE = 1 SV = 3 |

Some embodiments of the present invention can be defined as any of the following numbered paragraphs:

1. A method for identifying protein biomarkers of chronic kidney disease in a subject, comprising: obtaining a sample from the subject, wherein the subject has chronic kidney disease; treating the sample with one or more proteases to obtain a digested sample comprising one or more peptides; detecting and/or measuring and/or quantifying the peptides in the digested sample, wherein the detecting and/or measuring and/or quantifying is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample; wherein protein biomarkers of chronic kidney disease are identified.
2. The method of paragraph 1, wherein the one or more peptides are correlated to one or more proteins according to Table 1 and/or Table 2 and/or Table 6 and/or Table 7.
3. The method of paragraph 1, wherein the subject is a human.
4. The method of paragraph 1, wherein the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof
5. The method of paragraph 1, wherein the mass spectrometry is multiple reaction monitoring (MRM).
6. The method of paragraph 1, wherein the one or more proteins and/or one or more peptides in the sample are modified.
7. The method of paragraph 6, wherein the one or more proteins and/or one or more peptides in the sample are chemically modified.
8. The method of paragraph 6, wherein the modification is any one or more of any one or more of phosphorylation, methylation, acetylation, o-GlycNacylation, s-nitrosylation, citrullination, sumoylation, ubiquitinylation, neddylation, methyglyoxylation, or a post-translational modification.
9. The method of paragraph 1, further comprising adding one or more internal standards to the sample.
10. The method of paragraph 8, wherein the internal standard comprises one or more isotopically labeled peptides, one or more isotopically labeled proteins, or any combination thereof.
11. The method of paragraph 1, wherein the reference sample is obtained from a control subject, wherein the control subject does not have the disease.
12. A kit for identifying protein biomarkers of chronic kidney disease in a subject, the kit comprising: (a) one or more internal standards suitable for any one or more of mass spectrometry, ELISA, immunoprecipitation. SISCAPA, Western blot, or combination thereof; (b) one or more proteases; (c) reagents and instructions for sample processing and preparation; and (d) instructions for using the kit to identify protein biomarkers of chronic kidney disease in the subject.
13. The kit of paragraph 12, wherein the internal standard comprises one or more isotopically labeled peptides, one or more isotopically labeled proteins, or any combination thereof.
14. The kit of paragraph 12, wherein the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof.
15. The kit of paragraph 12, wherein identification of protein biomarkers of chronic kidney disease comprises, obtaining a sample from the subject, wherein the subject has chronic kidney disease; treating the sample with one or more proteases to obtain a digested sample comprising one or more peptides; detecting and/or measuring and/or quantifying the peptides in the digested sample, wherein the detecting and/or measuring and/or quantifying is performed using mass spectrometry; correlating the peptides to one or more proteins so as to obtain a protein biomarker signature for the sample; and comparing the protein biomarker signature from the sample to a protein biomarker signature from a reference sample; wherein protein biomarkers of chronic kidney disease are identified.
16. The kit of paragraph 15, wherein the one or more peptides are correlated to one or more proteins according to Table 1 and/or Table 2 and/or Table 6 and/or Table 7.
17. A method for prognosing chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample provides a prognosis of chronic kidney disease in the subject.

18. The method of paragraph 17, wherein the one or more peptides are correlated to one or more proteins according to Table 1 and/or Table 6.
19. The method of paragraph 17, wherein the subject is a human.
20. The method of paragraph 17, wherein the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof.
21. The method of paragraph 17, wherein the mass spectrometry is multiple reaction monitoring (MRM).
22. The method of paragraph 17, wherein the one or more proteins and/or one or more peptides in the sample are modified.
23. The method of paragraph 22, wherein the one or more proteins and/or one or more peptides in the sample are chemically modified.
24. The method of paragraph 22, wherein the modification is any one or more of any one or more of phosphorylation, methylation, acetylation, o-GlycNacylation, s-nitrosylation, citrullination, sumoylation, ubiquitinylation, neddylation, methyglyoxylation, or a post-translational modification.
25. The method of paragraph 17, further comprising adding one or more internal standards to the sample.
26. The method of paragraph 25, wherein the internal standard comprises one or more isotopically labeled peptides, one or more isotopically labeled proteins, or any combination thereof.
27. The method of paragraph 17, further comprising treating the subject and/or selecting a treatment for and/or providing a treatment to the subject based on the prognosis.
28. A method for assessing the efficacy of the treatment of claim 27, comprising: comparing the protein biomarker signature from the subject to a protein biomarker signature from a reference sample, wherein a change in the protein biomarker signature from the subject relative to the protein biomarker signature from the reference sample is indicative of the efficacy of the treatment.
29. The method of any one of paragraphs 17 or 28, wherein the reference sample is obtained from a control subject, wherein the control subject does not have the disease.
30. The method of any one of paragraphs 17 or 28, wherein the reference sample is obtained from the subject before the subject is treated for the disease.
31. The method of any one of paragraphs 17 or 28, wherein the reference sample is from a subject that has been successfully treated for the disease.
32. A method for treating a subject in need thereof, comprising: obtaining protein biomarker signature results for the subject, wherein the protein biomarker signature results provide a prognosis of chronic kidney disease in the subject; and treating the subject and/or selecting a treatment for and/or providing a treatment to the subject based on the prognosis of chronic kidney disease in the subject.
33. A method for determining progression of chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample is indicative of progression of chronic kidney disease in the subject.
34. The method of paragraph 33, wherein the one or more peptides are correlated to one or more proteins according to Table 2 and/or Table 7.
35. The method of paragraph 33, wherein the subject is a human.
36. The method of paragraph 33, wherein the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof.
37. The method of paragraph 33, wherein the mass spectrometry is multiple reaction monitoring (MRM).
38. The method of paragraph 33, wherein the one or more proteins and/or one or more peptides in the sample are modified.
39. The method of paragraph 38, wherein the one or more proteins and/or one or more peptides in the sample are chemically modified.
40. The method of paragraph 38, wherein the modification is any one or more of any one or more of phosphorylation, methylation, acetylation, o-GlycNacylation, s-nitrosylation, citrullination, sumoylation, ubiquitinylation, neddylation, methyglyoxylation, or a post-translational modification.
41. The method of paragraph 33, further comprising adding one or more internal standards to the sample.
42. The method of paragraph 41, wherein the internal standard comprises one or more isotopically labeled peptides, one or more isotopically labeled proteins, or any combination thereof.
43. The method of paragraph 33, further comprising treating the subject and/or selecting a treatment for and/or providing a treatment to the subject based on the progression of chronic kidney disease in the subject.
44. A method for assessing the efficacy of the treatment of claim 43, comprising: comparing the protein biomarker signature from the subject to a protein biomarker signature from a reference sample, wherein a change in the protein biomarker signature from the subject relative to the protein biomarker signature from the reference sample is indicative of the efficacy of the treatment.

45. The method of any one of paragraphs 33 or 44, wherein the reference sample is obtained from a control subject, wherein the control subject does not have the disease.

46. The method of any one of paragraphs 33 or 44, wherein the reference sample is obtained from the subject before the subject is treated for the disease.

47. The method of any one of paragraphs 33 or 44, wherein the reference sample is from a subject that has been successfully treated for the disease.

48. A method for treating a subject in need thereof, comprising: receiving protein biomarker signature results for the subject, wherein the protein biomarker signature results are indicative of progression of chronic kidney disease in the subject; and treating the subject and/or selecting a treatment for and/or providing a treatment to the subject based on the progression of chronic kidney disease in the subject.

49. A method for diagnosing chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample is indicative of chronic kidney disease in the subject.

50. The method of paragraph 49, wherein the one or more peptides are correlated to one or more proteins according to Table 1 and/or Table 2 and/or Table 6 and/or Table 7.

51. The method of paragraph 49, wherein the subject is a human.

52. The method of paragraph 49, wherein the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof.

53. The method of paragraph 49, wherein the mass spectrometry is multiple reaction monitoring (MRM).

54. The method of paragraph 49, wherein the one or more proteins and/or one or more peptides in the sample are modified.

55. The method of paragraph 54, wherein the one or more proteins and/or one or more peptides in the sample are chemically modified.

56. The method of paragraph 54, wherein the modification is any one or more of any one or more of phosphorylation, methylation, acetylation, o-GlycNacylation, s-nitrosylation, citrullination, sumoylation, ubiquitinylation, neddylation, methyglyoxylation, or a post-translational modification.

57. The method of paragraph 49, further comprising adding one or more internal standards to the sample.

58. The method of paragraph 57, wherein the internal standard comprises one or more isotopically labeled peptides, one or more isotopically labeled proteins, or any combination thereof.

59. The method of paragraph 49, further comprising treating the subject and/or selecting a treatment for and/or providing a treatment to the subject based on the diagnosis.

60. A method for assessing the efficacy of the treatment of claim 59, comprising: comparing the protein biomarker signature from the subject to a protein biomarker signature from a reference sample, wherein a change in the protein biomarker signature from the subject relative to the protein biomarker signature from the reference sample is indicative of the efficacy of the treatment.

61. The method of any one of paragraphs 49 or 60, wherein the reference sample is obtained from a control subject, wherein the control subject does not have the disease.

62. The method of any one of paragraphs 49 or 60, wherein the reference sample is obtained from the subject before the subject is treated for the disease.

63. The method of any one of paragraphs 49 or 60, wherein the reference sample is from a subject that has been successfully treated for the disease.

64 A method for treating a subject in need thereof, comprising: receiving protein biomarker signature results for the subject, providing a diagnosis of chronic kidney disease in the subject based on the protein biomarker signature results; and treating the subject and/or selecting a treatment for and/or providing a treatment to the subject based on the diagnosis.

65. A kit for diagnosing chronic kidney disease in a subject, the kit comprising: (a) one or more internal standards suitable for any one or more of mass spectrometry, ELISA, immunoprecipitation, SISCAPA, Western blot, or combination thereof; (b) one or more proteases; (c) reagents and instructions for sample processing and preparation; and (d) instructions for using the kit to provide a diagnosis of chronic kidney disease in the subject.

66. The kit of paragraph 65, wherein the internal standard comprises one or more isotopically labeled peptides, one or more isotopically labeled proteins, or any combination thereof.

67. The kit of paragraph 65, wherein the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof.

68. The kit of paragraph 65, wherein the diagnosis of chronic kidney disease comprises, obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, w herein a change in the protein biomarker signature from the subject relative to the protein biomarker signature from the reference sample provides a diagnosis of chronic kidney disease in the subject.

69. The kit of paragraph 65, wherein the one or more peptides are correlated to one or more proteins according to Table 1 and/or Table 2 and/or Table 6 and/or Table 7.

70. A kit for prognosing chronic kidney disease in a subject, the kit comprising: (a) one or more internal standards suitable for any one or more of mass spectrometry ELISA, immunoprecipitation, SISCAPA, Western blot, or combination thereof; (b) one or more proteases; (c) reagents and instructions for sample processing and preparation; and (d) instructions for using the kit to provide a prognosis of chronic kidney disease in the subject.

71. The kit of paragraph 70, wherein the internal standard comprises one or more isotopically labeled peptides, one or more isotopically labeled proteins, or any combination thereof.

72. The kit of paragraph 70, wherein the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof.

73. The kit of paragraph 70, wherein the prognosis of chronic kidney disease comprises, obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, wherein a change in the protein biomarker signature from the subject relative to the protein biomarker signature from the reference sample provides a prognosis of chronic kidney disease in the subject.

74. The kit of paragraph 70, wherein the one or more peptides are correlated to one or more proteins according to Table 1 and/or Table 6.

75. A kit for determining progression of chronic kidney disease in a subject, the kit comprising: (a) one or more internal standards suitable for any one or more of mass spectrometry, ELISA, immunoprecipitation, SISCAPA, Western blot, or combination thereof; (b) one or more proteases; (c) reagents and instructions for sample processing and preparation; and (d) instructions for using the kit to determine progression of chronic kidney disease in the subject.

76. The kit of paragraph 77, wherein the internal standard comprises one or more isotopically labeled peptides, one or more isotopically labeled proteins, or any combination thereof.

77. The kit of paragraph 77, wherein the protease is trypsin, chymotrypsin, endoproteinase Lys-C, endoproteinase Asp-N, pepsin, thermolysin, papain, proteinase K, subtilisin, clostripain, exopeptidase, carboxypeptidase, cathepsin C, cyanogen bromide, formic acid, hydroxylamine, or NTCB, or a combination thereof.

78. The kit of paragraph 77, wherein determining the progression of chronic kidney disease comprises, obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, w herein a change in the protein biomarker signature from the subject relative to the protein biomarker signature from the reference sample is indicative of progression of chronic kidney disease in the subject.

79. The kit of paragraph 77, wherein the one or more peptides are correlated to one or more proteins according to Table 2 and/or Table 7.

80. A method for assessing and/or determining the risk of developing chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, ELISA, immunoprecipitation, SISCAPA, Western blot, or combination thereof; correlating the peptides to one or more proteins so as to obtain a protein biomarker signature for the subject; and comparing the protein biomarker signature from the subject to a protein biomarker signature from a reference sample, w herein a change in the protein biomarker signature from the subject relative to the protein biomarker signature from the reference sample is indicative of an increased risk of the subject developing chronic kidney disease.

81. The method of paragraph 82, wherein the one or more peptides are correlated to one or more proteins according to Table 1 and/or Table 2 and/or Table 6 and/or Table 7.

82. A method for identifying and/or assessing chronic kidney disease in a subject, comprising: obtaining a sample from the subject; treating the sample with one or more proteases to obtain a digested sample comprising one or more peptides; measuring the peptides in the digested sample, wherein the measuring is performed using any one or more of mass spectrometry, immunoassay, ELISA, immunoprecipitation, SISCAPA, Western blot, or combination thereof; correlating the peptides to one or more proteins so as to obtain a protein biomarker signature for the subject; and comparing the protein biomarker signature from the subject to one or more reference protein biomarker signatures; and identifying and/or assessing chronic kidney disease in the subject based on the comparison.

83. The method of paragraph 84, wherein the one or more reference protein biomarker signatures are from one or more diseased subjects having chronic kidney disease.

84. The method of paragraph 84, wherein the one or more reference protein biomarker signatures are from one or more healthy subjects.

85. The method of paragraph 84, further comprising treating the subject and/or selecting a treatment and/or providing a treatment and/or selecting a preventative treatment and/or providing a preventative treatment for the subject.

86. The method of paragraph 84, wherein the one or more peptides are correlated to one or more proteins according to Table 1 and/or Table 2 and/or Table 6 and/or Table 7.

Some embodiments of the present invention can be defined as any of the following numbered paragraphs:

87. A method for prognosing chronic kidney disease in a subject, comprising:
   i) obtaining a sample from the subject;
   ii) detecting and determining an amount of at least one protein in the sample by at least one technique selected from the group consisting of mass spectrometry, antibody method, nucleic acid aptamer method, immunoassay, ELISA, immunoprecipitation, SISCAPA, Western blot, and combinations thereof, wherein the protein is selected from the group consisting of Fructose-bisphosphatealdolase A (UniProt Accession No. P04075), Fibrillin-1 (UniProt Accession No. P35555), CD59 glycoprotein (UniProt Accession No. P13987), Apolipoprotein A-II (APOA2) (UniProt Accession No. P02652), Pancreatic alpha-amylase (UniProt Accession No. P04746), Coiled-coil domain-containing protein 80 (CCDC80) including isoform 2 (UniProt Accession No. Q76M96), Apolipoprotein C-III (APOC3) (UniProt Accession No. P02656), Dermcidin (UniProt Accession No. P81605), Polymeric immunoglobulin receptor (UniProt Accession No. P01833), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1 (UniProt Accession No. Q8TEA8). Nck-associated protein 1 (UniProt Accession No. P55160), Haptoglobin (UniProt Accession No. P00738), Talin-1 (UniProt Accession No. Q9Y490), CD2-associated protein (UniProt Accession No. Q9Y5K6), Inverted formin-2 (UniProt Accession No. Q27J81). F-actin-capping protein subunit beta (UniProt Accession No. P47756), Alpha-2-macroglobulin (UniProt Accession No. P01023), Leukocyte immunoglobulin-like receptor subfamily A member 3 (UniProt Accession No. Q8N6C8), Noelin including isoform 3 (UniProt Accession No. Q99784), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), Hornerin (UniProt Accession No. Q86YZ3), and combinations thereof,
   iii) constructing a protein biomarker signature for the subject, wherein the biomarker signature comprises the amount of the protein in the sample from the subject; and
   iv) comparing the amount of the protein in the sample from the subject to an amount of the protein in a reference sample, wherein a change in the amount of the protein in the sample from the subject relative to the amount of the protein in the reference sample is a prognosis of chronic kidney disease in the subject.
88. The method of paragraph 87, wherein the mass spectrometry is selected from the group consisting of SRM, MRM, PRM, DDA, DIA, LC-MS, LC-MS/MS, LC-SRM-MS, LC-MRM-MS, LC-PRM-MS, LC-DDA-MS, LC-DIA-MS, and combinations thereof.
89. The method of paragraph 87, wherein the subject is human.
90. The method of paragraph 87, wherein the sample is plasma.
91. The method of paragraph 87, wherein the reference sample is obtained from a control subject, wherein the control subject does not have chronic kidney disease.
92. The method of paragraph 87, wherein the reference sample is obtained from the subject before the subject is treated for chronic kidney disease.
93. The method of paragraph 87, wherein the reference sample is from a subject that has been successfully treated for chronic kidney disease.
94. The method of paragraph 87, further comprising administering a treatment to the subject.
95. The method of paragraph 87, further comprising:
   (a) administering a treatment to the subject;
   (b) obtaining a post-treatment sample from the subject;
   (c) detecting the at least one protein in the post-treatment sample from the subject according to the method of paragraph 87;
   (d) determining the amount of the protein in the post-treatment sample from the subject according to the method of paragraph 87; and
   (e) comparing the amount of the protein in the post-treatment sample from the subject to an amount of the protein in a reference sample, wherein a change in the amount of the protein in the post-treatment sample from the subject relative to the amount of the protein in the reference sample is indicative of the efficacy of the treatment.
96. The method of paragraph 95, wherein the reference sample is obtained from a control subject, wherein the control subject does not have chronic kidney disease.
97. The method of paragraph 95, wherein the reference sample is obtained from the subject before the subject is treated for chronic kidney disease.
98. The method of paragraph 95, wherein the reference sample is from a subject that has been successfully treated for chronic kidney disease.
99. A method for determining progression of chronic kidney disease in a subject, comprising:
   i) obtaining a sample from the subject;
   ii) detecting and determining an amount of at least one protein in the sample by at least one technique selected from the group consisting of mass spectrometry, antibody method, nucleic acid aptamer method, immunoassay, ELISA, immunoprecipitation, SISCAPA, Western blot, and combinations thereof; wherein the protein is selected from the group consisting of Uteroglobin (UniProt Accession No. P11684), Putative sodium-coupled neutral amino acid transporter 10 (UniProt Accession No. Q9HBR0), Protein AMBP (precusors of alpha-1 microglobulin) (UniProt Accession No. P02760), Aminopeptidase N (UniProt Accession No. P15144), C-reactive protein (CRP) (UniProt Accession No. P02741), Vasodilator-stimulated phosphoprotein (VASP) (UniProt Accession No. P50552), Cystatin-C (UniProt Accession No. P01034), Calreticulin (UniProt Accession No. P27797), Caspase-14 (UniProt Accession No. P31944), Collagen alpha-2(I) chain (UniProt Accession No. P08123), Insulin-like growth factor-binding protein 6 (UniProt Accession No. P24592), Neogenin (UniProt Accession No. Q92859), Corneodesmosin (UniProt Accession No. Q15517), Isoform C1 of Tight junction protein ZO-2 (UniProt Accession No. Q9UDY2), Neutrophil gelatinase-associated lipocalin (NGAL) (UniProt Accession No. P80188), Latent-transforming growth factor beta-binding protein 2 (UniProt Accession No. Q14767), Neural cell adhesion molecule 1 (NCAM1) (UniProt Accession No. P13591), Dermcidin (DCD) (UniProt Accession No. P81605), Thyroxine-binding globulin (SERPINA7) (UniProt Accession No. P05543), 6-phosphofructokinase muscle type (PFKM) (UniProt Accession No. P08237), BTP (Prostaglandin-H2 D-isomerase) (UniProt Accession No. P41222), Leukocyte immunoglobulin-like receptor subfamily A member 3 (LILRA3) (UniProt Accession No. Q8N6C8), Cystatin-B (UniProt Accession No. P04080), Plexin domain-containing protein 2 (UniProt Accession No. Q6UX71), EMILIN-2 (UniProt Accession No. Q9BXX0), and combinations thereof;
  iii) constructing a protein biomarker signature for the subject, wherein the biomarker signature comprises the amount of the protein in the sample from the subject; and
  iv) comparing the amount of the protein in the sample from the subject to an amount of the protein in a reference sample, wherein a change in the amount of the protein in the sample from the subject relative to the amount of the protein in the reference sample is indicative of progression of chronic kidney disease in the subject.
100. The method of paragraph 99, wherein the mass spectrometry is selected from the group consisting of SRM, MRM, PRM, DDA, DIA, LC-MS, LC-MS/MS, LC-SRM-MS, LC-MRM-MS, LC-PRM-MS, LC-DDA-MS, LC-DIA-MS, and combinations thereof.
101. The method of paragraph 99, wherein the subject is human.
102. The method of paragraph 99, wherein the sample is plasma.
103. The method of paragraph 99, wherein the reference sample is obtained from a control subject, wherein the control subject does not have chronic kidney disease.
104. The method of paragraph 99, wherein the reference sample is obtained from the subject before the subject is treated for chronic kidney disease.
105. The method of paragraph 99, wherein the reference sample is from a subject that has been successfully treated for chronic kidney disease.
106. The method of paragraph 99, further comprising administering a treatment to the subject.
107. The method of paragraph 99, further comprising:
  (a) administering a treatment to the subject;
  (b) obtaining a post-treatment sample from the subject;
  (c) detecting the at least one protein in the post-treatment sample from the subject according to the method of paragraph 99;
  (d) determining the amount of the protein in the post-treatment sample from the subject according to the method of paragraph 99; and
  (e) comparing the amount of the protein in the post-treatment sample from the subject to an amount of the protein in a reference sample, wherein a change in the amount of the protein in the post-treatment sample from the subject relative to the amount of the protein in the reference sample is indicative of the efficacy of the treatment.
108. The method of paragraph 107, wherein the reference sample is obtained from a control subject, wherein the control subject does not have chronic kidney disease.
109. The method of paragraph 107, wherein the reference sample is obtained from the subject before the subject is treated for chronic kidney disease.
110. The method of paragraph 107, wherein the reference sample is from a subject that has been successfully treated for chronic kidney disease.

Various embodiments of the present invention are described in the ensuing examples. The examples are intended to be illustrative and in no way restrictive.

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention.

The invention will be further explained by the following examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Without being bound by theory, in-depth proteomics discovery is used to identify novel plasma biomarkers that are useful for the prognosis for development of chronic kidney disease (CKD) and to monitor progression (severity) of CKD. Furthermore, a subset of markers are related to key signaling pathways underlying the disease.

Methods. A four group design in which 64 plasma samples collected at two time points (T0 and T1) for 16 cases and 16 controls were analyzed. Cases were individuals with GFR slope>5 ml/min/year and a total decline of at least 30 ml/min/year follow-up of at least 3 years while the controls consisted of individuals with <1 ml/min/year for at least 3 years matched by age, sex, race, diabetes, hypertension, GFR (Glomerular Filtration Rate) at T0, ACR (Albumin-to-Creatine Ratio). Each sample was depleted of the top 14 abundant plasma proteins, fractionated using reversed phase HPLC, digested, analyzed by mass spectrometry and batched searched. Proteins were ranked based on p values for prognosis (cases and controls at T=0) and severity (cases between T0 &T1/controls between T0 &T1) and determined pathways between the various candidate markers.

Results. Across all plasma samples, 1151 nonredundant proteins were identified with a protein and peptide probability of <0.1% (with >625,000 spectral counts). There were 3 and 43 candidate prognostic markers that were found to have $p<0.01$ and $p<0.05$, respectively. Within this top group of severity markers were APO II, APO CIII, Haptoglobin and APOL1 which were ranked $4^{th}$ (p=0.0058), #6 (p=0.011), $13^{th}$ (p=0.018) and $19^{th}$ (p=0.021), respectively for prognosis. There were 2 and 66 candidate severity markers with $p<0.01$ and $p<0.05$, respectively. Of these CRP, Cystatin C and beta trace protein were ranked $6^{th}$(p=0.004), $7^{th}$ (p=0.006) and $18^{th}$ (P=0.04), respectively, as severity markers. Interestingly, the TGF beta pathway proteins was enriched in the candidate severity proteins (p<0.05) based on over 15 protein linkages. Although TGF beta 1 was identified in this data set, 90% of the data was missing.

This example indicates that de novo proteomic analysis of plasma can be used to confirm changes of known biomarkers and to identify potential new biomarkers. This example also shows that different plasma proteins may be aligned with prognosis versus severity. Furthermore, proteins in the TGF beta pathway are particularly enriched as candidate severity biomarkers.

Example 2

Based on the results from the de novo proteomic discovery in blood from a Chronic Renal Insufficiency Cohort (CRIC) Study (see Example 1 herein), we 1) develop targeted assays, for example either multiple reaction monitoring (MRM) or ELISA, for the "top 20-30 hits" for chronic kidney disease (CKD) prognosis and progression protein biomarkers; and 2) verify and validate these "hits". The most promising potential biomarkers (top hits) are internally validated with a case-control study in a separate sample of the CRIC Study Background and Rationale. The most common serum biomarker is serum creatinine and its derivative, estimated GFR (Glomerular Filtration Rate). Estimated GFR is a strong predictor of CKD progression with recent meta-analyses showing consistency of association across a broad range of causes. However, improvements are needed to better discriminate between people who do versus who do not progress to kidney failure (prognostic markers) to provide risk predictors as well as refine estimates of CKD progression and targets for clinical trials (progression markers including low molecular weight filtration markers like creatinine and cystatin C) to make clinical trials more efficient.

The design of the proteomic discovery study is described in the Example 3 herein and is shown in the schematic (FIG. 1). Based on this design, potential prognostic markers were determined based on differences between cases and controls at baseline (T0). Potential progression markers were determined based on differences over time (T0 vs. T1) in cases. The unbiased and efficient approach identified and quantified ~1,551 non-redundant proteins. Notably, multiple known proteins associated with CKD were found to differ between groups in the discovery experiment. These positive controls provide face validity to the discovery methodology. Table 3 lists several of these key representative proteins (Tables 1 and 2 ranked lists). Importantly, many of the identified proteins had not been previously associated with CKD prognosis and progression (novel "top hits").

This study performs targeted verification and the validation of markers that have been identified in the de novo proteomics discovery phase. A subset of top candidate markers are selected based on statistical and biological criteria and review for verification and the validation.

TABLE 3

Representative proteins with known CKD associations observed in discovery "top hits"

| Type of marker | Protein | Rank and p-value |
|---|---|---|
| Progression: Known filtration marker proteins - "positive controls" for progression design (cases T1 vs T0) | Cystatin C | #7 (p = 0.006 for progression) |
| | Beta-trace protein (BTP) | #21 (p = 0.014 for progression) |
| | Beta-2 microbglobulin | Not "seen" among 1551 proteins |
| Prognosis: Known risk relationships HDL is associated with CKD prognosis | Apo AII | #4 (p = 0.006 for prognosis) |
| | Apo CIII | #7 (p = 0.011 for prognosis) |
| Prognosis: Novel & post-hoc very interesting: APOL1 ( CKD genetic susceptibility) | APO L1 | #19 (p = 0.021 for prognosis) |
| Marfans disease has rare forms of kidney disease | Fibrilin-1 | #2 (p = 0.0048 for prognosis) |
| CD59 glycoprotein - complement attack complex; elevated urine levels in membranous GN | CD59 glycoprotein | #3 (=0.005 for prognosis) |
| Heme binding antioxidant with isoforms related to diabetic complications including CKD prognosis in DCCT/EDIC | Haptoglobin | #13 (p = 0.018 for prognosis) |
| Prognosis: Novel with respect to CKD | Fructose-bisphosphatealdolase A | #1 (p = 0.002 for prognosis) |

Assays are identified and developed for measurement of these novel biomarkers. Candidate blood markers identified in the discovery phase are verified and validated.

A subset of novel biomarkers identified in the Discovery Phase are measureable with assays appropriate for large-scale use.

These markers are verified in CRIC participants (internal validation) and validated (initial external validation). Through this sequential cohort analysis, a limited panel of candidate markers provide a limited panel of candidate markers that are subsequently tested in other larger validation datasets.

Methods and Approaches.

Overall approach. Biomarker development comprises various steps. These are discovery, targeted assay validation (involving development and testing of the quantitative assays for each candidate proteins), verification and validation (carried out in various well phenotyped clinical cohorts). During each step, the number of candidate markers is reduced. After initial external validation, the number of biological samples (cohort size) is increased to test one or more biomarkers that can be used for diagnosis, prediction or as a target for therapy.

Selection of candidates biomarkers appropriate for verification and validation.

Table 3 and Table 1 and Table 2 list the candidate protein biomarkers for both prognosis and progression. The selection of candidate biomarkers is based on statistical significance as well as knowledge about their biological and pathophysiological roles in CKD. Our unbiased de novo discovery effort yielded interesting candidate biomarkers—among the very top hits listed in Table 3 are proteins whose blood levels were not previously known to be informative for CKD (APOL1 and fibrillin), a pathway (Complement—CD59 glycoprotein), and a protein (Haptoglobin). Progression "top hits" are quite interesting with the top one (Uteroglobin) being stronger than cystatin and having low molecular weight and low missing rate.

Data mining of discovery mass spectroscopy (MS) data set using peptide analysis: Reanalysis of the data using each individual peptide (>19,000) allows us to determine if there are regions or modified forms (e.g. degraded or processed forms; phosphorylated forms) of a protein are more significant than total protein. Use of these modified forms reflect disease processes, thereby increasing specificity of the protein that is assayed. This information is used to develop expanded quantitative assays for determining total protein concentration as well as the modified forms.

Network analysis of potential candidates: We assess the pathways and interconnections between the various candidate biomarkers to better understand the biology of the identified proteins. For example, using Ingenuity Pathways Analysis (IPA, Ingenuity Systems, Redwood City, CA) we found that the TGFbeta pathway was associated with CKD in our proteomic discovery efforts.

Quantification of candidate biomarkers in verification/validation study populations.

In various embodiments, the candidate proteins observed in the Discovery Phase using mass spectrometry are quantified by MRM. In various embodiments, ELISA is tested for specificity and sensitivity to ensure accuracy and agreement with initial discovery results (verification phase). In various embodiments, assays for verification and/or validation are selected from ELISA methods or MRM methods Note that a positive result of the discovery data by an ELISA is confirmatory. However, a negative or neutral result by ELISA is not sufficient to rule-out a candidate biomarker due to possibility of modified forms of the protein that are not detected or quantified by the ELISA is the "true" candidate. To address this, we investigate peptide and potential known modifications and can develop the appropriate MRM assays that capture these forms.

Statistical analysis. We use advanced statistical methods to further analyze the discovery cohort (as outlined above). We expand this to tryptic peptide analysis as outlined above. For verification and validation, the analysis is more straightforward with case-control comparisons using t-tests and non-parametric Wilcoxon rank-sign tests, adjustment using logistic regression for residual confounding after the matching. Meta-analysis across cohorts is conducted using random effects meta-analysis. Larger sample sizes enable us to evaluate prediction statistics as well but the novelty of these discovery markers suggests a stepwise approach to evaluation as knowledge about the assay and discriminatory performance matures. This is the same for data obtained from ELISA and MRM assays.

Validation Multiplexed. A robust targeted mass spectrometry MRM-MS multiplex assay has been developed for selected candidates. Sample processing: Samples are thawed on ice, and centrifuged to remove particulates. Samples are aliquoted if needed. All subsequent sample-processing steps are performed on the NXP automation workstation which is completely hands-free.B-Gal are added to the samples. Samples undergo denaturation, reduction/alkylation and trypsin digestion on the NXp workstation. Digestions are quenched and N15 labeled peptides are added as internal standards. LC-MS/MS analysis: A Prominence UFLCXR HPLC system (Shimadzu) coupled to QTRAP® 6500 system (SCIEX) is used. Analyst software version 1.6.2 is applied to control the LC-MS/IS system and for data acquisition. Digested samples and N15 labeled peptides are separated on an Xbridge BEH30 C18 2.1 mm×100 mm, 3.5 µm column (Waters) maintained at 40° C. The mobile phase consists of A: 2% ACN, 98% water 0.1% formic acid in water and B: 95% ACN (containing 0.1% formic acid) and the AB gradient is delivered at a flow rate of 0.25 ml/min. A two-phase switching valve is used for desalting and to divert the post-column eluent before entering the ion source of the MS instrument.

Example 3

Verification and Validation. Identified Candidate Markers. Data was collected from a retrospective matched case-control study of kidney disease; 16 pairs of case/controls subjects are considered. All subjects had chronic kidney disease (CKD) at baseline. A case subject is defined as a subject who progressed substantially, while a control subject is one who has not. Progression was defined as individuals meeting 3 criteria: slope>5 ml/min/1.73 $m^2$ per year; total decline of at least 30 ml/min/1.73 $m^2$; follow-up of at least 3 years. As such cases progressed from early CKD Stage 3 (eGFR>45) to late CKD Stage 4-5 (eGFR<30). Blood samples were assayed from two different time points (baseline and end of follow-up) to uncover proteins that predict rapid progression as well as consequences of progressive CKD. See FIG. 1 for study design.

Among the assayed samples, 1551 protein groups were measured. Selection criteria for candidate markers appropriate for further verification and validation is based on comparisons made across groups (progressors vs. non-progressors) to assess for novel biomarkers for prognosis (comparing T0 of cases vs controls) and progression (comparing the change between T0 and T1 for cases) (see FIG. 1). We used several methods to analyze the results. We rank candidate markers based on the more conservative Wilcoxon paired sign rank test on the log counts. Below we show those values as well as the values from the random effect models. For those proteins with p values less or equal to 0.05 using the Wilcoxon sign rank test are potentially investigated if there is additional biological reasons to do so (considered to be tier 2 analytes). Table 1 and Table 2 list representatives of the top candidate proteins for prognosis and progression, respectively.

Of note, the number of positive "hits" exceeds levels expected from multiple comparisons. A total of 310 proteins detected at least 50% of the time would yield 3 at $p<0.01$ and 16 at $p<0.05$ if the null hypothesis was true. Our analyses exceeded this number. Our progression analysis (T1 vs. T0 in cases) had 12 hits at $p<0.01$ and 66 hits at $p<0.05$. Our prognostic analysis (cases vs. controls at T0) had 3 and 43, respectively. In comparison the change in controls (T1 vs. T0 in non-progressors) only has 1 and 21.

Example 4

CKD Blood Biomarker Verification and Validation
1. Rationale.

This protocol will focus on verification and validation following discovery efforts to identify novel blood biomarkers. The most common serum biomarker used to indicate progression of CKD is serum creatinine and its derivative, estimated GFR. Estimated GFR is a strong predictor of CKD progression with recent meta-analyses showing consistency of association across a broad range of causes. However, it is not able to adequately discriminate between people who do versus who do not progress to kidney failure, requiring large and expensive clinical trials to study treatments for kidney failure, and less cost effective prevention strategies.

with 16 individuals with stable GFR (<1 ml/min/year for at least 3 years). Two time points per individual. Quantitative assessment entails i) the selection of the top candidate biomarkers, ii) assessment of existing ELISA assay, iii) development of mass spectrometry (MS) based-multiple

TABLE 5

Representative known markers observed in discovery cohort analysis

| Protein | Type of marker | Best Rank for the known protein (#1 = top statistical discovery protein) |
| --- | --- | --- |
| Cystatin C | "positive controls" for severity design | #7 (p = 0.006 in severity) |
| Beta-trace protein (BTP) | (cases T1 vs T0) as they are known | #18 (p = 0.014 in severity) |
| Beta-2 microbglobulin | filtration markers | Not "seen" among 1551 proteins |
| APO L1 | Progression known to be related to APOL1 genotype | #19 (p = 0.021 in prognosis) |
| Apo AII | Progression known to be associated | #4 (p = 0.0058 for prognosis) |
| Apo CIII | with HDL levels (APOL1 also HDL bound) | #6 (P = 0.011 for prognosis) |
| Fibrilin-1 | Marfans disease and rare forms of kidney disease | #2 (p = 0.0048 for prognosis) |
| Haptoglobin | Heme binding antioxidant with isoforms related to diabetic complications including CKD progression in DCCT/EDIC | #13 (p = 0.018 for prognosis) |
| CRP | Known to be associated with CKD as a risk factor and consequence | #7 (p = 0.004) for severity #128 (p = 0.15) for prognosis |

Figure 2:
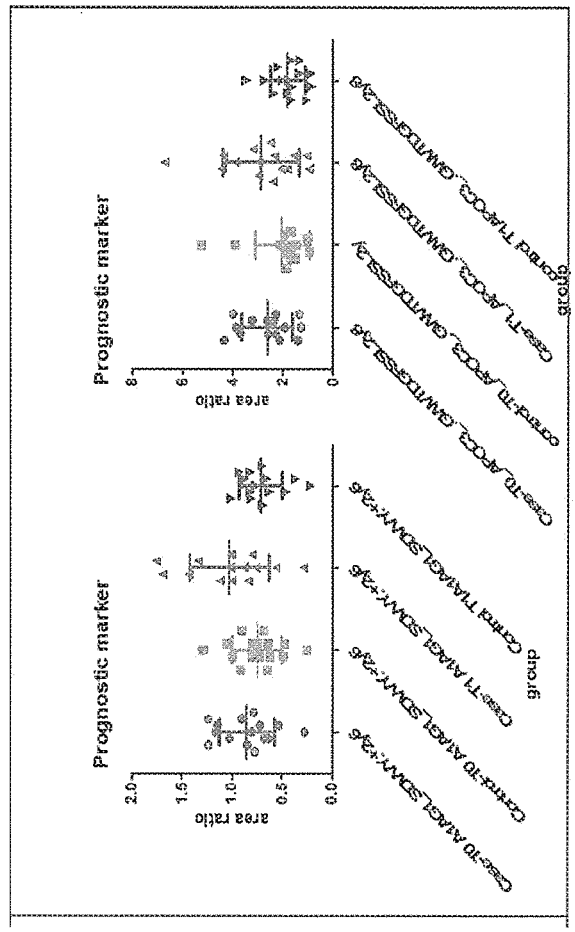
FIG. 2 depicts in accordance with various embodiments of the invention validation of A1AG1 (alpha-1-acid glycoprotein 1) and APOC3 (apolipoprotein CIII) protein expression in 16 controls and 16 CKD at both T0 and T1 time points using targeted MRM assays. For ApoCIII, (peptide GWVTDGFSSLK) (SEQ ID NO: 1) and A1AG1 (peptide SDVVYTDWK) (SEQ ID NO: 2), the Stable Isotope Labelled (SIL) Peptides were used to normalize the expression. The protein quantitation was calculated by ratio (Ratio=native light peak area/SIL heavy area). 16 case and 16 controls are indicated as well as the two time point. Both proteins have elevated expression at T0 in 16 cases in comparison to 16 controls.

To date, a biomarker discovery proteomic pipeline was developed where each step in the process was carefully assessed to ensure high quality and performance, was carried out on carefully selected biosamples at the extremes of CKD progression spectrum (very rapid vs. stable; 64 samples on 16 cases & 16 controls at baseline & follow-up) to provide new candidate biomarkers for prognosis, severity (progression) and as potential therapeutic targets in CKD (Discovery Phase, see FIG. 2 for study discovery study design). Known proteins were observed and found to differ between groups (Table 5). Each of the known protein was significant only for one type/class of biomarker. Importantly, many proteins that to date had not been associated with CKD prognosis and severity were also found to differ between groups. Using novel statistical approaches, top candidate markers have been selected for potential verification and the validation. Verification and the validation of these promising markers that have been identified from the de-novo proteomics discovery in the current protocols.

2. Specific Aims.

The development of MS based assays, where needed, which could be used for faster and more precise measurement of these novel biomarkers. Verification and validation of the novel blood markers identified in the discovery phase in individuals where altered levels precede or follow rapid CKD progression in different individuals from the same cohort and in additional cohorts starting with 16 case-control sets per cohort as in the discovery phase and increasing to 200 case-control sets.

Approach:

This involves testing the candidate biomarkers through de novo proteomic discovery in 32 individuals from CRIC. In the current verification and phases, we measure the most promising candidate biomarkers proceeding (progression markers) and following (severity markers, some marking low filtration) rapid CKD progression in a second case control study from CRIC for verification of the initial results. For CRIC we use the same design as in the discovery study. Cases will include 16 individuals who had had a rapid decline (slope>5 ml/min/year, total decline of at least 30 ml/min, and follow-up of at least 3 years) in GFR compared reaction monitoring (MRM) assays for the other top candidate biomarkers, iv) and the subsequent use of both ELISA and MRM assays for the quantification of these analytes in the two selected cohorts. The most promising markers obtained from these early verification stages, we use to measure the candidate biomarkers in larger samples from other cohorts for further validation and determination of clinical utility.

Without being bound by theory, a subset of novel biomarkers identified in the Discovery Phase in CRIC are verified in a separate set of CRIC participants who have similarly rapid CKD progression. This provides a limited panel for the accurate prognosis and assessment of progression that can be subsequently tested for clinical utility. Furthermore, these proteins identify novel pathological mechanisms involved in CKD which can be targeted for therapeutic strategies.

3. Background.

In biomarker development there are various steps. These are discovery, verification and validation. In the latter two steps, candidate biomarkers are quantified in ever increasing cohort sizes. In other fields, verification is termed replication. In each subsequent test cohort the number of candidate markers are reduced leading, ultimately to a final panel for diagnosis, prediction or targets for therapy. In this protocol we verify the candidate biomarkers a separate CRIC cohort. As such, the initial verification in CRIC is equivalent to internal validation. These analyses will be followed by validation in selected samples from other CKD studies. There are two common approaches to verify and validate candidate biomarkers that have sufficient quantification capabilities. These are i) specific antibody based immunological ELISA and ii) mass spectrometry (MS) based MRM and SRM assays both methods provides protein concentration. MRM is based on determining the concentration of a prototypic peptide(s) comprised of an amino acid sequence that is unique to the target protein(s) in a complex protein digest. The selected peptide(s) is separated in the MS instrument (in this instance, a Triple Quadrupole instrument), and broken down into its resulting fragments (each one is called a transition). Two or three unique peptides (each with multiple transitions) are measured and compared to a spiked synthetic peptide that has a $^{15}N$ amino acid (the labeled peptide is heavier than the endogenous peptide). Since the concentration of the $^{15}N$ labeled peptide is known, the quantity of the endogenous peptide, and thus, the concentration of the endogenous protein can be determined.

4. Preliminary Data.

Figure 3:
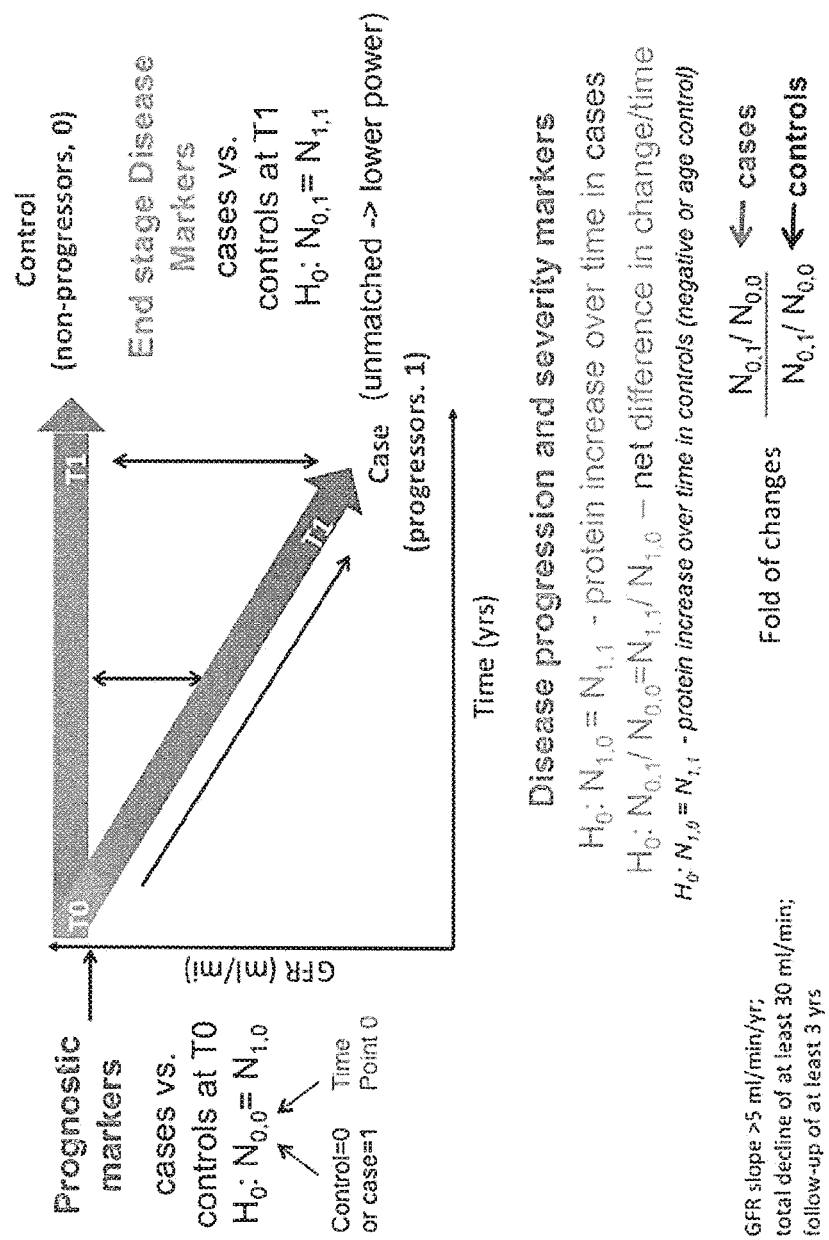
FIG. 3 depicts in accordance with various embodiments of the invention, a schematic representation of cohort design for CKD discovery (and verification/validation). Comparison of cases and controls at time 0 (baseline) will yield candidate prognostic markers while comparison of changes over time will yield candidate progression markers. Filtration and or severity markers can be potentially obtained by comparison at T1 of cases and controls.
Figure 4:
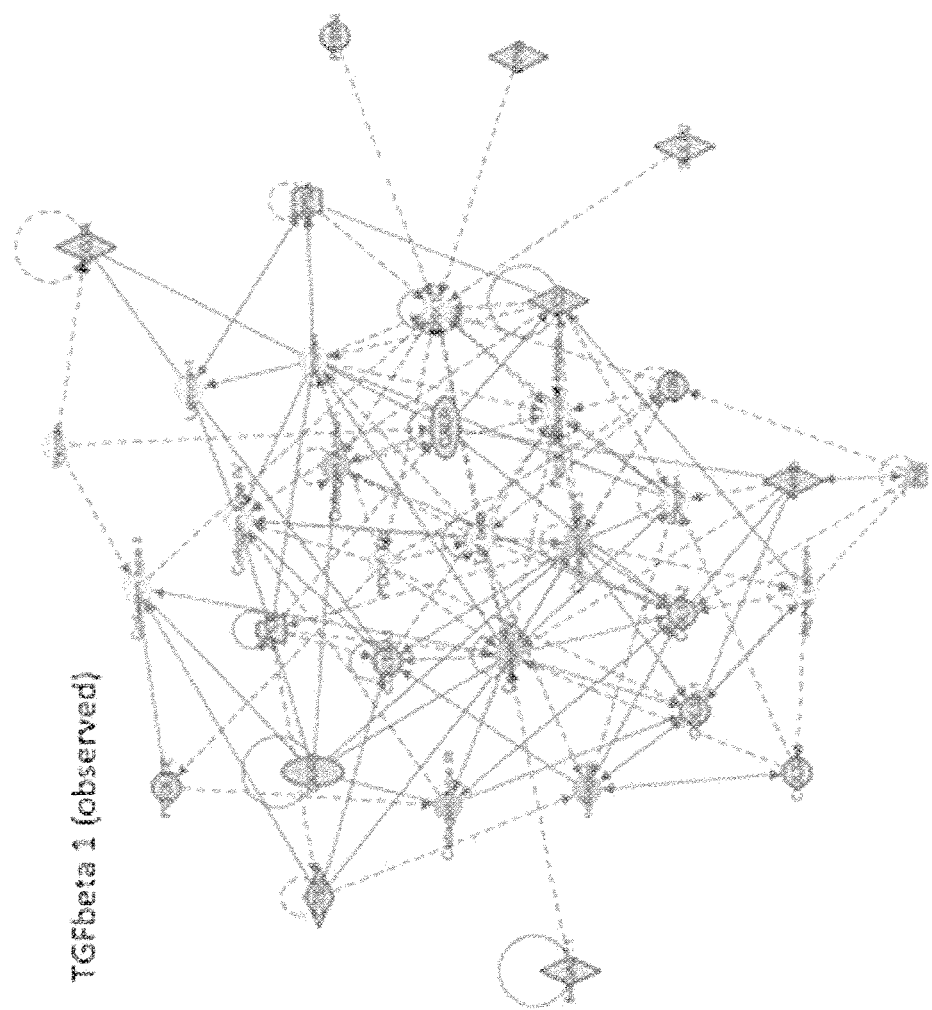
FIG. 4 depicts in accordance with various embodiments of the invention, Ingenuity pathway analysis of top candidate severity (progression) biomarkers (p<0.05) found TGF-beta as primary pathway.

4a. Identification of Novel Blood Biomarkers where Altered Levels Precede or Follow Rapid CKD Progression Using State-of-the-Art Proteomic Methods in a Discovery Phase.

i. Cohort Selection Criteria:

De novo proteomic discovery was carried out on 32 individuals from the CRIC cohort. Specifically, cases comprised 16 individuals with rapidly progressive CKD meeting 3 criteria: slope>5 ml/min/year; total decline of at least 30 ml/min; follow-up of at least 3 years. Cases progress from early CKD Stage 3 (eGFR>45) to late CKD Stage 4-5 (eGFR<30). These requirements assured consistently progressive CKD with a substantial and rapid progression. As such, cases progress from early stages of CKD where risk of adverse outcomes is relatively low to late stages of CKD where risk of complications is very high. The rationale for defining cases by multiple criteria was done to increase specificity and ensured that we included the extreme cases based on the following rationale. The rate of change of >−5 ml/min/year was chosen to be steeper than average for most CKD cohorts. This rate of change was determined by review of the progression rate in several CKD cohorts and clinical practice recommendations. Controls consisted of 16 individuals with stable GFR (decline<1 ml/min/year for at least 3 years). Controls were matched on cohort based on age, sex, race, diabetes and hypertension. Both diabetics and non-diabetic participants in CRIC to ensure representation across this important risk factor of CKD. The selection of cases and controls for the discovery cohort was reviewed in order to rule out any cases within CRIC with acute kidney injury. All serum creatinine, measured and estimated GFR on potentially eligible cases and controls were examined and cases with a clear progressive course were chosen as well as controls with clearly stable kidney function. Blood pressure control and antihypertensive medication were compared for comparability. All pairs were very tightly matched.

ii. Study Design:

Blood samples were assayed from two different time points (baseline and end of follow-up) to uncover proteins that predict rapid progression as well as consequences of progressive CKD. See FIG. 3 for study design.

iii. Discovery Pipeline and Quality Control:

The discovery pipeline consists of affinity depletion of the top 14 abundant plasma proteins, desalting and fractionation of intact low abundant proteins (flow through from the depletion column) using reversed phase HPLC into 12 fractions. Each fraction was neutralized, denatured, and digested with trypsin prior to analysis on the Orbitrap ELITE mass spectrometer (Thermo). Quality control was carried out at each step. Samples that deviated were rerun in their integrity. Each case and its matching control was blocked and run as group with baseline (T0) run prior to the subsequent sample (T1). Samples within block were randomized, as were the 16 blocks. MS spectra was analyzed using OSMMA and X!Tandem search engines on PASS platform (Integrated Analysis). Isoforms must have at least one peptide to an amino acid sequence that is unique to a particular isoform. Uncharacterized or hypothesis proteins are researched using BLAST to ensure there is no common name. A total of 1551 non-redundant proteins (protein groups) were identified with a protein and peptide probability of <0.1% with over 625,000 spectral counts.

iv Statistical Analyses:

Data was collected from a retrospective matched case-control study of kidney disease; 16 pairs of case/controls subjects are considered. All subjects had Chronic Kidney Disease (CKD) at baseline. A case subject is defined as a subject who progressed substantially, while a control subject is one who has not. For each subject blood is sampled at 2 visits and the weighted counts of 1351 protein groups are measured. Thus, for each protein group the data consists of 16 independent vectors of weighted protein counts for the following combinations control/baseline, control/visit 2, case/baseline, and case/visit 2. We modeled the protein counts directly. Let $y_{ijt}$ be the protein counts for case/control set i, case j (case is j=1, control is j=0) at visit t (baseline visit is t=0, visit 2 is t=1). We propose to fit the following random-intercept mixed effects model $$\log(y_{ijt}) \sim N(\mu_{ijt}, \sigma_y^2), i=1,2,\ldots,11; j=0,1; t=0,1$$

$$\mu_{ijt} = a_i + \alpha_c I\{j=1\} + \alpha_v I\{t=1\} + \alpha_{cv} I\{j=1 \& t=1\}$$

where $a_i \sim N(0, \sigma_r^2)$ are the random intercepts accounting for within-group correlation, $\alpha_c = \mu_{i10} - \mu_{i00}$ is the baseline (t=0) difference between the means of the cases and controls, $\alpha_v = \mu_{i01} - \mu_{i00}$ is the mean change from baseline to visit 2 among controls (j=0), and $\alpha_v + \alpha_{cv} = \mu_{i11} - \mu_{i10}$ is the mean change from baseline to visit 2 among cases (j=1). Thus, $\alpha_{cv}$ is the difference between the change of cases and controls from baseline to visit 2. Thus, we can test $H_0: \alpha_{cv} = 0$ versus $H_A: \alpha_{cv} \neq 0$ using either mixed effects or generalized estimating equation (GEE) approaches. For the missing values we propose to set $y_{ijt} = 0.5$.

Given the large number of missing observations across protein groups, we add an additional model that can detect group differences in the probability of having observations below the limit of detection. An interesting hypothetical example is that of a protein group that is detectable in every sample both in cases and controls at baseline, is detectable in all controls at visit 2 but is not detected in any case at visit 2. Obviously, this would be a very important protein group to detect. In practice, such an example would be very rare, or impossible to find, but finding protein groups with unusual missing patterns is highly relevant. Thus, we propose a missing model approach (missingness approach) that complements the observed protein count model introduced above. With the same notation, let $r_{ijt}$ be the binary variable indicating whether protein counts are observed for case/control set i, case j (case is j=1, control is j=0) at visit t (baseline visit is t=0, visit 2 is t=1). The missing data model is:

$$r_{ijt} \sim \text{Bernoulli}(0, p_{ijt}), i=1,2,\ldots,11; j=0,1; t=0,1$$

$$\log it(p_{ijt}) = b_i + \beta_c I\{j=1\}) + \beta_v I\{t=1\} + \beta_{cv} I\{j=1 \& t=1\}$$

where $b_i \sim N(0, \sigma_b^2)$ are the random intercepts accounting for within-group correlation, $\beta_c = \log it(p_{i10}/p_{i00})$ is the relative log odds of missing data at baseline (t=0) between cases (j=1) and controls (j=0), $$\beta_v = \log it\left(\frac{p_{i01}}{p_{i00}}\right)$$

is the relative log odds among controls (j=0) of missing data between the baseline visit (j=0) and visit 2 (j=1), and $$\beta_v + \beta_{cv} = \mathrm{logit}\left(\frac{p_{i11}}{p_{i10}}\right)$$

is the log odds of missing data between baseline (t=0) and visit 2 (t=1) among cases (j=1). Thus, $$\beta_{cv} = \mathrm{logit}\left(\frac{p_{i11}}{p_{i10}}\right) - \mathrm{logit}\left(\frac{p_{i01}}{p_{i00}}\right)$$

is the difference between the relative log odds of missing data for visit 2 versus baseline visits among cases and controls. We can test $H_0: \beta_{cv}=0$ versus $H_A: \beta_{cv} \neq 0$ using either mixed effects or generalized estimating equation (GEE) approaches.

v. Data Quality:

It is noteworthy that this novel statistical analysis used random effects models to quantify the evidence, going beyond usual analyses in proteomic discovery. Also, in the number of positive "hits" exceeds levels expected from multiple comparisons: 310 proteins detected at least 50% of the time would yield 3 at $p<0.01$ and 16 at $p<0.05$ if the null hypothesis was true; our severity analysis (T1 vs. T0 in cases hypothesized to have the greatest power due to the design & biology—low filtration elevates many low molecular weight proteins) had 12 hits at $p<0.01$ and 66 hits at $p<0.05$; our prognostic analysis (cases vs. controls at time 0) had 3 and 43 and our progression analysis (differences at T1) had 8 and 45; in comparison the change in controls (T1 vs. T0 in non-progressors) only has 1 and 21.

vi. Initial Selection Criteria:

Selection criteria for candidate markers based on comparisons made across groups (progressors vs. non-progressors) to assess for novel biomarkers for prognosis (comparing T0 of cases vs controls) and severity (progression) (comparing the change between T0 and T1 for cases vs controls). In addition, we investigate the possibility of filtration markers by comparing the T1 of cases vs controls of proteins with molecular weight below 10 kDa (see FIG. 3). As well, we compare signals made across groups (progressors vs. non-progressors at time 0) to assess for novel biomarkers for progression. As well, we compare signals within the group of progressors over time, compared to the non-progressors (severity T1 vs. T0 in cases). An increase or decrease in signals in the progressors but not in the non-progressors may either be secondary to decreased filtration or other consequences of CKD. As described in the background it is reassuring that the number of hits ($p<0.05$) exceeds the expectations under the null hypothesis with the most hits in the contrasts through to have the most power (severity) and the least hits in the controls.

Top candidate proteins for prognosis and progression with p value of less or equal to 0.01-0.15 are verified. For those proteins with p values less or equal to 0.05 are investigated if there is additional biological reasons to do so (considered to be tier two analytes). See tables 6 and 7 for representatives of the top candidate proteins for prognosis and severity, respectively. There are a number of known makers of CKD (table 5 and bold in tables 6 and 7) that are also found in this discovery cohort, but it is worth noticing that there are numerous other candidates with lower p values. Table 8 lists number of potential candidates that meeting, at this time, these criteria.

4b. Development of High Through Put Sample Processing for MRM Assays.

A robot (Biomek NX$^P$) that uses a 96 well plate format to carry out the core sample processing steps required for MRM. These include protein denaturation, reduction, alkylation and trypsin digestion. Testing of this system using standards protein and N$^{15}$ labeled peptides in plasma has shown that this step has % CV of less than 5% over many plates. The desalting step which is required prior to MS analysis is traditionally carried out using reversed phase chromatography either in a pipet tip or a 96 well format. Experiments showed that this step (using either format) had % CV of over 15%. To reduce the error and irreproducibility of the desalting step, it was determined that this could happen on the reversed phase column on the MS instrument. Therefore, we now load the digested sample (which contains salt) onto the LC MS instrument but divert the flow through (salt) using a value set up prior the MS. Once the salt is through the system, the value is returned so that as the gradient is started the peptide flow directly into the MS instrument. Together the sample processing and analysis using desalting online, lead to a CV % of less than 10%. This system allows us to reproducibly process a minimum of 96 samples per day.

TABLE 8

| Type of candidate marker | # with $p < 0.01$ | # with $p < 0.05$ |
| --- | --- | --- |
| Prognostic | 3 | 43 |
| Severity (Progression) | 12 | 66 |

These numbers many change a more refined data analysis is completed

5. Methods and Approaches.

5.a. Further Exploration of the Discovery MS Data Set Using Peptide Analysis:

Due to the high quality and extensiveness of the MS discovery data set we continue to mine for biological and pathophysiological insights in addition to finding additional important markers (primarily looking for new markers to other pathways which may expand individualization of these proteins within the clinic). This entails reanalyzing the data using Missingness approach using each individual peptide (~9000). This allows us to determine if there are regions or modified forms of a protein which is more significant than total protein. These modified forms can reflect disease processes.

5.b. Network Analysis of Potential Candidates.

To further add value to the discovery analysis, it can be useful to assess the pathways and interconnections between the various candidate markers. To do this, we 1 use a number of proteomic analysis including Ingenuity Pathways Analysis (IPA) (Ingenuity Systems, Redwood City, CA). In our preliminary analysis carried out on a subset of discovery cohort, the TGF beta pathway was indicated. Although TGFbeta 1 was identified in this dataset, 90% of the data was missing. TGF beta isoforms 2 and 3 are present at even lower concentrations in blood. We have an immuno-MRM assay for all 3 TGFbeta isoforms that can be used.

5.c. Verification of Candidates.

Strategy:

Quantification of candidate biomarkers in verification/validation study populations: We use ELISA and/or MRM assays and/or clinical chemistry assays as needed. Immuno assays and MRM assays will be checked for reliability, validity with reproducibility, CV % and LLOD, LLOQ determined in pooled matrix. Samples are randomized and individuals involved in sample handling, running and analysis are blinded. Below outlines the cohort and assay design.

5.c.1. Study Populations and Samples to be Assayed.
Verification Study Populations:

Initial verification is performed in case-control studies of CRIC and participants using the same design as the discovery (16 cases-control pairs*2 time points=64 samples) from each study (128 samples). Each pair has a baseline and last sample so we can again test for both progression and severity markers in an efficient balanced design with rigorous control using same criteria as used in the discovery studies as outlined below.
  i. Sample collection handling and storage were performed under standardized conditions and there is adequate volume for proteomic discovery.
  ii. Marked contrast between cases and controls. Cases are people who progress from early stages of CKD (where risk of adverse outcomes is relatively low) to late stages of CKD (where risk of complications is very high).
  iii. Limited heterogeneity among the cohorts. We replicate in CRIC where discovery was done. We expect to move onto other CKD cohorts subsequently.
  iv. Matching of cases and controls: Controls are matched to cases on a 1:1 basis using the same criteria that was used in the Discovery Phase case control study (see original discovery protocol D and section 4a above). As in selection of cases and controls for the discovery phase, we review of cases and controls to rule out cases with acute kidney failure episodes. All serum creatinine, measured and estimated GFR on potentially eligible cases and controls is examined by the and cases with a clear progressive course are chosen as well as controls with clearly stable kidney function. We also examine data on blood pressure control and anti hypertensive medication for comparability. We control for these risk factors to the extent possible statistically, particularly in verification studies, rather than by matching.

This initial verification work is useful to confirm assay performance in the cohort samples (include CKD, older age etc.) and look for initial signal. Markers with a suggestion of supportive validation (p<0.20) continue to the next phase. Other markers are scrutinized. Following this initial verification, we continue to later stage validation. We measure the most promising biomarkers in additional cohort of intermediate size samples Study designs are:

5.c.2. MRM Assays.

We perform MRM development, characterization, sample processing, running of samples and analysis. This lab uses either a 5500 or 6500 Q Trap with Turbo V Source with two or one XRMPX LC-20AD HPLC system (Shimadzu), that has flow rate of 100-200 µL/min with a normal run time of 15-30 min. This instrument configuration has exceptional stability, speed and potentially sensitivity that is required for clinical sample analysis. With this instrument we obtain excellent inter and intra-assay CV of ~2%, LLOD (which is peptide dependent) of 0.1 fmole and dynamic range of 10e6 to 10e7.

i. MRM Assay Development.

There are a number of steps involved in assay development. Briefly, the process of establishing an MRM assay consists of several steps: 1) selection of peptide(s) unique to the protein of interest (prototypic peptides); 2) selection of the strongest fragment ion (each peptide parent-fragment pairing is called a MRM transition); 3) optimization for specific MS parameters (e.g. the collision energy) to maximize response and sensitivity; 4) multiplexing the peptide assays. Typically, we will use 2-3 peptides per target protein (and/or isoform) with peptide provides an independent quantitative value, a robustness not observed with western blots or ELISA. In our hands, MRM is linear over a concentration range of 1,000-fold and our current Triple Quadrupole MS instruments (5500 and 6500 Q-trap) have a percent coefficient of variance (% CV) of 2-5% for up to 1400 continuous runs (~2.5 weeks). We utilize MRMPilot™ Software to achieve automatic peptide and MRM transition selection from our MS/MS data as well as from in silico prediction. MRMPilot also allows us automatic MRM method building and interactive optimized peptide MRM assay. For quantitative data processing, we use MultiQuant™ support relative and absolute quantification of peptides for candidates. This software allows us to handle large data sets (scheduled MRM algorithm and large number of patients). Each MRM assays is tested in optimized in buffer to ensure maximum sensitivity, Standard curves are carried out in matrix to establish LLOD, LLOQ, ULOQ, ULOD and CV % for each assay. We multiplex as many proteins as possible within a single run. Aspects that dictate the number are the concentration range of the analyte and the retention time of each peptide used which must not overlap. Expectation is to be able to multiplex 10-15 proteins for each 10-minute assay.

ii. MRAM Sample Processing.

Throughput and reproducibility of sample preparation has improved with the development of robotic using 96 well plate taking 12 hours. Expectation is for this to be reduced to 2.5 hours. Beta-galatosidase (a protein not found in blood) is added as a sample processing control. MRM assays from Beta-galatosidase are included in all multiplexes. $N^{15}$ labeled peptides for each MRM assay is added at time of protein denaturation.

iii. MRM Analysis:

10 point standard curves are run at the start and end of each batch, 3 point quality control standard curves are included 10% of the runs, each sample is run in triplicate. All sample with CV % greater than 20% (including sample preparation) are rerun with appropriate standards. 35% of the data is manually inspected to ensure these is not baseline shift, each sample in that block is adjusted.

5.c.3. Commercial ELISA Assay i. Assay Assessment.

When commercial 96 well plate assays are available they are purchased an characterized for reproducibly and sensitivity using standard curves in the plasma matrix. Inter and intra-plate variation are determined and must be below 20%.

ii. ELISA Analysis.

Standard curves, background (blank) and spike in controls (to determine % recovery) are run on every 96 well plate. As above blocks are randomized. Background is subtracted. All samples with CV % greater than 20% are rerun with appropriate standards.

6. Statistical Analysis.

We used advanced statistical methods to further mine the discovery cohort (as outlined above). For verification and validation, we anticipate the analysis would be more straightforward with case-control comparisons using t-tests, adjustment using logistic regression for residual confounding after the matching. Meta-analysis across cohorts is conducted using random effects meta-analysis. Once we get to larger sample sizes we can evaluate prediction statistics as well but the novelty of these discovery markers suggests a stepwise approach to evaluation as knowledge about the assay and discriminatory performance matures.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Various embodiments of this application are described herein, including the best mode known to the inventors for carrying out the application. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A method of detecting protein biomarkers in a human subject, comprising:
assaying a sample obtained from the human subject, wherein the sample is plasma, and wherein the human subject has or is suspected of having chronic kidney disease; and
detecting at least 8 protein biomarkers in the sample by at least one technique selected from the group consisting of mass spectrometry, antibody method, nucleic acid aptamer method, Enzyme-linked immunosorbent assay (ELISA), immunoprecipitation, Stable isotope standards and capture by anti-peptide antibodies (SIS-CAPA), Western blot, and combinations thereof; wherein the at least 8 protein biomarkers are selected from the group consisting of Fructose-bisphosphate aldolase A (UniProt Accession No. P04075), Fibrillin-1 (UniProt Accession No. P35555), CD59 glycoprotein (UniProt Accession No. P13987), Coiled-coil domain-containing protein 80 (CCDC80) (UniProt Accession No. Q76M96), Dermcidin (UniProt Accession No. P81605), Golgi membrane protein 1 (UniProt Accession No. Q8NBJ4), T-lymphoma invasion and metastasis-inducing protein 2 (UniProt Accession No. Q8IVF5), D-tyrosyl-tRNA (Tyr) deacylase 1 (UniProt Accession No. Q8TEA8), Nck-associated protein 1 (UniProt Accession No. P55160), Talin-1 (UniProt Accession No. Q9Y490), CD2-associated protein (UniProt Accession No. Q9Y5K6), Inverted formin-2 (UniProt Accession No. Q27J81), F-actin-capping protein subunit beta (UniProt Accession No. P47756), Leukocyte immunoglobulin-like receptor subfamily A member 3 (UniProt Accession No. Q8N6C8), Noelin (UniProt Accession No. Q99784), Hornerin (UniProt Accession No. Q86YZ3), and combinations thereof.

2. The method of claim 1, wherein the mass spectrometry is selected from the group consisting of SRM, MRM, PRM, DDA, DIA, LC-MS, LC-MS/MS, LC-SRM-MS, LC-MRM-MS, LC-PRM-MS, LC-DDA-MS, LC-DIA-MS, and combinations thereof.

3. The method of claim 1, further comprising administering a treatment to the human subject.

4. The method of claim 1, further comprising:
administering a treatment to the human subject;
obtaining a post-treatment sample from the human subject; and
detecting the at least 8 protein biomarkers in the post-treatment sample from the human subject according to the method of claim 1 to determine the efficacy of the treatment.

5. The method of claim 1, further comprising detecting one or more additional protein biomarkers in the sample, wherein the one or more additional protein biomarkers are selected from the group consisting of Apolipoprotein A-II (APOA2) (UniProt Accession No. P02652), Pancreatic alpha-amylase (UniProt Accession No. P04746), Apolipoprotein C-III (APOC3) (UniProt Accession No. P02656), Polymeric immunoglobulin receptor (UniProt Accession No. P01833), Haptoglobin (UniProt Accession No. P00738), Alpha-2-macroglobulin (UniProt Accession No. P01023), Serum albumin (UniProt Accession No. P02768), Apolipoprotein L1 (APOL1) (UniProt Accession No. O14791), Alpha-1-acid glycoprotein 1 (ORM1) (UniProt Accession No. P02763), and combinations thereof.

* * * * *

SEQUENCE LISTING

<160> NUMBER OF SEQ ID NOS: 4

<210> SEQ ID NO 1
<211> LENGTH: 11
<212> TYPE: PRT
<213> ORGANISM: Homo sapiens

<400> SEQUENCE: 1

Gly Trp Val Thr Asp Gly Phe Ser Ser Leu Lys
1               5                   10

<210> SEQ ID NO 2

```
<211> LENGTH: 9
<212> TYPE: PRT
<213> ORGANISM: Homo sapiens

<400> SEQUENCE: 2

Ser Asp Val Val Tyr Thr Asp Trp Lys
1               5

<210> SEQ ID NO 3
<211> LENGTH: 5
<212> TYPE: PRT
<213> ORGANISM: Homo sapiens

<400> SEQUENCE: 3

Ser Asp Val Val Tyr
1               5

<210> SEQ ID NO 4
<211> LENGTH: 10
<212> TYPE: PRT
<213> ORGANISM: Homo sapiens

<400> SEQUENCE: 4

Gly Trp Val Thr Asp Gly Phe Ser Ser Leu
1               5                   10
```